US011072772B2

(12) United States Patent
Hansen et al.

(10) Patent No.: US 11,072,772 B2
(45) Date of Patent: *Jul. 27, 2021

(54) SYSTEM AND METHOD FOR MICROFLUIDIC CELL CULTURE

(71) Applicant: The University of British Columbia, Vancouver (CA)

(72) Inventors: Carl L. G. Hansen, Vancouver (CA); Veronique Lecault, Vancouver (CA); James M. Piret, Vancouver (CA); Anupam Singhal, Mississauga (CA)

(73) Assignee: The University of British Columbia, Vancouver (CA)

(*) Notice: Subject to any disclaimer, the term of this patent is extended or adjusted under 35 U.S.C. 154(b) by 0 days.

This patent is subject to a terminal disclaimer.

(21) Appl. No.: 16/897,782

(22) Filed: Jun. 10, 2020

(65) Prior Publication Data

US 2020/0325431 A1    Oct. 15, 2020

Related U.S. Application Data

(63) Continuation of application No. 16/818,192, filed on Mar. 13, 2020, now Pat. No. 10,738,270, which is a
(Continued)

(51) Int. Cl.
  *C12M 1/00*      (2006.01)
  *C12M 3/06*      (2006.01)

(52) U.S. Cl.
  CPC ............ *C12M 29/10* (2013.01); *C12M 23/16* (2013.01)

(58) Field of Classification Search
  CPC ...... C12M 25/02; C12M 41/36; C12M 41/46; B01L 3/502; B01L 3/50273;
  (Continued)

(56) References Cited

U.S. PATENT DOCUMENTS 6,541,243 B1   4/2003  Harris et al.
7,776,553 B2   8/2010  Love et al.
(Continued)

FOREIGN PATENT DOCUMENTS

WO   2005069980 A2   8/2005
WO   2010046775 A2   4/2010
(Continued)

OTHER PUBLICATIONS

Audet et al., "Common and distinct features of cyokine effects on hematopoietic stem and progenitor cells revealed by dose-response surface anlysis", Biotechnol. Bioeng. 80, pp. 393-404, 2002.
(Continued)

*Primary Examiner* — William H. Beisner
*Assistant Examiner* — Danielle B Henkel
(74) *Attorney, Agent, or Firm* — Potomac Law Group, PLLC

(57) ABSTRACT

Microfluidic devices and methods for perfusing a cell with perfusion fluid are provided herein, wherein the gravitational forces acting on the cell to keep the cell at or near a retainer or a retaining position exceed the hydrodynamic forces acting on the cell to move it toward an outlet. Also provided, are methods for assaying cell products within the microfluidic device.

30 Claims, 29 Drawing Sheets

Related U.S. Application Data continuation of application No. 16/526,654, filed on Jul. 30, 2019, now Pat. No. 10,704,018, which is a continuation of application No. 15/841,194, filed on Dec. 13, 2017, now Pat. No. 10,421,936, which is a continuation of application No. 13/631,629, filed on Sep. 28, 2012, now abandoned, which is a continuation-in-part of application No. 13/178,395, filed on Jul. 7, 2011, now Pat. No. 10,087,408.

(60) Provisional application No. 61/362,213, filed on Jul. 7, 2010.

(58) Field of Classification Search
CPC ........ B01L 3/502761; B01L 2200/027; B01L 2200/0647; B01L 2200/0668; B01L 2200/10; B01L 2300/0816; B01L 2300/0851; B01L 2300/0887; B01L 2400/0457; B01L 2400/0472; G01N 35/028; G01N 35/1002; G02B 21/34; Y10T 436/25
See application file for complete search history.

(56) References Cited

U.S. PATENT DOCUMENTS

| | | | |
|---|---|---|---|
| 10,087,408 | B2 | 10/2018 | Hansen et al. |
| 10,421,936 | B2 | 9/2019 | Hansen et al. |
| 10,738,270 | B2 * | 8/2020 | Hansen ................. C12M 23/16 |
| 2004/0067482 | A1 | 4/2004 | Yasuda et al. |
| 2004/0197905 | A1 | 10/2004 | Hafeman |
| 2004/0229349 | A1 | 11/2004 | Daridon |
| 2005/0054101 | A1 | 3/2005 | Felder et al. |
| 2006/0134704 | A1 | 6/2006 | Muraguchi et al. |
| 2007/0074972 | A1 | 4/2007 | Nassef et al. |
| 2009/0068170 | A1 | 3/2009 | Weitz et al. |
| 2009/0181859 | A1 | 7/2009 | Muraguchi et al. |
| 2011/0124520 | A1 | 5/2011 | Love et al. |
| 2011/0262906 | A1 | 10/2011 | Dimov et al. |
| 2011/0281764 | A1 | 11/2011 | Love et al. |
| 2011/0294678 | A1 | 12/2011 | Jin et al. |
| 2012/0009671 | A1 | 1/2012 | Hansen et al. |
| 2013/0115606 | A1 | 5/2013 | Hansen et al. |
| 2015/0360236 | A1 | 12/2015 | Garcia et al. |
| 2018/0163166 | A1 | 6/2018 | Hansen et al. |
| 2019/0367860 | A1 | 12/2019 | Hansen et al. |

FOREIGN PATENT DOCUMENTS

| | | |
|---|---|---|
| WO | 2012072822 A1 | 6/2012 |
| WO | 2012162779 A1 | 12/2012 |

OTHER PUBLICATIONS

Audet et al., Distinct role of gp130 activation in promoting self-renewal divisions by mitogenically stimulated murine hematopietic stem cells. Proceedings of the National Academy of Sciences of the United States of America 98, pp. 1757-1762, 2001.
Balagadde et al., "Long-term monitoring of bacteria undergoing programmed population control in a microchemostat", Science 309, pp. 137-140, 2005.
Belanger et al., Hemocompatibility, biocompatibility, inflammatory and in vivo studies of primary reference materials low-density polyethylene and polydimethysiloxane; A review. Journal of Biomedical Materials Research 58, pp. 467-447, 2001.
Bennett et al., "Metabolic gene regulation in a dynamically changing environment" Nature 454, pp. 1119-1122, 2008.
Benveniste et al., Intermediate-Term Hematopoietic Stem Cells with Extended but Time-Limited Reconstitution Potential, Cell Stem Cell 6, pp. 48-58, 2010.
Berthier et al., "Managing evaporation for more robust microscale assays", Part 1, Volume loss in high throughput assays. Lab Chip 8, pp. 852-859 (2008).
Bocchi et al., "Inverted open microwells for cell trapping, cell aggregate formation and parallel recovery of live cells", Lab Chip, 12, 3168-2176, 2012.
Bowie et al., "Steel factor responsiveness regulates the high self-renewal phenotype of fetal hematopoietic stem cells", Blood 109, pp. 5043-5048, 2007.
Braschler et al., "Gentle cell trapping and release on a microfluidic chip by in situ alginate hydrogel formation" Lab on a Chip 5, pp. 553-559, 2005.
Brummendorf et al., "Asymmetric cell divisions sustain long-term hematopoiesis from single-sorted human fetal liver cells", J. Exp. Med. 188, pp. 1117-1124, 1998.
Cheong, R. et al. High Content Cell Screening in a Microfluidic Device. Molecular & Cellular Proteomics 8, 433-442 (2009).
Cohen, AR. et al. "Computational prediction of neural progenitor cell fates" Nat Meth 7, 213-218 (2010).
Di Carlo, D. et al. "Single-cell enzyme concentrations, kinetics, and inhibition analysis using high-density hydrodynamic cell isolation arrays" Anal. Chem. 78, 4925-4930,doi:10.1021/ac060541s (2006).
Duffy, D.C. et al. "Rapid Prototyping ofMicrofluidic Systems in Poly(dimethylsiloxane)." Analytical Chemistry 70, 4974-4984 (1998).
Dykstra, B. et al. High-resolution video monitoring of hematopoietic stem cells cultured in single-cell arrays identifies new features of self-renewal. Proc. Natl. Acad. Sci. USA 103, 8185-8190 (2006).
Dykstra, B. et al. Long-term propagation of distinct hematopoietic differentiation programs in vivo. Cell Stem Cell 1, 218-229 (2007).
Eilken, H.M. et al. "Continuous single-cell imaging of blood generation from haemogenic endothelium" Nature 457, 896-900 (2009).
El-Ali, J. et al. Cells on chips. Nature 442, 403-411 (2006).
Faley, S., et al. Microfluidic platform for real-time signaling analysis of multiple single T cells in parallel. Lab on a Chip 8, 1700-1712 (2008).
Faley, S.L. et al. Microfluidic single cell arrays to interrogate signalling dynamics of individual, patient-derived hematopoietic stem cells. Lab Chip 9, 2659-2664 (2009).
Figallo, E. et al. Micro-bioreactor array for controlling cellular microenvironments. Lab Chip 7, 710-719 (2007).
Gomez-Sjoberg, R. et al. Versatile, fully automated, microfluidic cell culture system. Analytical Chemistry 79, 8557-8563, 2007.
Hansen, C.L et al. A microfluidic device for kinetic optimization of protein crystallization and in situ structure determination. J. Am. Chem. Soc. 12 8, 3142-3143, 2006.
Heo, Y.S. et al. Characterization and resolution of evaporation-mediated osmolality shifts that constrain microfluidic cell culture in poly(dimethylsiloxane) devices. Anal. Chem. 79, 1126-1134, 2007.
Hosokawa, M., et al. High-Density Microcavity Array for Cell Detection: Single-Cell Analysis of Hematopoietic Stem Cells in Peripheral Blood Mononuclear Cells. Analytical Chemistry 81, 5308-5313, 2009.
Hung, P.J. et al. "Continuous perfusion microfluidic cell culture array for high-throughput cell-based assays" Biotechnol. Bioeng. 89(1): 1-8, 2005.
Kamei, K.I., et al. An integrated microfluidic culture device for quantitative analysis of human embryonic stem cells Lab on a Chip 9, 555-563, 2009.
Kent, D.G. et al. Prospective isolation and molecular characterization of hematopoietic stem cells with durable self-renewal potential. Blood 113 , 6342-6350, 2009.
Kent, D.G. et al. Steel factor coordinately regulates the molecular signature and biologic function of hematopoietic stem cells. Blood 112 , 560-567, 2008.
Kim, L. et al. Microfluidic arrays for logarithmically perfused embryonic stem cell culture. Lab Chip 6, 394-406, 2006.
King, K.R. et al. "A high-throughput microfluidic real-time gene expression living cell array" Lab on a Chip 7, 77-85, 2007.
Kobel, S. et al. "Optimization of microfluidic single cell trapping for long-term on-chip culture" Lab on a Chip 10, 857-863, 2010.

(56) References Cited

OTHER PUBLICATIONS

Korin, N. et al. Periodic "flow-stop" perfusion microchannel bioreactors for mammalian and human embryonic stem cell long-term culture. Biomed. Microdevices 11, 87-94, 2009.
Kurth, I. et al. Hematopoietic stem and progenitor cells in adhesive microcavities. Integrative Biology 1, 427-434, 2009.
Lecault, V. et al."High-throughput analysis of single hematopoietic stem cell proliferation in microfluidic cell culture arrays" Nature Methods 8, 581-586, 2011.
Lecault, V. et al. High-Throughput Culture of Single Cells in Nanovolume Bioreactors Allows Assessment of Heterogeneity in Hematopoietic Stem Cell-Enriched Populations. Poster session presented at Engineering Conferences International Cell Culture Engineering XII. Apr. 25-29, 2010; Banff, AB, Canada.
Lecault, Veronique et al. "High-Throughput Clonal Selection of Antibody-Producing CHO Cells Using a Microfluidic Cell Culture Platform" CHO Poster Presented at Single Cell Analysis Summit Sep. 29&30 2011 San Francisco, California USA.
Lecault, Veronique et al. "High-Throughput Clonal Selection of Antibody-Producing CHO Cells Using a Microfluidic Cell Culture Platform" American Chemical Society Meeting in San Diego, California on Mar. 28, 2012.
Lecault, Veronique et al. "Microfluidic Platform for Rapid Clonal Selection of Highly Productive Cell Lines" ECI Cell Culture Engineering Conference XIII Poster on Apr. 22 to 27 2012 Scottsdale, Arizona USA.
Lee, P.J. et al. Nanoliter scale microbioreactor array for quantitative cell biology. Biotechnol. Bioeng. 94, 5-14, 2006.
LI, P.C.H. et al. "Transport, retention and fluorescent measurement of single biological cells studied in microfluidic chips" Lab on a Chip 4, 174-180, 2004.
Li, X. & Li, P.C.H. On-Chip Dye Loading, Cell Contraction by Chemical Stimulation, and Quantitative Fluorescent Analysis of Intracellular Calcium. Anal. Chem. 77, 4315-4322, 2005.
Lutolf, M.P. et al. Perturbation of single hematopoietic stem cell fates in artificial niches. Integr. Biol. 1, 59-69, 2009.
Ma, N.N. et al. Fabrication and use of a transient contractional flow device to quantify the sensitivity of mammalian and insect cells to hydrodynamic forces. Biotechnol. Bioeng. 80, 428-437, 2002.
Marcy, Y. et al."Dissecting biological "dark matter" with single-cell genetic analysis of rare and uncultivated TM7 microbes from the human mouth" Proc. Natl. Acad. Sci. U. S. A 104, 11889-11894, 2007.
Mehta, G. et al. Polyelectrolyte-clay-protein layer films on microfluidic PDMS bioreactor surfaces for primary murine bone marrow culture. Advanced Functional Materials 17, 2701-2709, 2007.
Moeller, H.C. et al. A microwell array system for stem cell culture. Biomaterials 29, 752-763, 2008.
Neuman, K.C. et al. "Characterization of photodamage to *Escherichia coli* in optical traps" Biophys. J. 77, 2856-2863, 1999.
Ohta, H. et al. Near-maximal expansions of hematopoietic stem cells in culture using NUP98-HOX fusions. Exp. Hematol. 35, 817-830, 2007.
Paguirigan, AL. & Beebe, D.J. From the cellular perspective: exploring differences in the cellular baseline in macroscale and microfluidic cultures. Integr. Biol. 1, 182-195, 2009.
Paguirigan, AL. & Beebe, D.J. Microfluidics meet cell biology: bridging the gap by validation and application of microscale techniques for cell biological assays. Bioessays 30, 811-821 (2008).
Pineault, N. et al. "Differential and common leukemogenic potentials of multiple NUP98-Hox fusion proteins alone or with Meisl" Molecular and Cellular Biology 24, 1907-1917 (2004).
Pineault, N. et al. Transplantable cell lines generated with NUP98-Hox fusion genes undergo leukemic progression by Meisl independent of its binding to DNA Leukemia 19, 636-643 (2005).
Rantala, J.K. et al. "A cell spot microarray method for production of high density siRNA transfection microarrays" BMC Genomics 12:162 (2011).
Regehr, K.J. et al. Biological implications of polydimethylsiloxane-based microfluidic cell culture. Lab Chip 9, 2132-2139 (2009).
Rowat, AC. et al. Proceedings of the National Academy of Sciences 106, 18149-18154 (2009).
Satyanaray Ana, S. et al. Stamp-and-stick room-temperature bonding technique for microdevices. J. Microelectromech. Syst. 14(2): 392-399 (2005).
Schroeder, T. Asymmetric cell division in normal and malignant hematopoietic precursor cells. Cell Stem Cell 1, 479-481 (2007).
Skelley, AM et al. "Microfluidic control of cell pairing and fusion" Nat Methods 6(2):147-152 (2009).
Taylor, R.J. et al. Dynamic analysis of MAPK signaling using a high-throughput microfluidic single-cell imaging plafform. Proc. Natl. Acad. Sci. USA 106, 3758-3763 (2009).
Thorsen, T. et al. Microfluidic large-scale integration. Science 298, 580-584 (2002).
Toriello NM, et al. "Integrated microfluidic bioprocessor for single-cell gene expression analysis" Proc Natl Acad Sci USA 105(51):20173-20178 (2008).
Uchida, N. et al. Different in vivo repopulating activities of purified hematopoietic stem cells before and after being stimulated to divide in vitro with the same kinetics. Experimental Hematology 31, 1338-1347 (2003).
Unger, M.A. et al. Monolithic microfabricated valves and pumps by multilayer soft lithography. Science 288, 113-116 (2000).
Voldman, J. et al. A microfabrication-based dynamic array cytometer Anal. Chem. 74, 3984-3990 (2002).
Wang, Z.H. et al. High-density microfluidic arrays for cell cytotoxicity analysis. Lab Chip 7, 740-745 (2007).
Warren L, et al. "Transcription factor profiling in individual hematopoietic progenitors by digital RT-PCR" Proc Natl Acad Sci USA 103(47):17807-17812 (2006).
Wheeler, A.R., et al. Microfluidic device for single-cell analysis. Analytical Chemistry 75, 3581-3586 (2003).
Wlodkowic, D.et al. Microfluidic Single-Cell Array Cytometry for the Analysis of Tumor Apoptosis. Analytical Chemistry 81, 5517-5523 (2009).
Yamazaki, S. & Nakauchi, H. Insights into signaling and function of hematopoietic stem cells at the single-cell level. Curr. Opin. Hematol. 16, 255-258 (2009).
Young, J.C. et al. Retention of quiescent hematopoietic cells with high proliferative potential during ex vivo stem cell culture Blood 87, 545-556 (1996).
Defendant Berkeley Lights, Inc.'S Answer and Amended Affirmative Defenses to Amended Complaint and Amended Counterclaims, United States District Court for the District of Delaware, Civil Action No. 20-cv-1230-RGA, filed Oct. 30, 2020.
Defendant Berkeley Lights, Inc.'S Answer and Amended Affirmative Defenses to Amended Complaint and Amended Counterclaims, United States District Court for the District of Delaware, Civil Action No. 20-cv-1116-RGA, filed Oct. 30, 2020.

* cited by examiner

FIG. 9A
FIG. 9B
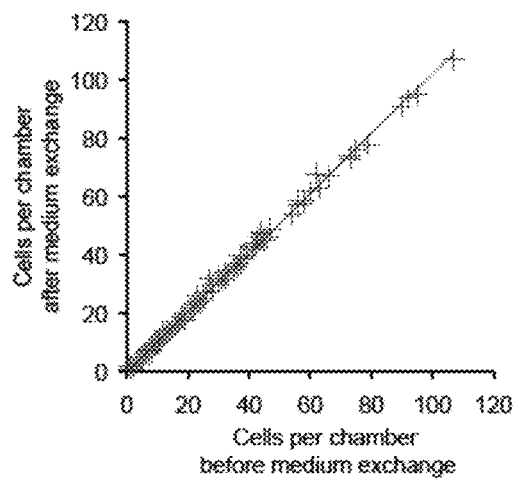
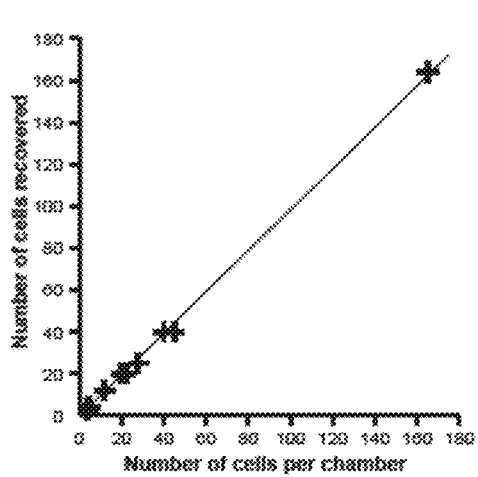
FIG. 9C
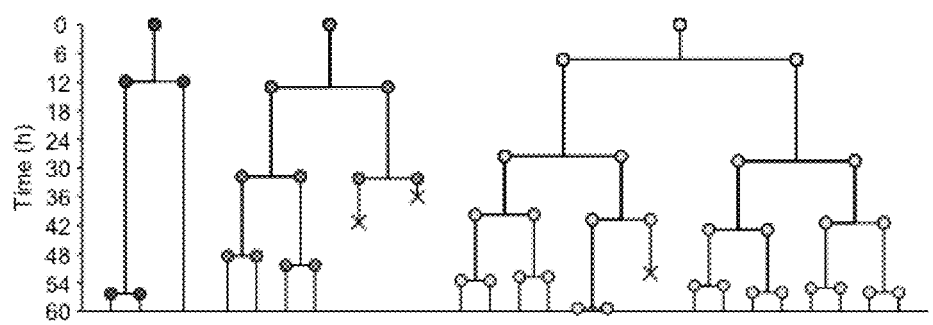
FIGURES 9A-9C

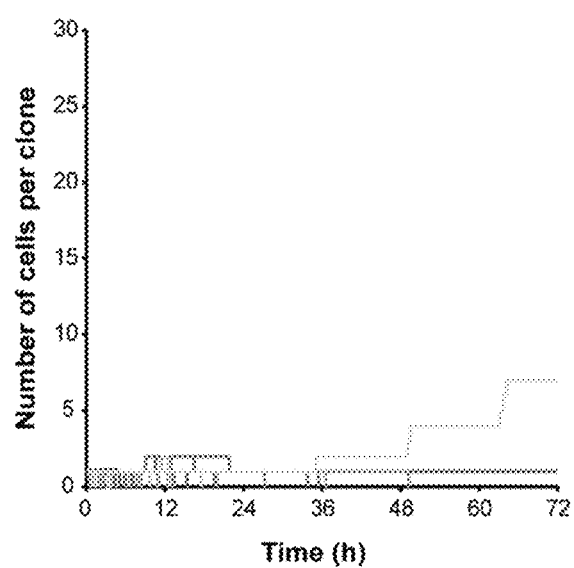
FIG. 13A
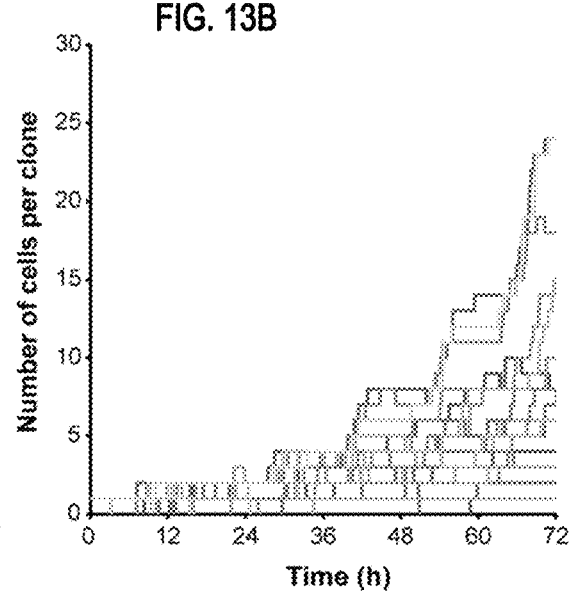
FIG. 13B
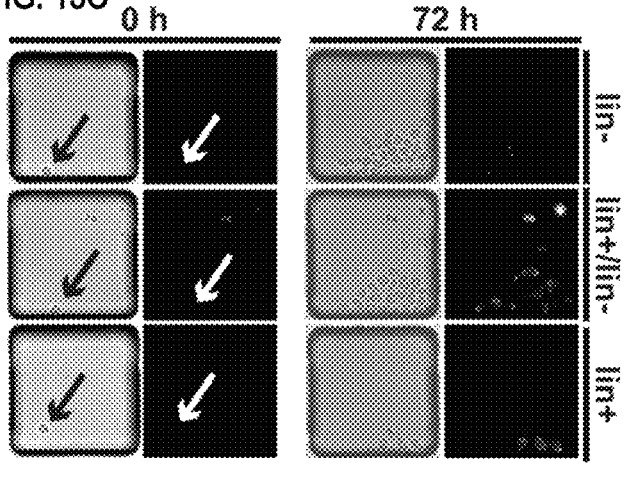
FIG. 13C
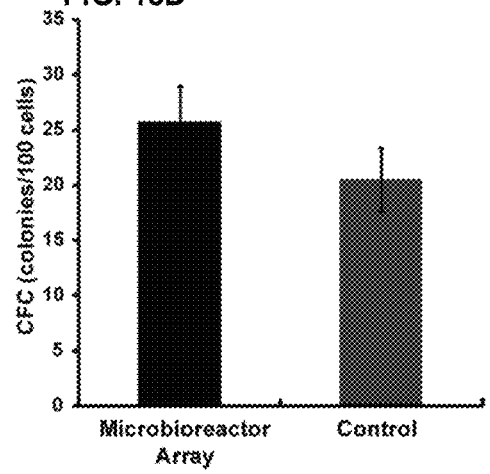
FIG. 13D
FIGURES 13A-13D FIG. 15A
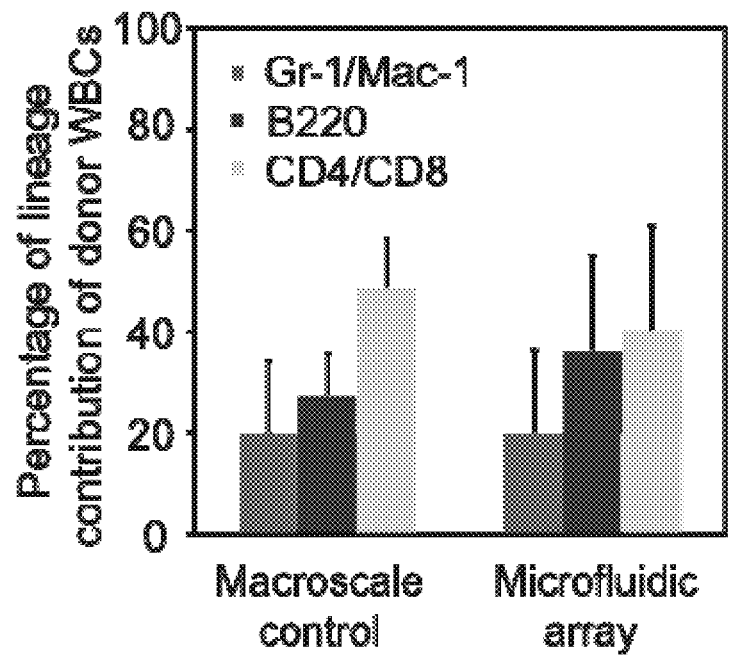
FIG. 15B
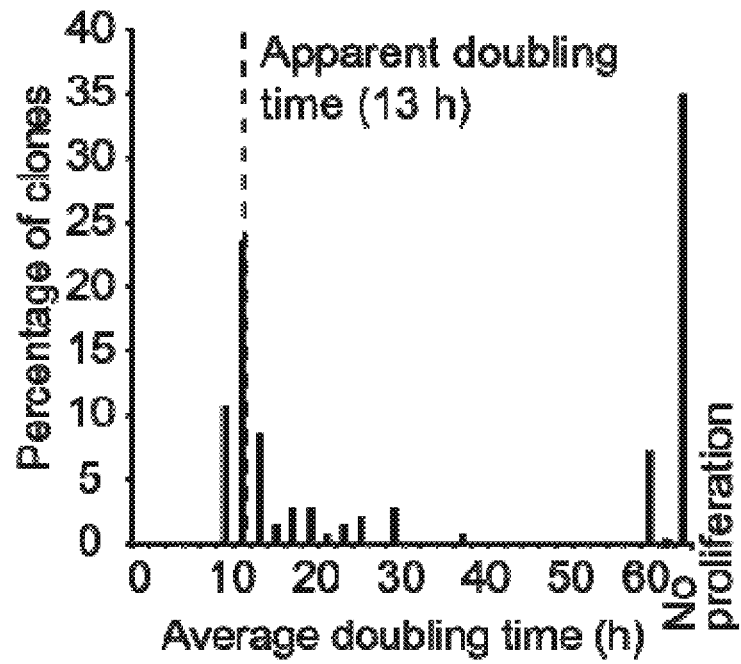
FIGURES 15A-15B FIG. 17A
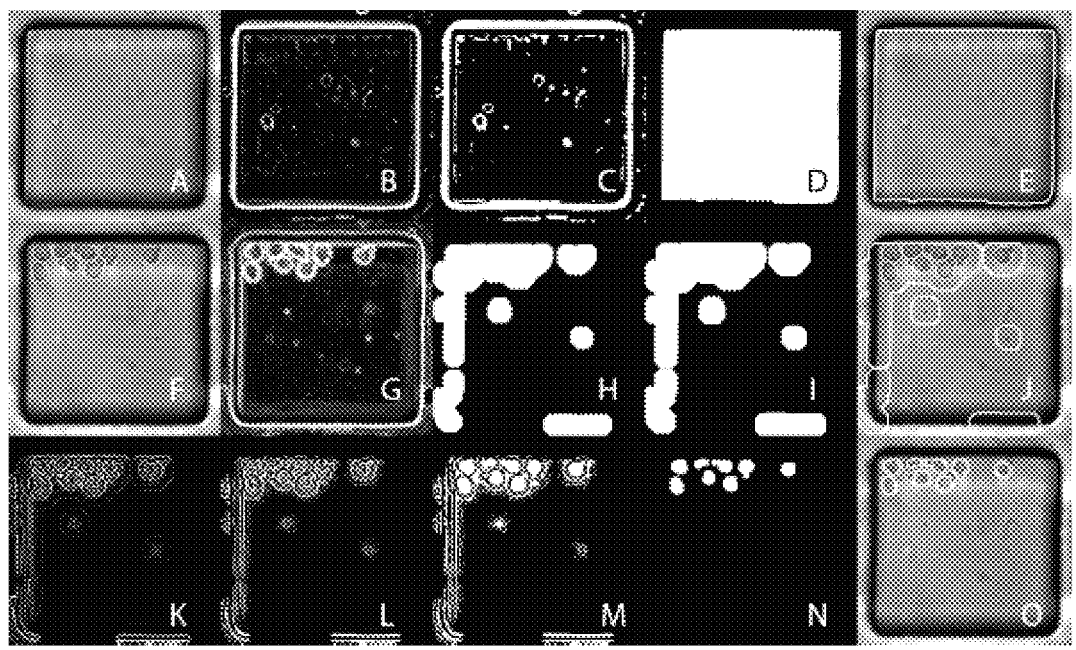
FIG. 17B
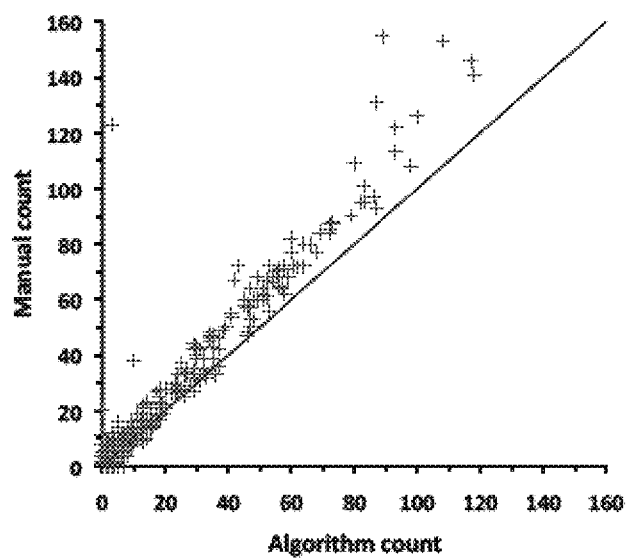
FIGURES 17A-17B FIG. 20A
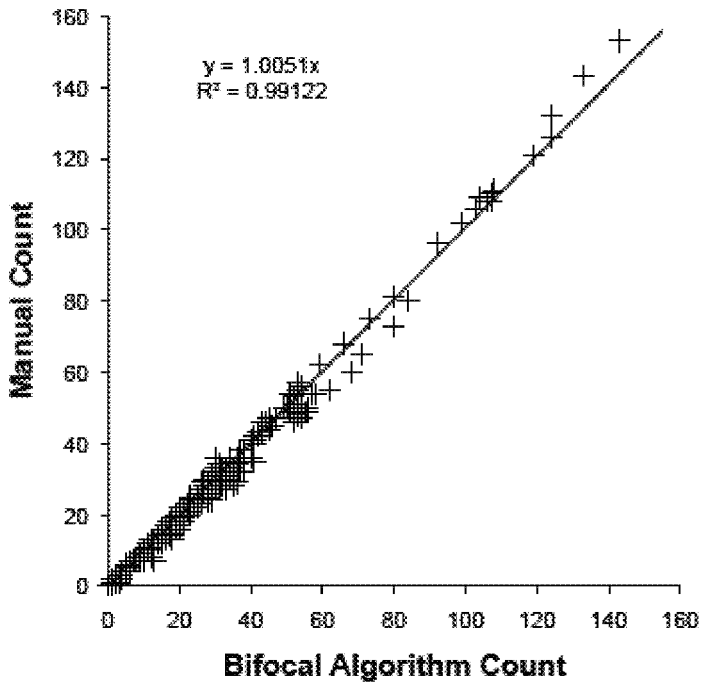
FIG. 20B
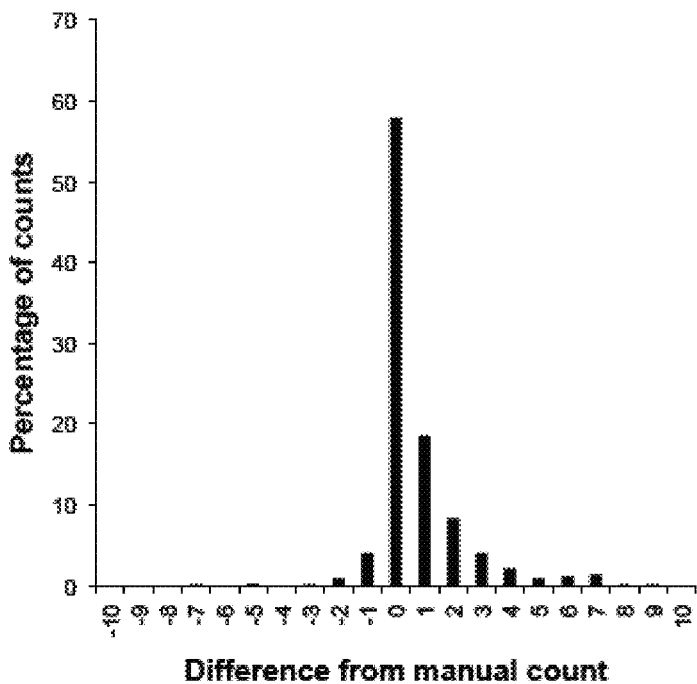
FIGURES 20A-20B FIG. 30A
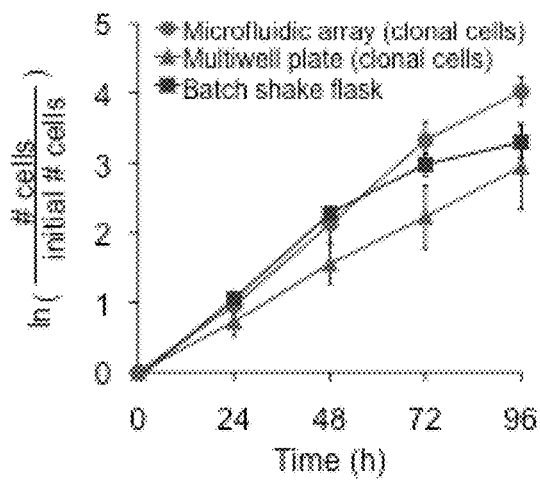
FIG. 30B
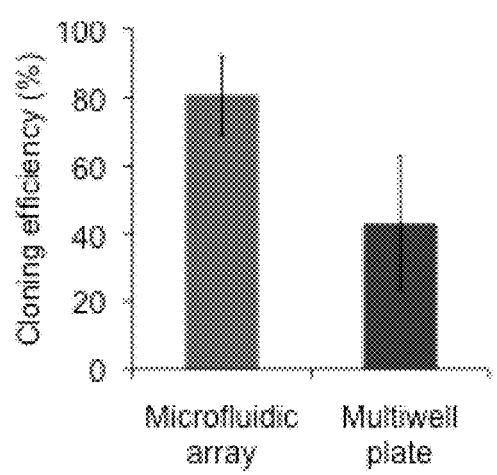
FIGURES 30A-30B
FIG. 31A
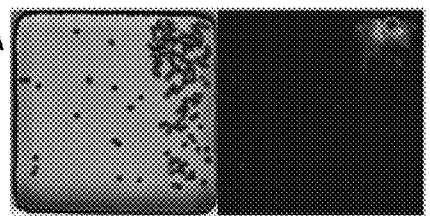
FIG. 31B
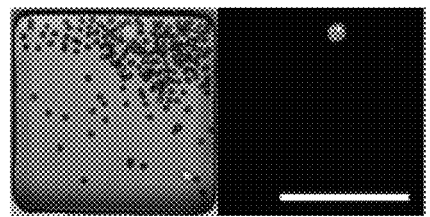
FIG. 31C
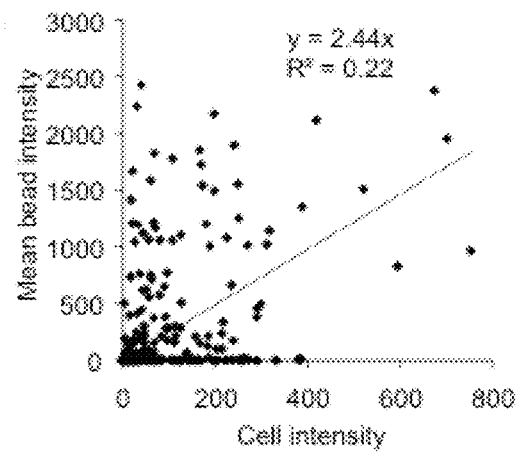
FIGURES 31A-31C

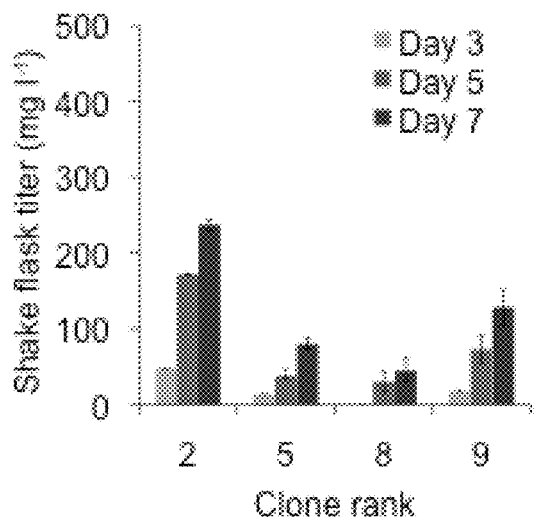
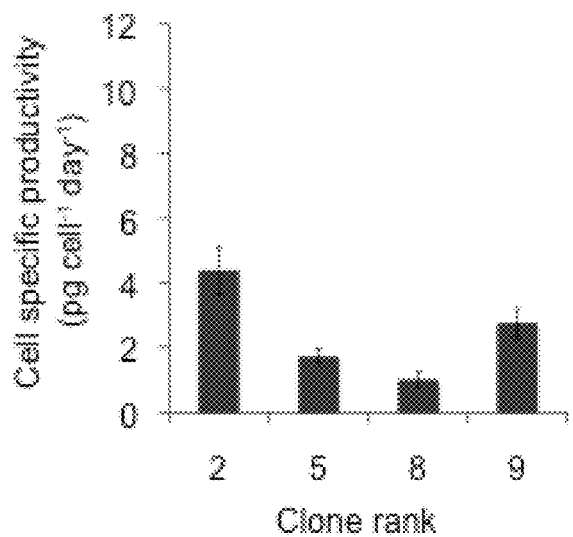
FIGURES 34A-34B
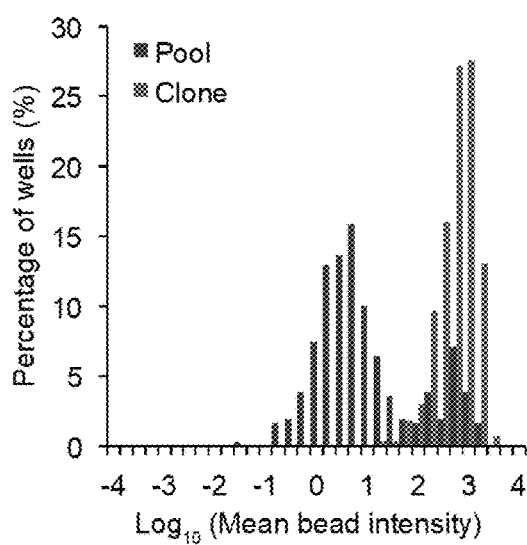
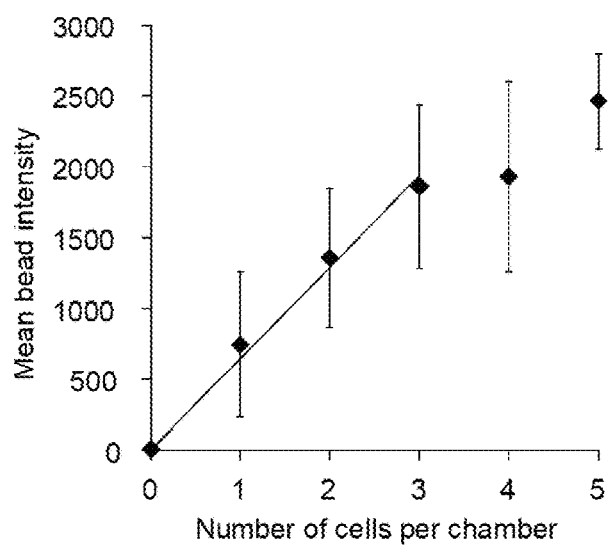
FIGURES 35A-35B

SYSTEM AND METHOD FOR MICROFLUIDIC CELL CULTURE

CROSS REFERENCE TO RELATED APPLICATIONS

This application is a continuation of U.S. patent application Ser. No. 16/818,192, filed Mar. 13, 2020, now U.S. Pat. No. 10,738,270, which is a continuation of U.S. patent application Ser. No. 16/526,654, filed Jul. 30, 2019, now U.S. Pat. No. 10,704,018, which is a continuation of U.S. patent application Ser. No. 15/841,194, filed Dec. 13, 2017, now U.S. Pat. No. 10,421,936, which is a continuation of U.S. patent application Ser. No. 13/631,629, filed Sep. 28, 2012, now abandoned, which is a continuation-in-part of U.S. patent application Ser. No. 13/178,395, filed Jul. 7, 2011, now U.S. Pat. No. 10,087,408, entitled "SYSTEM AND METHOD FOR MICROFLUIDIC CELL CULTURE", which application claims priority benefit of U.S. Provisional Patent Application Ser. No. 61/362,213 filed Jul. 7, 2010, each of which is incorporated herein by reference in its entirety.

BACKGROUND

1. Field

This invention relates to microfluidic devices. In particular, the invention relates to microfluidic devices and their uses and methods for culturing cells for extended periods of time.

2. Description of Related Art

Cell population heterogeneity poses a major obstacle to understanding complex processes that govern tissue-specific cellular responses, differentiation, and disease development. Averaged measurements of large numbers of cells often obscure the variable responses of individual or rare cells. New technologies for studying cellular heterogeneity at the single cell level under well-defined chemical environments are therefore of great interest in the study of cells (for example, stem cell fields).

The need for scalable single cell analysis is particularly acute in the study of hematopoietic stem cell (HSCs) growth and differentiation. The analyses of clonal cultures derived from single HSCs have been performed for a number of years and these have already provided some insights into the proliferation kinetics of the input cells, their in vitro responses to varying growth factor conditions, and their rapid loss ex vivo of the differentiation pattern that is typically preserved when they expand in vivo. Such experiments have shown that quiescence and delayed cell cycle entry correlate with higher potency (Brummendorf, T H. et al. J. Exp. Med. 188, 1117-1124 (1998); Audet, J. et al. Biotechnol. Bioeng. 80, 393-404 (2002)), that asymmetric cell divisions are features of HSCs with long-term hematopoietic activity (Ma, N. N. et al. Biotechnology and Bioengineering 80, 428-437 (2002)), and that the probability of HSCs executing a self-renewal decision in vitro is regulated by the types and concentrations of growth factors to which it is exposed (Ma, N. N. et al. Biotechnology and Bioengineering 80, 428-437 (2002); Pineault, N. et al. *Leukemia* 19, 636-643 (2005); Pineault, N. et al. *Molecular and Cellular Biology* 24, 1907-1917 (2004)). Recently, the study of HSCs using automated time-lapse imaging and, in some cases, micropatterned substrates, has enabled increased time resolution and the identification of new phenotypes associated with particular biological behaviors (Audet, J. et al. Biotechnol. Bioeng. 80, 393-404 (2002); El-Ali, J. et al. Nature 442, 403-411 (2006); Faley, S. L. et al. Lab Chip 9, 2659-2664 (2009); Wang, Z. H. et al. Lab Chip 7, 740-745 (2007); Figallo, E. et al. Lab Chip 7, 710-719 (2007)). These latter approaches indicate the power of higher throughput micro-culture systems, even though they lack desirable features including variable schedules of medium exchange.

Integrated microfluidic systems provide many advantages for live-cell microscopy tracking studies. These advantages include low reagent consumption, precise temporal control over-growth conditions, and an ability to work with but not be limited to small numbers of input cells. Although these advantages have been well explored to analyze yeast and bacterial cell responses (Balagadde, F. K. et al. Science 309, 137-140 (2005); Taylor, R. J. et al. Proc. Natl. Acad. Sci. USA 106, 3758-3763 (2009)), applications to mammalian cells are less developed. Whereas fluid- and cell-handling capabilities have been well established (El-Ali, J. et al. Nature 442, 403-411 (2006)), there have been relatively few reports of the application of programmable microfluidic systems to the long-term analysis of biological responses presumably owing to the difficulties in obtaining robust growth of mammalian cells in microfluidic devices. Previous mammalian microfluidic culture systems have been largely restricted to experiments with adherent cells incubated for short periods of time (hours) (Faley, S. L. et al. Lab Chip 9, 2659-2664 (2009); Wang, Z. H. et al. Lab Chip 7, 740-745 (2007)) in relatively large volumes of medium (Figallo, E. et al. Lab Chip 7, 710-719 (2007)) and/or maintained under high perfusion rates (Kim, L. et al. Lab Chip 6, 394-406 (2006); Korin, N. et al. Biomed. Microdevices 11, 87-94 (2009)). With a few notable exceptions (Lee, P. J. et al. Biotechnol. Bioeng. 94, 5-14 (2006); Hung, P. J. et al. Biotechnol. Bioeng. 89(1) (2005)), longer-term microfluidic mammalian cell culture has been characterized by reduced growth rates and even deviations from normal phenotypes (Korin, N. et al. Biomed. Microdevices 11, 87-94 (2009); Paguirigan, A. L. & Beebe, D. J. Integr. Biol. 1, 182-195 (2009)). Technical hurdles in available devices include dehydration, immobilization of nonadherent cells to facilitate medium exchange and recovery of the cultured cells for subsequent phenotypic or functional analysis. Furthermore, a microfluidic cell culture system that achieves culture conditions similar to those obtained in standard macrocultures, and allows for analysis of heterogeneous cell behaviour to generate differentiated cells both in vitro and in vivo would have practical utility.

Microfluidic devices made of polydimethylsiloxane (PDMS), a transparent and biocompatible silicone elastomer, have been widely used for cell-culture applications and provide high gas permeability for the efficient exchange of oxygen and carbon dioxide. However, PDMS is also permeable to some small molecules (Berthier, E. et al. Lab Chip 8, 852-859 (2008); Regehr, K. J. et al. Lab Chip 9, 2132-2139 (2009)) and allows for rapid transport of water vapor, which may result in dehydration (Heo, Y. S. et al. Anal. Chem. 79, 1126-1134 (2007); Hansen, C. L. G. et al. J. Am. Chem. Soc. 12 8, 3142-3143 (2006)). The high surface-to-volume ratios characteristic of nano-volume culture chambers further promote dehydration of microfluidic devices. In addition, small hydrophobic molecules can diffuse in the elastomeric material and be depleted from the medium. These variations may lead to spurious biological responses, reduced growth rates and even cell death.

SUMMARY

In a first embodiment, there is provided a method of culturing a cell, the method including: (a) retaining the cell at a retaining position within a chamber having a chamber volume; and (b) flowing a perfusing fluid through the chamber, wherein the perfusing fluid enters the chamber through an inlet at an inlet position and exits the chamber through an outlet at an outlet position, wherein the perfusing fluid has a greater velocity laminar flow adjacent the inlet and outlet positions than at the retaining position, and wherein a first region of the chamber is spaced apart from the retaining position and where the first region is interposed directly between the inlet and outlet positions.

In a further embodiment, there is provided a method of culturing a cell, the method including: (a) retaining the cell at a retaining position within a chamber; (b) flowing a perfusion fluid into the chamber through an inlet; and (c) flowing the perfusion fluid out of the chamber through an outlet wherein the outlet is positioned such that gravitational forces acting on the cell to keep it at or near the retaining position exceed hydrodynamic forces acting on the cell to move it toward the outlet.

In a further embodiment, there is provided a method of culturing a cell, the method including: retaining the cell in a volume of perfusion fluid, wherein the volume is less than about 10 nL; and placing the volume of perfusion fluid in fluid communication with a reservoir fluid, wherein the reservoir fluid has a volume greater than the volume of perfusion fluid. Alternatively, the perfusion fluid may be only in gaseous communication with the reservoir fluid.

The first region of the chamber may be defined as the volume of the chamber interposed directly between the inlet and outlet positions. Furthermore, the first region is spaced apart from the retaining position such that the velocity of the perfusion fluid at the retaining position is lower than the velocity of the perfusion fluid adjacent the inlet and outlet positions during perfusion. Similarly, the first region is spaced apart from the retaining position such that the velocity of the perfusion fluid at the retaining position is lower than the velocity of the perfusion fluid within the first region during perfusion. Accordingly, the velocity of the perfusion fluid around a cell at the retaining position may be regulated such that the velocity of the perfusion fluid is lower at the retaining position than adjacent the inlet and outlet positions during perfusion. The velocity of the perfusion fluid around a cell at the retaining position may be regulated such that the velocity of the perfusion fluid is lower at the retaining position than the first region. The speed of the perfusion fluid may be decreased to less than 50 $\mu$m/s as the perfusion fluid approaches the retaining position. The speed of the perfusion fluid may be decreased to less than 40 $\mu$m/s as the perfusion fluid approaches the retaining position. The speed of the perfusion fluid may be decreased to less than 30 $\mu$m/s as the perfusion fluid approaches the retaining position. The speed of the perfusion fluid may be decreased to less than 20 $\mu$m/s as the perfusion fluid approaches the retaining position. The speed of the perfusion fluid may be decreased to less than 10 $\mu$m/s as the perfusion fluid approaches the retaining position. The speed of the perfusion fluid may be decreased to less than 5 $\mu$m/s as the perfusion fluid approaches the retaining position. The speed of the perfusion fluid may be decreased to less than 4 $\mu$m/s as the perfusion fluid approaches the retaining position. The speed of the perfusion fluid may be decreased to less than 3 $\mu$m/s as the perfusion fluid approaches the retaining position. The speed of the perfusion fluid may be decreased to less than 2 $\mu$m/s as the perfusion fluid approaches the retaining position. The speed of the perfusion fluid may be decreased to less than 1 $\mu$m/s as the perfusion fluid approaches the retaining position. The speed of the perfusion fluid may be decreased to 0 $\mu$m/s as the perfusion fluid approaches the retaining position.

The chamber may have a top and a bottom, and the retaining position may be at the bottom. The inlet position may be proximal to the top. The outlet position may be proximal to the top. The cell may be retained at the bottom by gravitational forces. The method may further include regulating osmolarity of the perfusion fluid within the chamber. The regulating osmolarity of the perfusion fluid within the chamber may include placing the chamber in fluid communication with a bathing fluid, wherein the bathing fluid has a volume greater than the chamber volume. The regulating osmolarity of the perfusion fluid within the chamber may include placing the chamber in gaseous communication with a bathing fluid, wherein the bathing fluid has a volume greater than the chamber volume. The bathing fluid and the perfusion fluid may be iso-osmotic. The cell may be a suspension cell. The perfusion fluid may include any one or more of: a cell culture medium; an immunostaining agent; an enzymatic reagent; a dye; an oil; and a bead-containing solution.

The length of the first region may be less than or equal to a length of the shortest distance between the retaining position and the first region. The ratio of the length of the first region to the shortest distance between the retaining position and the first region may be less than 3:1. The ratio of the length of the first region to the shortest distance between the retaining position and the first region may be less than 2:1. The ratio of the length of the first region to the shortest distance between the retaining position and the first region may be less than 3:2. The ratio of the length of the first region to the shortest distance between the retaining position and the first region may be less than 1:1. The ratio of the length of the first region to the shortest distance between the retaining position and the first region may be more than 0.5. The ratio of the length of the first region to the shortest distance between the retaining position and the first region may be more than 0.6. The ratio of the length of the first region to the shortest distance between the retaining position and the first region may be more than 0.7. The ratio of the length of the first region to the shortest distance between the retaining position and the first region may be more than 0.8. The ratio of the length of the first region to the shortest distance between the retaining position and the first region may be more than 0.9. The ratio of the length of the first region to the shortest distance between the retaining position and the first region may be more than 1.0. The method may further include flowing the cell into the chamber prior to retaining the cell at the retaining position. The method may further include isolating a clone of the cell. The method may further include tracking the progeny of the cell.

The flow of the perfusing fluid may be intermittent. The flow of the perfusing fluid may be continuous. The flow of the perfusing fluid may be intermittent. The flowing of the perfusing fluid may be continuous. The replenishing of the perfusing fluid may be intermittent. The replenishing of the perfusing fluid may be continuous.

A value for x may be less than or equal to the value for y, wherein x is the length of the shortest distance between the inlet and the outlet and y is the length of shortest distance between the retaining position a region of the chamber that is interposed directly between the inlet and outlet positions. The ratio of x:y of the chamber is greater than 0.5.

The method may further include replenishing the perfusion fluid. The perfusion fluid and reservoir fluid may be iso-osmotic.

In a further embodiment, there is provided a microfluidic device for perfusing a cell with perfusion fluid, the device including: a chamber, having: (i) at least one inlet; (ii) at least one outlet; and (iii) a cell retainer; wherein the inlet and the outlet are in fluid communication with the cell retainer, and wherein the outlet is positioned such that, when the device is being perfused, gravitational forces acting on the cell to keep it at or near the retainer exceed hydrodynamic forces acting on the cell to move it toward the outlet.

In a further embodiment, there is provided a microfluidic device for perfusing a cell with perfusion fluid, the device including: a chamber, having: (i) at least one inlet; (ii) at least one outlet; and (iii) a cell retainer; wherein the inlet and the outlet are in fluid communication with the cell retainer; and wherein a first region of the chamber is interposed directly between the inlet and outlet positions and is spaced apart from the cell retainer.

The microfluidic device may further include an osmolarity regulator for regulating the osmolarity of the perfusion fluid. The osmolarity regulator may include an iso-osmotic reservoir in fluid communication with the chamber. The microfluidic device may further include a reservoir for holding a reservoir fluid, wherein the reservoir is in fluid communication with the chamber. The reservoir fluid may be iso-osmotic with the perfusion fluid. The microfluidic device may further include flow channels in fluid communication with the chamber via the at least one inlet and the at least one outlet. The chamber may have a top and a bottom, and the cell retainer is at the bottom. The inlet may be proximal to the top. The outlet may be proximal to the top. The cell may be a suspension cell. The perfusion fluid may include any one or more of: a cell culture medium; an immunostaining agent; an enzymatic reagent; a dye; an oil; and a bead-containing medium. The distance between the inlet and the outlet may be less than a distance between the cell retainer and the outlet. The ratio of the length of the distance between the inlet and the outlet to the distance between the cell retainer and the outlet may be less than 2:1. The ratio of the length of the first region to the shortest distance between the retaining position and the first region may be less than 3:1. The ratio of the length of the first region to the shortest distance between the retaining position and the first region may be less than 2:1. The ratio of the length of the first region to the shortest distance between the retaining position and the first region may be less than 3:2. The ratio of the length of the first region to the shortest distance between the retaining position and the first region may be less than 1:1. The ratio of the length of the first region to the shortest distance between the retaining position and the first region may be more than 0.5. The ratio of the length of the first region to the shortest distance between the retaining position and the first region may be more than 0.6. The ratio of the length of the first region to the shortest distance between the retaining position and the first region may be more than 0.7. The ratio of the length of the first region to the shortest distance between the retaining position and the first region may be more than 0.8. The ratio of the length of the first region to the shortest distance between the retaining position and the first region may be more than 0.9. The ratio of the length of the first region to the shortest distance between the retaining position and the first region may be more than 1.0.

The device may be an array of at least 100 chambers. The chambers may be connected in parallel. The chambers may be serially connected. The chambers may be connected in parallel and in series. The chambers may be connected partially in parallel and partially in series. The microfluidic device may be operable to be perfused intermittently. The microfluidic device may be operable to be perfused continuously.

In a further embodiment, there is provided a use of a microfluidic device described herein for tracking progeny of the cell.

In a further embodiment, there is provided a use of a microfluidic device described herein for selection of a clone of the cell.

In a further embodiment, there is provided a use of a microfluidic device described herein for observing cell-cell interactions.

In a further embodiment, there is provided a use of a microfluidic device described herein for observing autocrine effects of the cell.

The selection may be based on the amount of a factor produced by the cell or the clone. The factor may be a protein. The factor may be a nucleic acid. The cell may be a suspension cell. The use may further include recovery of the cell or clone thereof.

In a further embodiment, there is provided a method, the method including: (a) retaining a cell at a retaining position within a microfluidic chamber having a chamber volume; (b) flowing a perfusing fluid through the microfluidic chamber, wherein the perfusing fluid enters the chamber through an inlet at an inlet position and exits the chamber through an outlet at an outlet position; and (c) measuring a cell product produced by the cell within the microfluidic chamber; wherein the perfusing fluid has a greater velocity laminar flow adjacent the inlet and outlet positions than at the retaining position, and wherein a first region of the chamber is spaced apart from the retaining position, wherein the first region is interposed directly between the inlet and outlet positions.

In a further embodiment, there is provided a method, the method, including: (a) retaining a cell at a retaining position within a microfluidic chamber; (b) flowing a perfusion fluid into the microfluidic chamber through an inlet; (c) flowing the perfusion fluid out of the microfluidic chamber through an outlet wherein the outlet is positioned such that gravitational forces acting on the cell to keep it at or near the retaining position exceed hydrodynamic forces acting on the cell to move it toward the outlet; and (d) measuring a cell product produced by the cell within the microfluidic chamber.

In a further embodiment, there is provided a method, including: retaining a cell in a volume of perfusion fluid, wherein the volume is less than about 10 nL; placing the volume of perfusion fluid in fluid communication with a reservoir fluid, wherein the reservoir fluid has a volume greater than the volume of perfusion fluid; and measuring a cell product produced by the cell within the perfusion fluid.

The measuring the cell product may be selected from one or more of: lineage staining; cell-surface protein staining; antibody staining; enzymatic assay; RT-PCR analysis; PCR analysis; sequencing; functional assay; and bead capture assay to characterize the cells. The method may further include selecting cell clones based on cell characteristics. The cell characteristics may be selected from one or more of: quantity of secreted product, quality of secreted product, proliferation, morphology, gene expression, fluorescent reporter, surface proteins, genealogical pedigree, viability, apoptosis, autophagy, metabolism, clone homogeneity, and clone heterogeneity.

In a further embodiment, there is provided a microfluidic device for perfusing a cell with perfusion fluid, the device including: a chamber, having: (i) at least one inlet; (ii) at least one outlet; and (iii) a cell retainer; wherein the inlet and the outlet are in fluid communication with the cell retainer, and wherein the outlet is positioned such that, when the device is being perfused, gravitational forces acting on the cell to keep it at or near the retainer exceed hydrodynamic forces acting on the cell to move it toward the outlet.

In a further embodiment, there is provided a microfluidic device for perfusing a cell with perfusion fluid, the device including: a chamber, having: (i) at least one inlet; (ii) at least one outlet; and (iii) a cell retainer; wherein the inlet and the outlet are in fluid communication with the cell retainer; and wherein a first region of the chamber is interposed directly between the inlet and outlet positions and is spaced apart from the cell retainer.

The microfluidic device may further include a perfusion fluid comprising one or more of the following: an immunostaining agent; an enzymatic reagent; a dye; and a functionalized bead. The immunostaining agent may be selected from one or more of: monoclonal antibodies; polyclonal antibodies; fluorophores; and blocking solution. The enzymatic reagent may be selected from one or more of: horseradish peroxidase; and luminal. The dye may be selected from one or more of: rhodamine; fluorescein; calcein; Hoescht; Trypan blue; propidium iodide; and Giemsa solution. The functionalized bead may be selected from one or more of: magnetic beads; polymer beads; protein A-coated beads; and protein G-coated beads.

In a further embodiment, there is provided a method of culturing a cell and measuring cell products within a microfluidic chamber, the method including: (a) retaining the cell within the microfluidic chamber at a concentration of ≥10,000 cells per mL; (b) flowing a perfusing fluid through the microfluidic chamber; and (c) measuring a cell product produced by the cell within the microfluidic chamber.

The cell product may be secreted by the cell. The cell product may be quantified directly or indirectly by an intracellular fluorescent reporter. The cell product may be intracellular and may be released by cell lysis prior to characterization of the product. The measuring the cell product may be selected from one or more of: lineage staining; cell-surface protein staining; antibody staining; enzymatic assay; RT-PCR analysis; PCR analysis; sequencing; functional assay; and bead capture assay to characterize the cells. The method may further include selecting cell clones based on cell characteristics. The cell characteristics may be selected from one or more of: quantity of secreted product, quality of secreted product, proliferation, morphology, gene expression, fluorescent reporter, surface proteins, genealogical pedigree, viability, apoptosis, autophagy, metabolism, clone homogeneity, and clone heterogeneity. The measuring of the cell product may be selected from one or more of the following: antibody staining; enzymatic assaying; functional assaying, surface capturing, or bead capturing. The cell or clone may be maintained under culture conditions that allow subsequent clonal expansion. The cell within the microfluidic chamber may be at a concentration ≥20,000 cells per mL. The cell within the microfluidic chamber may be at a concentration ≥30,000 cells per mL. The cell within the microfluidic chamber may be at a concentration ≥40,000 cells per mL. The cell within the microfluidic chamber may be at a concentration ≥50,000 cells per mL. The cell within the microfluidic chamber may be at a concentration ≥60,000 cells per mL. The cell within the microfluidic chamber may be at a concentration ≥70,000 cells per mL. The cell within the microfluidic chamber may be at a concentration ≥80,000 cells per mL. The cell within the microfluidic chamber may be at a concentration ≥90,000 cells per mL. The cell within the microfluidic chamber may be at a concentration ≥100,000 cells per mL. The cell within the microfluidic chamber may be at a concentration ≥125,000 cells per mL. The cell within the microfluidic chamber may be at a concentration ≥250,000 cells per mL. However, the upper limit for cell density may be as high as 1 E9 cells/mL. The measuring of the secretion product may occurs between 5 minutes and 6 hours from the retaining of the cell within the microfluidic chamber.

Furthermore, the device may be selected based on the cell concentrations to avoid the need to dilute or concentrate the cells in solution, which may damage the cells, whereby the selection of chamber sizes is possible to promote a particular seeding density. For example, with a more dilute cell solution, a larger chambers may be selected and with a more concentrated cell solution, a smaller chamber may be selected.

BRIEF DESCRIPTION OF THE DRAWINGS

In drawings which illustrate embodiments of the invention.

FIG. 9A is a scatter plot depicting cell counts before and after medium exchange (2 μL/min for 10 minutes) showing minor variations attributable to cell division and cell death.

FIG. 9B is a graph depicting the efficiency of cell recovery from chambers by cell count in individual chambers and recounting of cells successfully transferred to a well, showing that on average 91% of the cells from individual colonies of different sizes could be recovered.

FIG. 9C is a graph depicting lineage tracking of cells for 3 clones following manual inspection of images, where the cells were imaged every 5 minutes and media was exchanged every 6 hrs.

FIG. 13A is a graph depicting the proliferation of lin⁻ clones in ND13 cells grown in a microfluidic device according to an embodiment, wherein the majority of the lint cells either died or did not give rise to colonies.

FIG. 13B is a graph depicting the proliferation of lin⁻ clones in a microfluidic device according to an embodiment, wherein the lin⁻ cells gave rise to colonies of different sizes.

FIG. 13C is an image depicting live immunostaining of small clonal populations in a microfluidic device according to an embodiment, wherein Nup98-HOXD13 clones were stained for lineage markers B220, Gr-1, and Mac-1 at 0 Hrs. and after 72 hours inside the microfluidic device.

FIG. 13D is a histogram depicting the progeny of Nup98-HOXD13 clones taken from a microfluidic device according to an embodiment and a control plate to compare colony forming cells (CFC—colonies/100 cells) using methylcellulose assays.

FIG. 15A is a histogram depicting the ability of NA10 hd hematopoietic populations cultured in a microfluidic device according to an embodiment and hematopoietic populations cultured in a macroscale 96-well plate to produce myeloid and lymphoid lineages as defined by lineage markers Gr-1/Mac-1, B220, and CD4/CD8.

FIG. 15B is a histogram depicting distribution of average doubling times of single HSC cells (NA10hd) in a microfluidic device according to an embodiment after being transduced with NA10 hd (apparent doubling time 13 hrs).

FIG. 17A shows representative images from an automated image analysis algorithm for cell quantification of cells in a chamber of a microfluidic device according to an embodiment, where segmentation was accomplished through three main steps: chamber segmentation (A-E), cell-containing region segmentation (F-J), and then single cell isolation (K-O). First, the individual chambers are segmented from the image background.

FIG. 17B shows a plot comparing automated image analysis depicted in FIG. 17a and manual cell counts, wherein the straight line represents the 1:1 slope.

FIG. 20A is a scatter plot comparing the results of manual cell counts and automated cell counts employing a bifocal algorithm FIG. 20B is a histogram showing absolute differences between the algorithm and manual counts.

FIGS. 23A-23G show the bead immunocapture assay to measure antibody secretion from single cells in 1,600 chambers, wherein FIG. 23A: Cells were loaded stochastically into an array of 4.1 nl chambers. FIG. 23B: Protein A-coated beads (diameter: 4.9 µm) were introduced and FIG. 23C: the chambers were isolated for 2 h using microvalves. FIG. 23D: The array was then washed and FIG. 23E: Alexa 594—Rabbit anti-human IgG (H+L) F(ab')₂ fragment was introduced for 15 min. FIG. 23F: The array was washed again and fluorescent images were taken to identify producing cells. FIG. 23G: Example of fluorescent and bright field images from the bead immunocapture assay (top left) followed by time-lapse imaging of the clone for 4.5 days. The polystyrene beads are the darker objects (black arrow) while the cells are more transparent (white arrow). Cloning medium was used throughout this assay. Scale bar, 100 µm.

FIG. 25A: The bright field image was first used to locate the well contours using blurring and subtraction of the original image. FIG. 25B: The well contour was filled to create a mask of the well. FIG. 25C: The bright field image was segmented using a set threshold and FIG. 25D: beads were filled by a combination of dilation and erosion. FIG. 25E: Both images FIG. 25B and FIG. 25D were multiplied to obtain a bead mask. FIG. 25F: The bead mask in FIG. 25E was used to segment the beads and obtain the total bead area. FIG. 25G: The fluorescence image was multiplied by the bead mask in FIG. 25E, resulting in FIG. 25H: the measurement of the total fluorescence intensity. The mean bead intensity was measured by dividing the total intensity by the total bead area.

FIG. 30A-30B show an improved cell growth and cloning efficiency in the microfluidic cell culture array FIG. 30A: Growth curves (error bars, s.d.) of CHO cells cultured in shake flasks (n=3 experiments in triplicate seeded at 2.5×10$^5$ cells $ml^{-1}$), and as single cells in 96 well plates (n=3 experiments; 27-36 clones per plate) or in microfluidic array (n=3 experiments; 50 clones tracked per experiment) FIG. 30B: Improved cloning efficiency in the microfluidic cell culture array (n=3 experiments; error bars, s.d.; P value=0.06). The cloning efficiency was measured as the percentage of clones that had more than 8 cells at 72 h. This criterion was selected based on the doubling rate of clones growing in multiwell plates (23.2 h) from FIG. 30A as clones growing at a normal rate should have undergone at least 3 divisions by 72 h.

FIGS. 31A-31C show simultaneous measurement of membrane-bound antibody and antibody secretion FIG. 31A: Example of a secreting cell with no antibody bound on its membrane. FIG. 31B: Example of a non-secreting cell with membrane-bound antibody. Cell outlines are highlighted in green. Scale bar, 100 µm. FIG. 31C: Membrane-bound antibody shows poor correlation with secretion levels.

FIG. 33A: Comparison of microfluidic secretion assay (red) with titers from at the 24-well plate stage (blue). Single cells from one experiment (n=308) are ranked based on the mean fluorescence bead intensity in each microfluidic chambers (red). Out of these, 60 clones were recovered and scaled up to the 24-well plate stage (blue). FIG. 33B: Out of the 10 of the top 12 clones that were scaled up, 4 clones were already showing signs of decreased productivity at the 24-well plate stage (shaded area) and were excluded from the screen. FIG. 33C: Batch shake flask titers of the remaining 6 clones are shown after 3, 5 and 7 days in culture (n=2; error bars, s.d.). FIG. 33D: The maximum cell specific productivity measured after 5 days in batch shake flask culture is shown as a function of the microfluidic mean fluorescence intensity measured on the single cell that gave rise to the clone (n=2; error bars, s.d.).

FIGS. 34A-34B show batch shake flask titers of eliminated clones with clones that scored high in the microfluidic assay but showed drops in productivity at the 24-well plate stage FIG. 34A: Titers after 3, 5 and 7 days in culture (n=2 flasks; error bar, s.d.) and FIG. 34B: cell specific productivities (n=2 flasks; error bar, s.d.) at day 5 are presented.

FIGS. 35A-35B show an analysis of intraclonal heterogeneity FIG. 35A: The top-ranked clone was analyzed in the microfluidic device using the bead immunocapture assay. Single cell analysis revealed a much tighter distribution for the clone than from the cell pool from which it originated. FIG. 35B: All wells were analyzed and averaged based on the number of cells they contained. There was a linear correlation between the mean bead intensity and the number of cells for up to 3 cells ($R^2$=0.99).

DETAILED DESCRIPTION

Definitions

Figure 1:
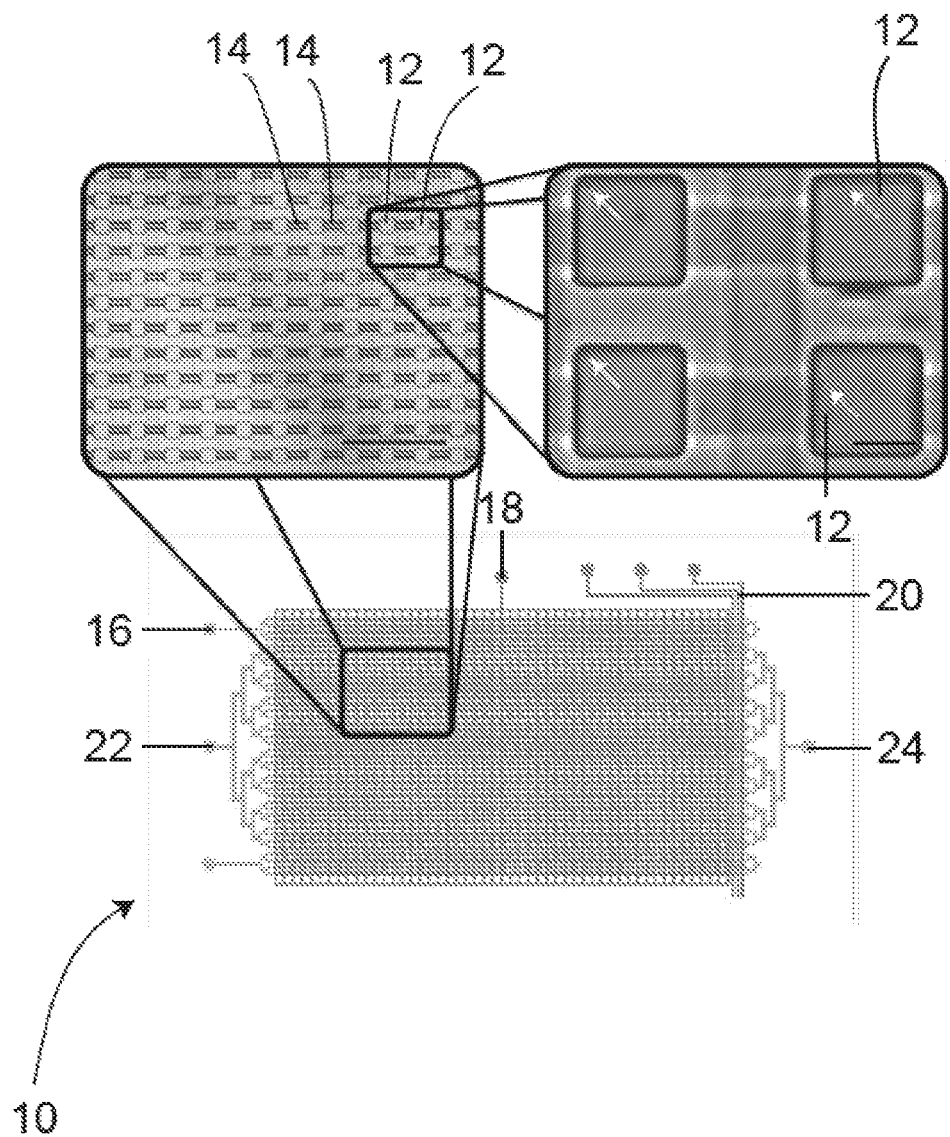
FIG. 1 is a top view of a microfluidic device with two expanded views (11×12 chamber view (size reference bar=1 mm) and a 4 chamber view (size reference bar=100 μm)) to magnify details of the microfluidic device according to an embodiment.

A "microfluidic device", as used herein, refers to any device that allows for the precise control and manipulation of fluids that are geometrically constrained to structures in which at least one dimension (width, length, height) may be less than 1 mm.

"Perfusion" or "perfusing", as used herein, refers to the passage of fluid, such as culture media, over cells for the purposes of nutritive delivery and waste removal. A person skilled in the art will understand that the fluid does not necessarily flow over the cell, but may ultimately arrive at a cell by the process of diffusion. Furthermore, perfusion or perfusing of a chamber or the microfluidic device as a whole may be continual or intermittent provided that the fluid exchange provides sufficient nutrient delivery and/or waste removal and or other factors or reagents to keep the cells viable (if that is the desired result) and/or to maintain desired conditions for the particular cell and/or assay as desired.

A "perfusion fluid", as used herein, refers to any fluid with which a cell in a chamber is perfused. A person skilled in the art will understand that a perfusion fluid may comprise factors or reagents with which it is desired to present to the cell. Factors or reagents may include components of culture medium (e.g. sugars, proteins, amino acids, vitamins, salts), proteins (e.g. interferon-α, TAT, fibronectin, bovine serum albumin), small molecules (e.g. all-trans retinoic acid, imatinib), growth factors (e.g. IL-3, IL-6, IL-11, SCF, GM-CSF), immunostaining agents (e.g. monoclonal antibodies, polyclonal antibodies, fluorophores, blocking solution), enzymatic reagents (e.g. horseradish peroxidase, luminol), oils (e.g. mineral oil, fluorinated oil), dyes (e.g. rhodamine, fluorescein, Hoescht, functionalized beads (e.g., magnetic beads, polymer beads, protein A-coated beads, protein G-coated beads), buffers (e.g. PBS, Hank's balanced solution, HEPES), PCR solutions (e.g. polymerase, nucleic acids, primers), cell transfection solutions (e.g. fibronectin, retronectin, polyethylenimine), cell fixation solutions (e.g. ethanol, formaldehyde), miRNAs, siRNAs, molecular beacons, amino acids (e.g. glutamine), antigens, semi-solid matrix (e.g. methylcellulose, Matrigel®), etc. Alternatively, a perfusion fluid may include a lysis solution to lyse the cells and allow for the assay of intracellular products.

A "chamber" or "cell capture chamber", as used herein, refers to an enclosed space within a microfluidic device in which one or more cells may be isolated from a larger population of cells as the cells are flowed through the device. Each chamber will have at least one inlet for permitting fluid, including fluid containing cells, to enter the chamber, and at least one outlet to permit fluid to exit the chamber. Persons skilled in the art will understand that an inlet or an outlet can vary considerably in terms of structure and dimension, and may be reversibly switched between an open position, to permit fluid to flow into or out of the chamber, and a closed position to seal the chamber and thereby isolate and retain its contents, whereby the aperture may also be intermediate between the open and closed positions to allow some fluid flow. Each chamber will further have at least one cell retaining position which may comprise at least one cell retainer.

The direction of fluid flow through the chamber dictates an "upstream" and a "downstream" orientation of the chamber. Accordingly, an inlet will be located at an upstream position of the chamber, and an outlet will be generally located at a downstream position of the chamber. It will be appreciated by a person of skill in the art, that the designation of an "inlet" or an "outlet" may be changed by reversing the flow within the device or by opening one or more alternative aperture(s).

A "cell retaining position" or "retainer position", as used herein, refers to a location in the chamber at which a cell is maintained during cell culture and media exchange. A retaining position may include at least one cell retainer. According to some embodiments, the retaining position may be a determined position within the chamber. However, a person skilled in the art will understand that a retaining position may comprise a zone within the chamber. The important characteristic of a retaining position is that hydrodynamic forces are insufficient to facilitate the escape of a cell through the outlet while the cell is in the retaining position and shear forces on the cell, if any, do not damage the cell. Depending on the cell type, the cell may adhere, either weakly or strongly, to the cell retaining position or a cell retainer or may be held in place by gravitational forces or a cell trap.

A "cell retainer", as used herein, refers to any structure which serves to maintain a cell within a retaining position. In a simple embodiment, the cell retainer may be the bottom of the chamber and the cells may be held in place by gravitational forces. Alternatively, a cell retainer may include a cell trap positioned to receive (and retain) a cell that is flowed into the chamber. Furthermore, a substrate may be provided at the cell retaining position that facilitates retention of the cells. For example, extracellular matrix (ECM) components or integrin or functionalized beads etc. may be deposited on at the retaining position to facilitate retention of cells.

An "inlet" or an "outlet", as used herein, may include any aperture whereby fluid flow is restricted through the inlet or outlet. There may be one or more valves to control flow, or flow may be controlled by separating the fluid channels, which lead to the inlets and outlets with a layer which prevents flow (for example, a control layer or isolation layer). Alternatively, flow may be regulated by the rate at which passed through the device. An "inlet position", as used herein, refers to a position in the chamber where an inlet is located. Similarly, an "outlet position", as used herein, refers to a position within a chamber where an outlet is located. According to embodiments, the inlet position, outlet position, and retaining position will not be co-linear.

A "first region", as used herein, refers to a region of the chamber that is interposed directly between the inlet and outlet positions. In some embodiments the first region is spaced apart from the retaining position. According to some embodiments described herein, the first region may be generally at the top of the chamber and the cell retaining position may be generally at the bottom of the chamber, such that the velocity of the fluid in the cell retaining position is slower than the velocity of the fluid in and around. In some embodiments the velocity of fluid in cell retaining position is or approaches zero and the only perfusion fluid that enters the cell retaining position is by diffusion or convection, thereby providing fresh diffusion fluids to the cell. According to some embodiments described herein, the speed of the fluid flow in the first region will be sufficiently low such that the hydrodynamic forces of the fluid urging a cell from the retaining position to an outlet are exceeded by forces, e.g. gravitational forces, urging the cell toward the cell retaining position.

A "cell trap", as used herein, refers generally to a means for receiving and retaining cells at a pre-determined location over time. A cell trap may comprise localized surface modifications for chemical immobilization of a cell. Alternatively, the cell trap may be a mechanical trap, a hydrodynamic trap (Skelley, A M et al. Nat Methods 6(2):147-152 (2009); Li, P. C. H. et al. Lab on a Chip 4, 174-180 (2004); Li, X. & Li, P. C. H. On-Chip Dye Loading, Cell Contraction by Chemical Stimulation, and Quantitative Fluorescent Analysis of Intracellular Calcium. Anal. Chem. 77, 4315-4322, doi:10.1021/ac048240a (2005); Di Carlo, D. et al. Anal. Chem. 78, 4925-4930, doi:10.1021/ac060541s (2006)), a hydrodynamic balancing trap (Rowat, A. C. et al. Proceedings of the National Academy of Sciences 106, 18149-18154, doi:10.1073/pnas.0903163106 (2009); and Kobel, S. et al. Lab on a Chip 10, 857-863 (2010)), an active valving trap (Warren L, et al. Proc Natl Acad Sci USA 103(47):17807-17812 (2006); Skelley, A M et al. Nat Methods 6(2):147-152 (2009); Li, P. C. H. et al. Lab on a Chip 4, 174-180 (2004); King, K. R. et al. Lab on a Chip 7, 77-85 (2007); Marcy, Y. et al. Proc. Natl. Acad. Sci. U.S.A 104, 11889-11894 (2007)), a dielectrophoretic trap (Voldman, J. et al. Anal. Chem. 74, 3984-3990, doi:10.1021/ac0256235 (2002)), a DNA immobilization trap (Toriello N M, et al. Proc Natl Acad Sci USA 105(51):20173-20178 (2008)), a gel encapsulation trap (Braschler, T. et al. Lab on a Chip 5, 553-559 (2005)), a magnetic trap, an acoustic trap or an optical trap (Neuman, K. C. et al. Biophys. J. 77, 2856-2863 (1999)). In various embodiments described herein, a cell trap will generally be positioned directly in the path of the smaller cross sectional of cell flow created by the funnel. Where a mechanical funnel is used according to various embodiments described herein, a trap may be positioned directly after the downstream opening of the funnel. Furthermore, additional cell trapping and funneling methods may be found in PCT/CA2011/000612.

A "mechanical trap", as used herein, refers to a physical cell trap such as a cage.

A "hydrodynamic trap", as used herein, refers to a cell trap in which the force of the fluid in motion plays a role in retaining a trapped cell in its position. A hydrodynamic trap may be also be comprised of a mechanical trap in which a cell is captured and retained. Exemplary mechanical traps are described in PCT/CA2011/000612. In certain embodiments hydrodynamic traps may be utilized. However, it may be desirable to have three or more inlets to the cell capture chamber so that the flows may be adjusted in order to direct cells to the traps.

A "dielectrophoretic trap", as used herein, refers to a cell trap in which cells, being dielectric objects, are retained by the forces generated by a non-uniform electric field.

A "magnetic trap", as used herein, refers to a cell trap employing magnetic fields to retain cells. Typically, cells will be labeled with magnetic particles, and then positioned and retained by the magnetic fields. However, magnetic traps can also be used to trap-non-magnetic cells in suitable buffers.

An "acoustic trap", as used herein, refers to a cell trap in which ultrasonic standing waves are used to generate stationary pressure gradients that exert forces that position and retain cells.

An "optical trap", as used herein, refers to a cell trap in which a tightly focused laser beam, typically a near-infra red laser beam, is used to draw cells in the direction of the beam.

The size of the cell trap may be varied according to the size, type, mechanical properties, or number of cells that are desired to be trapped. A microfluidic device according to various embodiments may further include a combination of trap designs for the capture of a range of cell types. Furthermore, each chamber could include multiple traps or each chamber or a subset of chambers may be optimized to capture a particular cell type. In such embodiments, the frequency of cells of a particular size or having particular characteristics that are trapped may be used for diagnostic or other assay purposes. Alternatively, the contents of a group of cells caught in a single trap may be processed and analyzed.

A chamber may further include cell funnel, and a "cell funnel" as used herein, refers to an apparatus which is designed to focus the flow of cells from a first location, where the cells are dispersed, to one or more desired second or more locations within the chamber wherein the cell funnel has a smaller cross sectional area of cell flow. The cell funnel may exert a force to direct cells towards the one or more desired locations within the cell capture chamber. For the purposes of clarity, "force" is defined herein as any influence that causes a free body (e.g. a cell) to undergo a change in velocity. Funnels may either span the entire height and/or width of the cell capture chamber, or partially span the height and/or width. Exemplary cell funnels are described in PCT/CA2011/000612.

A "bathing fluid", as used herein, refers to any fluid which is used to regulate the osmolarity of fluid, e.g. perfusion fluid, within a chamber. A bathing fluid may be iso-osmotic with the perfusion fluid or sufficiently close to iso-osmotic such that the osmolarity of the fluid remains in a range that is suitable for cell culturing. According to an embodiment described herein, bathing fluid will generally be present in a volume greater than a chamber. The bathing fluid may be a in a reservoir that is in gaseous communication with the chamber. For example, the reservoir may be separated from the chamber by a gas-permeable PDMS membrane, wherein the water exchange occurs in vapor phase.

An "osmolarity regulator" is a system for regulating the osmolarity of the perfusion fluid within a chamber and/or a microfluidic device as a whole. For example, the osmolarity regulator may comprise an iso-osmotic reservoir or bath in fluid communication with the chamber, wherein the iso-osmotic reservoir is filled with or resupplied with a bathing fluid that may be iso-osmotic with the perfusion fluid. The term bath and reservoir are used interchangeably with regards to osmolarity regulation of the device.

Alternatively, osmolarity may be regulated in the chambers by immersing the chambers in a large volume media bath that would be recirculated to maintain osmolarity. Alternatively, the osmolarity may be regulated in the chambers by enclosing the microfluidic device in an environmentally regulated enclosure.

"Aspect ratio", as used herein, refers to the ratio (y:x) of the shortest distance between the cell retaining position and the first region (y) to the length of the first region (x). In various embodiments where the inlet and outlet is at the top of the chamber, such that the first region is horizontal and defines an area that is interposed directly between the inlet and outlet positions, the aspect ratio will effectively been the ratio of the height of the chamber (minus the height of the first region) to the width of the chamber.

A "hydrodynamic force", as used herein, refers to a force exerted by a fluid in motion.

An "adherent cell", as used herein, refers to a cell which requires contact with a surface for growth or proliferation in vitro. For example, SAOS-2; U-2 OS; U-2 OS CycE; A172; T98G; U373MG; U87MG; SVGp12; BT-474; HMEC; MCF-7; MCF-10A; MDA-MB-231; MDA-MB-231M; MDA-MB-436; MDA-MB-468; SK-BR-3; T47D; ZR-75-1; MA11; PM1; SUM1315mo2; JIMT-1; HCC-1937; KPL-4; SUM-102PT; HeLa; HCT-116; SW480R18; SW480; HT29; Caco-2; SW620; DLD-1; LS174T; SW48; RKO; HCT-15; LS1034; AGS; CHO; SVpgC2a; HEK293; HEK293TREX; HA1ER; HA1EB; A549; A549EpoB40; U1690; A549EpoB480; NCI-H460; MDA-MB-435; UACC-257;

NIH3T3; 1A9; 1A9/PTX10; 1A9/PTX22; Ascites cells; KF28; KF28Tx; KFr13; KFr13Tx; Primary ovarian solid tumor cells; OVCAR-3; OVCAR-4; OVCAR-5; OVCAR-8; OVCAR-8/ADR; SU.86.86; CAPAN-1; Hs 766T; 22-RV-1; DuCaP; LAPC-4; LnCaP; Primary prostate stromal cells; Primary prostate epithelial cells; MDA-P; CA-1; MDA-PCA-2b; PC-3; PC-3M; PWR-1E; RWPE-1; VCaP; WPE-1/NA22; WPE-1/NB11; WPM4-1; P97E; ALVA-31; RD; and A431. Generally, most cells derived from solid tissues are adherent cells (Rantala, J. K. et al. BMC Genomics 12:162 doi:10.1186/1471-2164-12-162 (2011)).

A "suspension culture", as used herein, refers to a culture in which cells grow or multiply while suspended in a suitable fluid medium. Accordingly, a "suspension cell", as used herein, refers to any cell which is cultured while suspended in a suitable medium. A person skilled in the art will understand that a suspension cell need not naturally exist or multiply while suspended in a fluid medium, provided that the cell is adapted to grow or survive in suspension culture. Furthermore, a person skilled in the art will understand that, while a suspension cell is generally non-adherent, a suspension cell may retain some ability to adhere to a surface while being cultured in suspension. Accordingly, adherent or weakly adherent cells may be cultured as suspension cells under appropriate conditions. Suspension cells may include, for example, Chinese Hamster Ovary (CHO) cells; K562; BAF3; HEK293; Sf21; Sf9; S2; primary bone marrow or bone marrow-derived cells; primary cord blood cells, primary hematopoietic cells, primary hematopoietic stem cells; hybridoma cells or primary blood-born cancer cells. Suspension cells may be hematopoietic in origin or may be adapted to suspension culture from an adherent cell line.

A "fluid injection channel", as used herein, refers to any conduit through which fluid may be introduced into a chamber of the device. A fluid injection channel can be used to deliver any fluid to a chamber including cell suspensions, cell culture media, wash buffers, reaction mixes, factors, reagents, functionalized beads, etc.

An "auxiliary chamber", as used herein, refers to any chamber subsidiary to a cell capture chamber. Auxiliary chamber can be used for treatment or assaying of a captured cell, or its isolated contents. Treatment can include cell preparation steps including culture, washing, lysis, and fractionation. Assaying may include DNA and RNA amplification and detection, including mitochondrial PCR; genomic PCR; digital PCR, RT-PCR, RTq-PCR, multiple displacement amplification (DNA), rolling circle amplification sequencing, degenerate PCR, molecular inversion probes, molecular beacons, as well as other DNA/RNA amplification and detection methods, in vitro transcription, ligation, immunochemistry; reporter expression analysis; hybridization studies; and so forth. Several auxiliary chambers may be connected, in tandem and/or in parallel, to a single cell capture chamber, such that multiple treatments may be performed on the contents of a single cell capture chamber. A valve may be positioned between an auxiliary chamber and the cell capture chamber, or between auxiliary chambers, to regulated fluid flow between chambers.

The ability to assay cell products that reside intracellularly or extracellularly is an important capability in cell biology. Recombinant monoclonal antibodies (mAbs) are one example of a cell product and are used in biological assays (for example, cell characterization, diagnostic testing) and as therapeutics. Chinese Hamster Ovary (CHO) cells are widely used to produce mAbs (Jayapal, K. P. et al. Chemical Engineering Progress 103, 40-47 (2007)), now favored in large part due to the demonstrated clinical safety and efficacy of their protein products.

An important bottleneck in the development of mAb production processes is the need to generate cell lines that produce large quantities of antibodies. After transduction of the gene of interest, stable clone selection with the desired product quality can take several months. This is normally the longest step in the development of a new protein production process (Chartrain, M. & Chu, L., Current Pharmaceutical Biotechnology 9(6), 447-467 (2008)). Most production cell lines have been generated by performing limiting dilution of a transduced pool of cells in multiwell plates (Chartrain, M. & Chu, L., Current Pharmaceutical Biotechnology 9(6), 447-467 (2008); Browne, S. M. & Al-Rubeai, M., Trends in Biotechnology 25(9), 425-432 (2007); and Rita Costa, A. et al. European journal of pharmaceutics and biopharmaceutics 74(2), 127-138 (2010)), with often >1,000 wells screened due to the low cell plating efficiency (McCullough, K. C. et al. Journal of Biological Standardization 11(3), 183-194 (1983); and Porter, A. J. et al. Biotechnology Progress 26(5), 1455-1464 (2010)) and the need to analyze many candidates. This method requires at least 2 weeks of culture to allow accumulation of detectable mAbs concentrations before a first measurement can be made. Lowest producing clones are eliminated while highest producers are advanced to the next phase of scale-up, a laborious process that is often repeated for subsequent rounds of sub-cloning to ensure the generation of clonal cell lines (Underwood, P. A. & Bean, P. A. Journal of Immunological Methods 107(1), 119-128 (1988)). In an effort to increase throughput and accelerate the identification of high-producing cells, several FACS-based methods have been developed. Cell sorting strategies can be coupled with single-cell deposition, hence eliminating the need for sub-cloning. These strategies include immunolabeling of surface-mAb by immunostaining (Brezinsky, S. C. G. et al. Journal of Immunological Methods 277(1-2), 141-155 (2003)) and the integration of a reporter gene into the vector (Mancia, F. et al. Structure 12(8), 1355-1360 (2004); Meng, Y. G. et al. Gene 242(1-2), 201-207 (2000); Bailey, C. G. et al. Biotechnology and Bioengineering 80(6), 670-676 (2002); and Pilbrough, W. et al. Plos One 4(12), 11 (2009)), which can also be engineered to minimize the impact of the fluorescent protein on the translation of the desired product (Cairns, V. R. et al. Biotechnology and Bioengineering 108(11), 2611-2622 (2011)). However, in some systems the transcription of reporters or surface-bound mAb levels is poorly correlated with the amount of secreted mAb (Hanania, E. G. et al. Biotechnology and Bioengineering 91(7), 872-876 (2005)). Therefore, methods have been developed to directly measure the secreted proteins using gels or semi-solid medium that limit diffusion and maintain the secreted mAb molecules in the vicinity of the producing cells. For instance, single cells can be encapsulated in gel microdrops which are then subsequently labeled with a fluorescent antibody and sorted to select high producing cells (Powell, K. T. & Weaver, J. C. Bio/Technology 8(4), 333-337 (1990)). A similar approach is used with matrix-based secretion assays but the product is captured directly on biotinylated cells using an avidin-bound antibody (Manz, R., et al. PNAS 92(6), 1921-1925 (1995); and Borth, N. et al. Biotechnology and Bioengineering 71(4), 266-273 (2000).) and then fluorescently labeled before sorting. Other secretion assays involve cultivating cells in semi-solid medium over multiple days, allowing the product to concentrate around single cells, resulting in a halo of fluorescent-tagged antibody (Hanania, E. G. et al. Biotechnology and Bioengineering 91(7), 872-876 (2005); Dharshanan, S. et al.

Electronic Journal of Biotechnology 14(2) (2011)). These methods require cells to be seeded at low densities to ensure clonality in the semi-solid medium such that these conditions may not select cells that will perform well after scale-up in suspension culture medium.

Miniaturization can accelerate secretion assays by rapidly concentrating the products from single cells in small volumes while providing the throughput needed for large screens. Microwell arrays have been reported to screen for large numbers of antibody-secreting single cells (Love, J. C. et al. Nature Biotechnology 24(6), 703-707 (2006); Park, S. et al. Journal of Biotechnology 156(3), 197-202 (2011); Park, S. et al. Analytical Chemistry 82(13), 5830-5837 (2010); and Jin, A. et al. Nature Medicine 15(9), 1088-1092 (2009)). For instance, using microengraving cells are trapped into a microwell array and the secreted antibody is captured onto a functionalized glass cover that is then removed and stained prior to being scanned. This method has been multiplexed to assess levels of glycolysation in addition to secretion (Park, S. et al. Analytical Chemistry 82(13), 5830-5837 (2010)). However, selected cells must be cultured in an open array or transferred to multiwell plates for clonal expansion, both dilute conditions. Microfluidic devices capable of identifying single antibody-secreting cells isolated in picoliter-volume aqueous droplets of chambers have been reported (Singhal, A. et al. Analytical Chemistry 82(20), 8671-8679 (2010); and Koester, S. et al. Lab on a Chip 8(7), 1110-1115 (2008)). However, an underexploited feature of these enclosed systems is the use of small volumes to carry out clonal culture experiments at high seeding densities. Cloning by inoculating one cell into 4 nl yields a concentration of 250,000 cells $ml^{-1}$, thus a comparable seeding density to conventional macroscale passaging. This high concentration can provide a conditioning of the culture environment to potentially enhance the cloning efficiency compared to limiting dilution cultures. Furthermore, the isolation of clones in nanoliter volumes using integrated microvalves (Thorsen, T. et al. Science 298(5593), 580-584 (2002)) has the advantage of concentrating secreted proteins without the need for a semi-solid matrix, thus allowing for rapid detection of mAb production. Most importantly, the immobilization of suspension cells by sequestering clones in high aspect ratio microfluidic chambers (Lecault, V. et al. Nature Methods 8(7), 581-586 (2011)) allows the cells to be assayed and cultured in liquid medium similar to bioreactor cultures. The operation of these microfluidic devices can easily be automated and combined with time-lapse imaging to confirm clonality and track proliferation. A microfluidic cell culture platform is shown to rapidly assay the amount of secreted mAb from single cells and culture hundreds of clones simultaneously without the need for a semi-solid matrix. The use of this platform is shown to generate clonal cell lines from a pool of suspension-adapted CHO cells producing a recombinant IgG1 mAb.

Methods

The following methods were used for the fabrication of embodiments described herein in the examples disclosed below. It will be apparent that other methods, materials and designs are possible for creating other embodiments while remaining within the spirit of the invention described herein.

Microfluidic Cell Culture Array Fabrication

Devices were entirely made out of PDMS (Sylgard 184®, Dow Corning™). The cell culture array, control, and membrane layers were assembled using multilayer soft lithography techniques (Unger, M. A. et al. Science 288, 113-116 (2000); and Thorsen, T. et al. Science 298, 580-584 (2002).) while the iso-osmotic bath and cover layers were integrated by PDMS stamping (Satyanarayana, S. et al. J. Microelectromech. Syst. 1414, 392-399 (2005)). Chips were covalently bound to glass slides by oxygen plasma treatment. Devices were left at 80° C. for at least 5 days and autoclaved prior to use for cell culture applications to drive the curing reaction towards completion. Detailed protocols for mold and device fabrication are as follows.

Wafer Fabrication Protocol.

Each new microfluidic design is created with a drawing software such as AutoCAD. A micro-pump is located downstream of the array to avoid crushing the cells and control the speed during the loading process. Depending on the application, microfluidic cell culture arrays may contain from 1,600 to 20,000 chambers in the order of ~4 nl each. Multiplexers, isolation valves, osmolarity regulator, hydration lines etc. can be added when necessary to offer a better control of the microenvironment. Designs are printed at 20,000 dpi on transparent masks. The fabrication of molds on a silicone substrate is performed using common photolithography techniques as described below.

Flow Wafer

Flow Channels

1. Dehydrate a wafer for 10-15 minutes at 150° C.
2. Treat the wafer with vapor phase HMDS for at least 2 minutes.
3. Pour SPR220-7.0 resist on half the diameter of the wafer.
4. Ramp at 500 rpm for 10 seconds, then spin at 1,500 rpm for 90 seconds.
5. Pre-bake the wafer at 115° C. for 120 seconds.
6. Expose for 30 s.
7. Wait 30 minutes to rehydrate the resist.
8. Develop in MF319 primary bath for around 5-10 minutes, then rinse in an MF319 secondary bath.
9. Rinse with DI water and dry the wafer with compressed nitrogen.
10. Ramp from room temperature to 190° C. and leave overnight for hard bake.

Aim: 11-13 µm after reflow

Inlet Channels

1. Pour SU8-50 resist on half the diameter of the wafer.
2. Ramp at 500 rpm for 30 seconds, then spin at 2,500 rpm for 30 seconds.
3. Soft bake the wafer for 2 minutes at 65° C., 10 minutes at 95° C., and 2 minutes at 65° C.
4. Expose for 7 s.
5. Perform a post-exposure bake for 2 minutes at 65° C., 10 minutes at 95° C., and 2 minutes at 65° C.
6. Develop in an SU8 developer primary bath for around 4 minutes, then rinse in a SU8 developer secondary bath.
7. Rinse with IPA and dry the wafer with compressed nitrogen.

Aim: 40 µm

Chambers

1. Pour SU8-100 resist on half the diameter of the wafer.
2. Ramp at 500 rpm for 10 seconds, then spin at 1,300 rpm for 50 seconds.
3. Soft bake the wafer for 5 minutes at 65° C., 70 minutes at 95° C., and 5 minutes at 65° C.
4. Expose for 25 s.
5. Perform a post-exposure bake for 5 minutes at 65° C., 18 minutes at 95° C., and 5 minutes at 65° C.
6. Develop in an SU8 developer primary bath for around 20 minutes, then rinse in a SU8 developer secondary bath.

7. Rinse with IPA and dry the wafer with compressed nitrogen.
8. Ramp up and down from room temperature to 135° C. for 20 minutes.

Aim: 160 μm

Control Wafer
1. Dehydrate a wafer for 10-15 minutes at 150° C.
2. Pour SU8-50 resist on half the diameter of the wafer.
3. Ramp at 500 rpm for 10 seconds, then spin at 4,200 rpm for 40 seconds.
4. Soft bake the wafer for 2 minutes at 65° C., 4 minutes at 95° C., and 2 minutes at 65° C.
5. Expose for 2 minutes.
6. Perform a post-exposure bake for 2 minutes at 65° C., 6 minutes at 95° C., and 2 minutes at 65° C.
7. Develop in an SU8 developer primary bath for around 2 minutes, then rinse in a SU8 developer second bath.
8. Rinse with IPA and dry the wafer with compressed nitrogen.
9. Ramp up and down from room temperature to 135° C. for 20 minutes.

Aim: 25 μm

Device Fabrication Protocol

Cleaning
1. Place control wafers in plastic box with TMCS (can clean flow wafers with PDMS, but that requires degassing) for at least 2 minutes.
2. Pour 15.0 g RTV-A and 1.5 g RTV-B (10:1 ratio) per wafer into plastic cup, place cup in mixing machine, and mix together.
3. While machine mixing, wrap 1 Petri dish per wafer with aluminum foil.
4. After mixing is done, remove wafers from TMCS box and place in Petri dishes
5. Pour PDMS onto each wafer and tilt dish so that wafer is covered with PDMS and that PDMS overflows on the foil.
6. Place in 80° C. oven for at least 20 minutes.
(Can be left overnight after performing this step.)

Flow Layer
7. Place flow wafers in plastic box with TMCS for at least 2 minutes.
8. Pour 12.5 g RTV-A and 2.5 g RTV-B per wafer in 5:1 plastic cup, place cup in mixing machine, and mix together.
9. While machine mixing, prepare aluminum wrap using metal dish.
10. After mixing is done, remove wafers from TMCS box and place in aluminum holders. Press down wafer on the bottom by folding the aluminum foil on top of wafer edges.
11. Pour PDMS onto each wafer, and level the aluminum holder with 2 micropipette tips.
12. Place into degasser machine, pressurize, and degas for until no visible bubbles are left. Prepare control layer during that time.
13. Remove from degasser and level again with 2 micropipette tips. Let sit for at least 15 min.
14. Place in 80° C. oven for 18 minutes.

Control Layer
15. Cut around cleaned wafer with surgical knife and peel off PDMS to release the cleaned wafer.
16. Place cleaned control wafer in plastic box with TMCS for at least 2 minutes.
17. Pour 15.0 g RTV-A and 0.75 g RTV-B into 20:1 plastic cup, place cup in mixing machine, and mix together.
18. Turn on gas and vacuum for spinner.
19. Ensure spinner recipe ramps in 5 seconds to 500 rpm, dwells at 500 rpm for 10 seconds, ramps to 1630 rpm in 10 seconds, dwells at 1630 rpm for 60 seconds, and ramps down to 0 rpm in 5 seconds.
20. Place wafer carefully on centre of spinner chuck, close lid and secure with copper slab, and execute spinner recipe.
21. After spinning is finished, remove wafer from spinner and place in clean, new Petri dish. Let sit for at least 15 minutes.
22. Place in 80° C. oven for 18 minutes
(The control and flow layers should go into the oven at the same time.)

Membrane
23. Cut around cleaned wafer with surgical knife and peel off PDMS.
24. Pour 15.0 g RTV-A and 0.75 g RTV-B into 20:1 plastic cup, place cup in mixing machine, and mix together.
25. Turn on gas and vacuum for spinner.
26. Ensure spinner recipe ramps in 5 seconds to 500 rpm, dwells at 500 rpm for 10 seconds, ramps to 500 rpm in 10 seconds, dwells at 500 rpm for 60 seconds, and ramps down to 0 rpm in 5 seconds (A thinner membrane will result in leaky valves while a too thick membrane does not spread evenly on the wafer).
27. Place wafer carefully on centre of spinner chuck, close lid and secure with copper slab, and execute spinner recipe.
28. After spinning is finished, remove wafer from spinner and place in clean, new Petri dish.
29. Let sit for at least 15 minutes and align flow/control during that time.
30. Place in 80° C. oven for 12 minutes (13 min after flow/control duo has been placed in the oven)

Flow/Control Alignment
31. Remove both flow and control wafers from the oven.
32. Cut inside the edge of the flow wafer with a surgical knife, then peel off PDMS layer from silicon wafer.
33. Place control wafer under the microscope.
34. Align flow layer to control layer, trying not to peel off and on too much.
35. Push down any bubbles that remain between the two layers, and place in 80° C. oven for 25 min.
(The blank should come out of the oven at the same time as the flow/control combo. Time out accordingly.)

Membrane/Duo Alignment
36. Remove both flow/control duo and blank wafers from the oven.
37. Cut around the edge of the control/flow wafer with a surgical knife, then peel off PDMS layer from silicon wafer
38. Place flow/control duo onto blank layer.
39. Push down any bubbles that remain between the two layers, and place in 80° C. oven for at least one hour.
(Can be left in the oven overnight after this step.)

Bath Layer
40. Pour 40.0 g RTV-A and 4.0 g RTV-B in 10:1 plastic cup, place cup in mixing machine, and mix together (This amount of PDMS gives a sufficient height to provide good support structure for inlet and outlet ports).
41. While machine mixing, prepare aluminum wrap using metal dish.
42. Press down wafer on the bottom by folding the aluminum foil on top of wafer edges.
43. Pour PDMS onto blank wafer, and level the aluminum holder with 2 micropipette tips.

44. Place into degasser machine, pressurize, and degas until no visible bubbles are left.
45. Remove from degasser and level again with 2 micropipette tips.
46. Place in 80° C. oven for 20 minutes.

Cover Layer

47. Pour 14.0 g RTV-A and 1.4 g RTV-B in 10:1 plastic cup, place cup in mixing machine, and mix together.
48. While machine mixing, prepare aluminum wrap using metal dish.
49. Press down wafer on the bottom by folding the aluminum foil on top of wafer edges.
50. Pour PDMS onto each wafer, and level the aluminum holder with 2 micropipette tips.
51. Place into degasser machine, pressurize, and degas until no visible bubbles are left.
52. Remove from degasser and level again with 2 micropipette tips.
53. Place in 80° C. oven for 20 minutes.

Chip Assembly

54. Remove flow/control/membrane wafer, and blank wafers from the oven and let cool for about 5 minutes.
55. Dice layers into individual chips and place the chips on a ball bearing bed, flow layer down.
56. Dice the bath layer, and cut inside to create a bath having the area of the array. Leave enough space for the ports and the edges.
57. Punch holes that go in the corner of each side of the bath.
58. Dice the cover layers into pieces bigger that each chip.
59. Clean all surfaces with scotch-tape.
60. Mix together about 10.0 g RTV-A and 1.0 g RTV-B in 10:1 plastic cup, place in mixing machine, and mix together.
61. Set spinner to spin at 6,000 rpm for 6 minutes.
62. Remove blank wafer and place on spinner, pour on PDMS, and spin.
63. Remove from spinner and place in Petri dish.
64. "Stamp" the bath portion onto the liquid blank wafer and leave for 30 seconds. Make sure to stamp the right side of the bath.
65. Remove from wafer, and stick together with the flow/control portion.
66. Remove bubbles between layers.
67. Mix together about 10.0 g RTV-A and 1.0 g RTV-B in 10:1 plastic cup, place in mixing machine, and mix together.
68. Set spinner to spin at 6,000 rpm for 6 minutes.
69. Remove blank wafer and place on spinner, pour on PDMS, and spin.
70. Remove from spinner and place in Petri dish.
71. "Stamp" the cover layer portion onto the liquid blank wafer and leave for 30 seconds.
72. Remove from wafer, and stick on top of the bath portion.
73. Remove bubbles between layers
74. Leave chips to cure at room temperature overnight on ball bearings and place them in the oven.
(After this step, the chips can be left in the oven.)

Hole Punching/Bonding to Glass

75. Remove chips from the oven and punch appropriate holes with the hole puncher.
76. Clean glass slides with IPA and PDMS chips with Scotch tape.
77. Use plasma bonder to bond together chips and glass slides (25 s).
78. Cure at 80° C. in oven overnight.

The total curing time at 80° C. should equal at least 5 days before testing of chips, and chips should be 12 days old and autoclaved before use for cell culture.

Microfluidic Cell Culture

Figure 5:
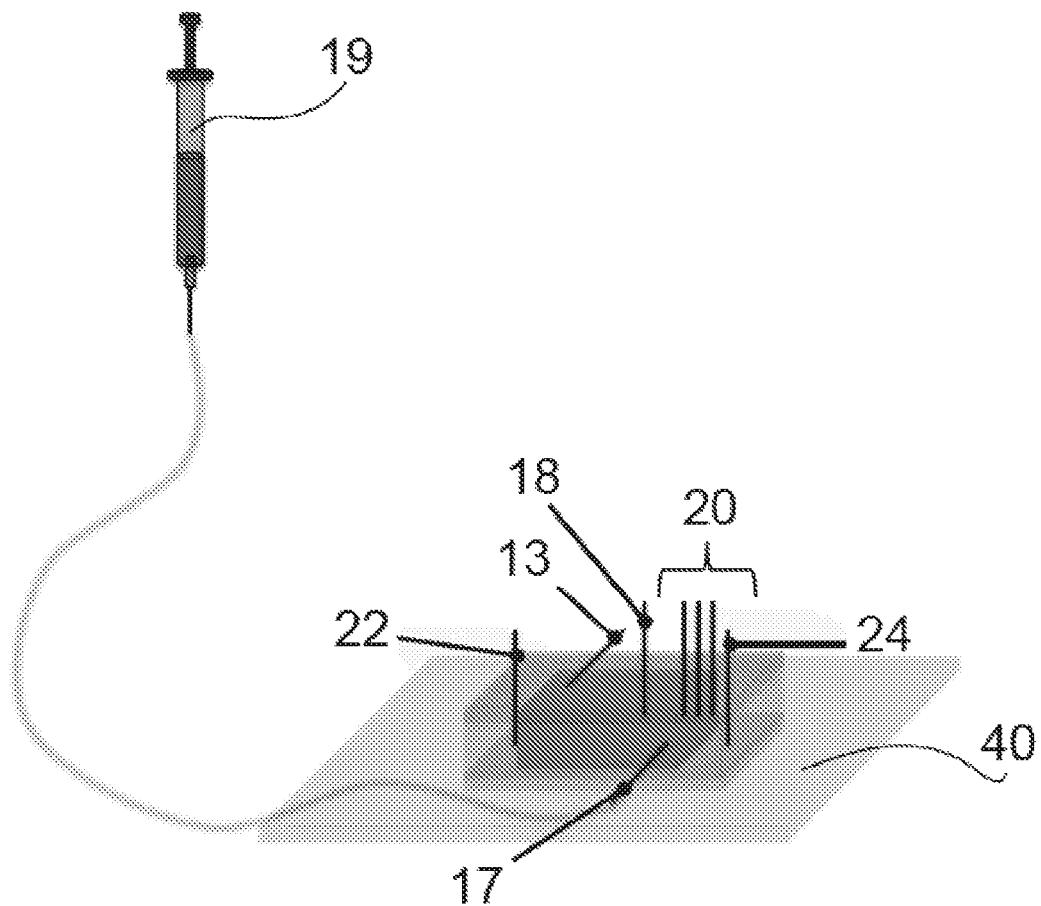
FIG. 5 is an oblique view of the microfluidic device (array) depicted in FIG. 1, further showing the microfluidic device containing an iso-osmotic bath pressurized by a syringe, the inlet and outlet, and the control lines (pumps and valves) which may be connected to solenoid actuators (not shown).

Microfluidic devices were placed inside a custom environmental chamber (Live Cell Instrument™, Chamlide). The temperature was maintained at 37° C. with 5% $CO_2$ in humidified air. Humidity saturation was maintained by the addition of two 3 cm-petri dishes filled with water inside the microscope incubator. The iso-osmotic bath and the device were filled with medium 24 hours prior to loading the cells to create equilibrium with the environment. Positive pressure was maintained by gravity in the iso-osmotic bath by connecting a 3 mL syringe filled with medium to the bath, thus preventing the formation of air bubbles that could alter imaging (see FIG. 5). The content of the bath was replaced before cell loading but was not exchanged during the experiment. Assuming a relative humidity of 90% in the microscope incubator, we calculated the water losses from the bath to be in the order of ~1% over the course of a 5-d experiment. Water vapor loss from the osmotic bath may be modeled as a near-Fickian diffusion and has a flux given by, $$I=-D\nabla C \qquad (1)$$

where D is the diffusion constant of water vapor in PDMS (~8.5×10$^{-10}$ m$^2$ s$^{-1}$) and C is the concentration of water vapor in the bulk PDMS. The iso-osmotic bath covers the area of the array (20 mm×11 mm) and has a height of ~5 mm. The majority of vapor loss occurs through the top surface of the chamber that is sealed with a 1 mm thick layer of PDMS and through the long and short sides of the bath that are sealed with 5 mm and 3 mm thick edges of PDMS respectively. This is well approximated as a one-dimensional diffusion for problem given by, $$J=-D\Delta C/L \qquad (2)$$

where L is the thickness of the PDMS sealing the top and 4 sides of the osmotic bath. A saturated water vapor concentration at 37° C. on the inside surface of the membrane is assumed (~39.3 mol m$^{-3}$). Assuming a 90% relative humidity in the incubator, the water vapor concentration at the outside surface of the chip is approximated to be 0.9×mol m$^{-3}$=35.4 mol m$^{-3}$, giving a total vapor flux of 2.1×10$^{-8}$ g s$^{-1}$. This corresponds to a loss of 13 µl over a 5 day experiment. Given a total osmotic bath volume of 1.1 ml this results in approximately 1.2% change in osmotic strength during an experiment. Cells were concentrated to 2×10$^6$ cells/mL, transferred to a Teflon® tube and plugged in the device with a stainless steel pin. The channels were flushed with medium and cells were pumped into the device at a rate of 1 µL/min. Cells were allowed to settle down in the chambers, then more cells were introduced until an adequate density was reached. In order to prevent air bubbles from forming inside the device, an inlet pressure of 4 psi and an outlet pressure of 1 psi were maintained at all times. When activated, pumps and valves were pressurized at 35 psi.

Figure 19:
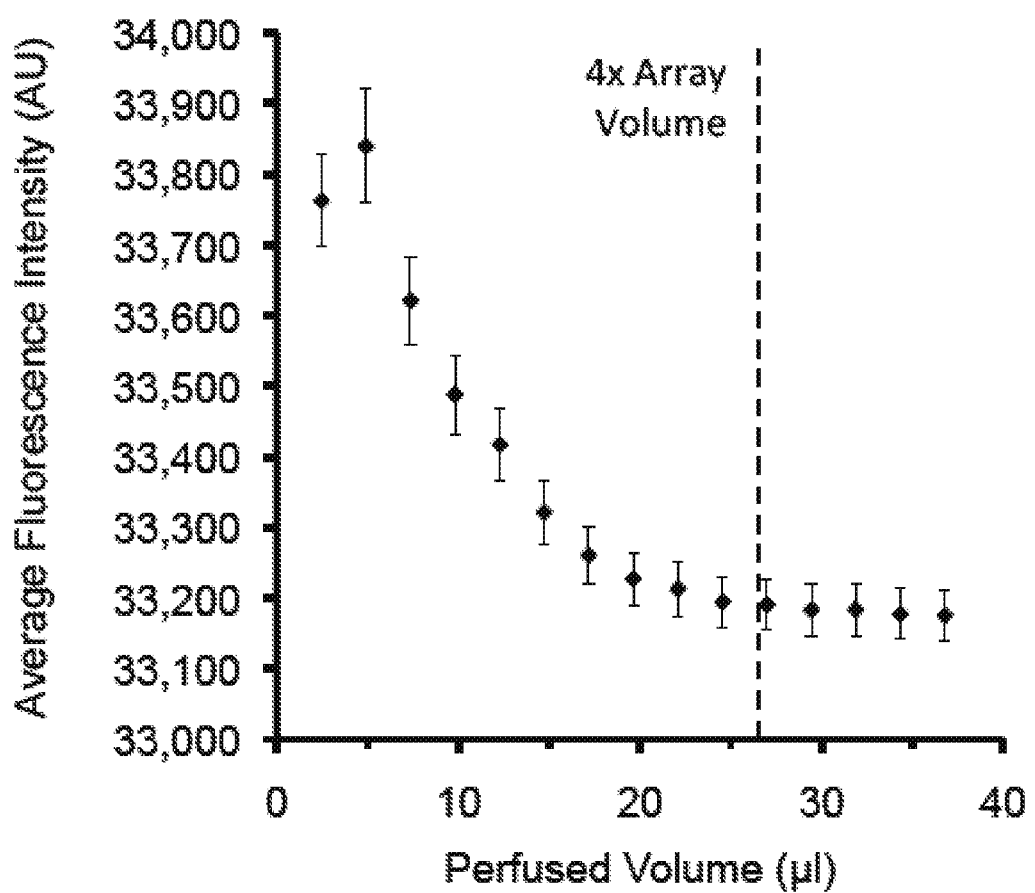
FIG. 19 is a graph of average fluorescence intensity as a function of perfused volume.

For cultures of ND13 and NA10hd cells, filtered DMEM with 15% FBS, 1.6 µg ml-1 puromycin, 100 ng ml-1 mouse SF, 10 ng ml-1 human IL-6 and 6 ng ml-1 mouse IL-3 (all cytokines from STEMCELL Technologies™) was exchanged by replacing four times the volume of the chip. Tests with fluorescent dye showed that this amount was sufficient to replace the volume of the chip. Referring to FIG. 19, a microfluidic cell culture array was loaded with medium supplemented with PE-TexasRed-streptavidin and the inlet was replaced by medium only. Pictures of the last 3 columns of the array were taken during perfusion and fluorescence intensity was quantified with Image J (National Institute of Health—Collins, T. J. BioTechniques 43 (1 Suppl): 25-30 (2007)). This demonstrates that perfusing 4-fold the volume of the array (26 µl) is sufficient for complete medium exchange. Each data point in FIG. 19 represents the average of 9 wells and error bars represent the standard deviation. Despite the low flow rates, the small length of the chambers allowed for efficient exchange of nutrients, growth factors and metabolites through a combination of convection and diffusion. For small molecules (diffusion coefficient (D) was $\sim 10^{-9}$ $m^2$ $s^{-1}$) or proteins (D was $\sim 10^{-10}$ $m^2$ $s^{-1}$), this diffusion time was approximated by τ of ~x2/D, where x is one half the chamber height, giving exchange times of 10 s or 100 s, respectively. These exchange times are substantially shorter than the 10-15 min periods used for medium perfusion.

Medium was exchanged by replacing 3 times the volume of the chip after 24, 36, 48, 54, 60, 66 and 72 hours of culture. For single-cell cultures of ND13 cells, we found that medium exchanges at 24, 36, 48, 54, 60, 66 and 72 h were sufficient to avoid conditions that led to decreased growth rates (owing to nutrient limitations and/or build-up of growth-inhibiting metabolites). Integrated micropumps and micro-valves were automatically controlled by custom scripts (LabVIEW™, National Instruments). The average doubling time (τd) for each clone was calculated by τd=72× ln(2)/ln(N72), where N72 is the number of cells per clone at 72 h. Primary E-SLAM cells were isolated as described previously (Kent, D. G. et al. Blood 113:6342-6350 (2009)) and cultured in Iscove modified Dulbecco medium supplemented with 10 mg ml-1 bovine serum albumin, 10 µg $ml^{-1}$ insulin, 200 µg $ml^{-1}$ transferrin, 40 µg ml-1 low-density lipoproteins, 100 U $ml^{-1}$ penicillin, 100 µg $ml^{-1}$ streptomycin, 2 mM glutamine (all from STEMCELL Technologies™), $10^{-4}$ M β-mercaptoethanol (Sigma™) plus 20 ng $ml^{-1}$ IL-11 (Genetics Institute) and SF, as indicated. Before starting the experiment, the volume needed to completely exchange the medium in the array (including the dead volume from the medium inlets to the multiplexer) was tested using a fluorescent dye. Ten minutes of perfusion was sufficient to remove the dye below detectable levels. Medium was exchanged every 2 h, and we pumped for 15 min for each condition to ensure that any medium remaining from a previous condition would be washed out of the array. Images were taken every 12 min in two focal planes. Cell survival and early division times were assessed manually by looking at the videos, and the individual growth curves for each clone were generated using the bifocal image analysis algorithm described below. The content of the bath was replaced before cell loading but was not exchanged during the experiment. Assuming a relative humidity of 90% in the microscope incubator, the water losses from the bath were calculated to be in the order of ~1% over the course of a 5-day experiment.

Image Acquisition

The environmental chamber and the microfluidic devices were mounted onto an inverted microscope (Axiovert 200™, Carl Zeiss™). Bright field images were acquired with a 20× objective and a CCD camera (Orca ER, Hamamatsu) connected to a computer. The entire microfluidic cell culture array was automatically scanned with a motorized staged (ProScan II™, Prior Scientific) every 6 hours or selected wells were imaged every 5 min.

Alignment and Autofocus

Chamber alignment and autofocus scripts were implemented to acquire homogeneous images, which in turn, improved the efficiency of cell segmentation. Each of the 400 image frames contained 4 chambers. The coordinates of the 4 corners of the array were first determined manually; then coordinates for the entire grid were automatically calculated by extrapolation based on the device geometry. In order to adjust for small, local device distortions introduced during device fabrication, each image frame was automatically aligned and focused. For each image frame, both a row and column average was calculated. The dark edges of the chambers produced reproducible valleys in these profiles. The locations of these valleys were then found and used to calculate the shift needed in order to align the wells to the image. Once cells were loaded into the device, the images were automatically focused by minimizing the variance of the intensity of the pixels contained within each chamber. A constant offset was then applied to each focus position to increase the accuracy of the cell segmentation algorithm. These scripts were implemented in LabVIEW™ (National Instruments).

Image Analysis

To manage the large number of images generated per experiment, a custom image analysis software program was developed to automatically count the cells at each time point in individual chambers. Cell segmentation scripts were written in MATLAB™ (MathWorks™). Referring to FIG. 17A, segmentation was accomplished through three main steps: chamber segmentation (A-E), cell-containing region segmentation (F-J), and then single cell isolation (K-O). First, the individual chambers are segmented from the image background. This step of the segmentation is accomplished by applying a bandpass filter (B) and then creating a binary image through an automatically determined threshold (C). The resulting binary image is enhanced by removing objects touching the image borders and suppressing noise by removing small objects (D). Finally, the chambers are segmented from the rest of the background by filling in the holes created by the edges of the chambers. Next, the regions containing cells are separated from the rest of the chamber. This is achieved by first applying a local standard deviation filter to enhance the highly variable regions (G). The noise in the filter response is then suppressed by removing small regions, and this result is converted into a binary image through an empirically determined threshold (H). Any holes in this result are then filled in to create the final region mask (I). To segment the individual cells from the rest of the group, a bandpass filter is applied to the output of a local standard deviation filter applied to the image (K). A top hat filter is then used to enhance the edges (L), and the bounded regions are subsequently filled (M). This result is then converted to a binary image using an automatically determined threshold, and further enhanced by removing small objects (N). FIG. 17B shows the results of a comparison between automated and manual cell counts, which demonstrated that the automated cell count was in agreement with the manual quantification of the cells The straight line represents the 1:1 slope. Deviations at higher cell numbers are caused by the shadow around the edges some chambers, thereby resulting in a slight underestimate of cell numbers using the image algorithm. An enhanced bifocal algorithm can correct this error.

For experiments requiring a high count accuracy, for instance to generate growth curves of primary HSCs, an enhanced cell-segmentation algorithm was developed based on sets of images taken at two different focal points (~50 µm apart). One image remained in focus, and the other was taken above the focal plane for use in segmentation. After segmenting the well as described above, the portion of the image that was hidden by edge shadows was identified by comparing the intensity of the region inside the perimeter to the global mean intensity of the well. The shadow was removed by calculating a brightness gradient mask around the obstructed region, combining it with the well mask and applying it to the original image. Next, the high-contrast image was used to identify the center of cells, which appeared as high-intensity spots, by applying a brightness threshold. The centers were then dilated to achieve accurate cell size representation. The focused image was used to identify cell boundaries. The image intensity was inverted and sharpened using a negative Laplacian filter to enhance the cell edges. The sharpened image was then subtracted from the original, leaving only the cell contours and well. A bandpass size filter was then applied to remove objects that did not correspond to cell perimeters. The mask containing the cell contours was combined with the cell center mask, and the image was dilated. A watershed cut algorithm was then applied to separate adjacent cells that may have been connected during the dilation and filling processes. Finally, the segmented image was compared to an initial image without cells, and objects common to both were removed. This enhanced bifocal algorithm gave high-accuracy cell counts with excellent correspondence to cell counts with excellent correspondence to cell counts determined by manual counting, as demonstrated in FIGS. 20A and 20B. FIG. 20A shows a comparison between automated and manual cell counts. The straight line corresponds to a linear least square regression. FIG. 20B shows absolute differences between the algorithm and manual counts.

Live Cell Immunostaining

For live cell immunostaining, the microincubator was turned off, and the main body containing the microfluidic device was placed on ice. For each step, at least ~26 µL (4-fold the volume of the entire array) was pumped into the array to ensure complete replacement of the solution. The device was filled with blocking solution for 20 min. The biotinylated antibody cocktail (anti-B220, Gr-1, and Mac-1-biotin) was then pumped into the device followed by incubation of the device for 40 min, and was then flushed with a solution of Hank's Balanced Salt Solution supplemented with 2% fetal bovine serum (2% Hanks). A PE-Texas-Red-streptavidin solution was then pumped into the device, which was then incubated for another 40 minutes, and flushed again with 2% Hanks until all background fluorescence had disappeared. The array was then filled with fresh medium and placed on the microscope for imaging. Bright field and fluorescent images (exposure time, 1 second) were taken for the entire array.

Cell Recovery

Micropipettes were pulled from glass capillaries to a diameter ranging between 80 to 140 µm. At the end of an experiment, the cover layer was delaminated from the chip, and selected colonies were recovered by piercing the membrane with a micropipette. To recover the entire content of the microfluidic device, the chip was flipped upside down and flushed with medium by pumping backwards at a rate of 14/min. Cells were then recovered from the Teflon® tube and placed in a tissue culture plate for further analysis. To assess the efficiency of recovery, the plate was centrifuged for 5 min at 400 g, the cells were allowed to settle for 1 hour and then manually counted using an inverted microscope.

Macroscale Cultures

ND13 cells (Pineault, N. et al. *Leukemia* 19, 636-643 (2005)) were cultured in the same medium as in the microfluidic device (e.g. DMEM with 15% fetal bovine serum supplemented with growth factors (100 ng/mL murine stem cell factor, 10 ng/mL human interleukin-6, 6 ng/mL murine interleukin-3 and selected by puromycin). Cells were passaged every 2-3 days and kept in culture for at most 60 days post-infection. Control growth curves were generated with the help of an automated cell culture analyzer (Cedex™, Innovatis™). For single cell control cultures, cells were diluted to a concentration of 5 cells/mL, and separated in 200 µL cultures in a U-shaped 96-well plate. Cells were centrifuged at 400 g for 5 minutes and allowed to settle for one hour in the incubator. Wells containing single cells to start with were counted manually every 12 hours. For colony-forming cell assays, approximately 720 cells (corresponding to 11 starting cell equivalents) were recovered from the microfluidic array or conventional 96-well plates after 72 h in culture and plated into triplicate methylcellulose assays for 14 d (MethoCult 3484™, STEMCELL Technologies™), after which the number of colonies obtained was manually counted under a microscope.

In vivo hematopoietic reconstitution assays. Bone marrow cells obtained from C57Bl/6Ly-Pep3b mice were highly enriched (~50% purity) for HSCs (Kent, D. G. et al. *Blood* 113, 6342-6350 (2009)), and a total of 50 cells (representing 25 HSCs) were retrovirally transduced with a NUP98-HOXA10hd retroviral vector and cultured for 11 days as previously described in Ohta, H. et al. (*Experimental Hematology* 35, 817-830 (2007)). On day 11, the cells were harvested and split equally between cultures in a 96 well dish (control) or a microfluidic array for a further 3 days of culture. Cells were harvested from both conditions, and then fractions representing 1/1,520th or 1/15,200th of the starting cells (estimated as a limiting dose of HSCs assuming a minimum of 60-fold or 600-fold expansion during the culture period respectively) were transplanted into lethally irradiated (810 cGy of x-rays) C57Bl/6-C2J mice along with 100,000 BM helper cells. Six weeks, and 3 and 5 months later, peripheral blood samples obtained from each recipient were analyzed for evidence of donor-derived (GFP$^+$) lymphoid and/or myeloid cells as follows. Erythrocytes were lysed with ammonium chloride (STEMCELL™) and leukocytes were suspended in 2% Hanks (STEMCELL™) and then incubated with a combination of PE-labeled anti-Ly6G/Mac-1, perCP-Cy5.5-labelled anti-B220 and APC-labeled anti-CD4/CD8 (BD Pharmingen™). Flow cytometric analysis was then performed on a FACSAria (Becton-Dickinson™)

Transport Equations for Mathematical Modeling.

The simulation of the system was performed with a three-dimensional, steady state, single phase, laminar flow model. The CFD (computational fluid dynamics) simulation has been done using FLUENT™ 6.3.26 (Fluent Inc.™). In laminar flow the Navier-Stokes equations describe the momentum transport. Therefore, the conservation of momentum in the micro-bioreactor is described by Eq. (3)

$$\frac{\partial}{\partial t}(\rho \vec{V}) + \chi \cdot (\rho \vec{V} \vec{V}) = -\nabla P + \nabla \cdot \bar{\bar{\tau}} \qquad (3)$$

The conservation of mass is described by the continuity equation as follows, $$\frac{\partial \rho}{\partial t} + \nabla \cdot (\rho \vec{V}) = 0 \qquad (4)$$

where $\rho$ (Kg m-3) is the fluid density, $\nabla$ (m s-1) is the velocity vector of the fluid, P (Pa) is the pressure, and $\bar{\bar{\tau}}$ is the stress tensor. Water has been used as a model to estimate the physical properties of fluid at 37° C.

Boundary Conditions for Mathematical Modeling

The uniform velocity profile has been defined as the inlet boundary condition. At the outflow boundary, the diffusion fluxes for all flow variables in the direction normal to the exit plane are assumed to be zero. The fluid temperature is assumed to be constant at 37° C., and a no-slip boundary condition has been specified for the velocity at the walls.

Statistical Analysis

Error bars were calculated using s.d. of the mean. Relative risk and 95% confidence intervals for the Cox proportional hazard model were calculated using the 'coxph' function from the R package 'survival' with tied times of death being handled using the Efron approximation.

Maintenance Culture and Medium

A pool of CHO-S cells producing a human monoclonal IgG1 antibody Cells was maintained in shake flasks with growth medium constituting of CD OptiCHO (Gibco, Life Technologies) supplemented with 15% CHO CD Efficient-Feed A (Gibco, Life Technologies), 15% CHO CD Efficient-Feed B (Gibco, Life Technologies), 4.5 mM L-glutamine (EmbryoMax, Millipore), 15 µg ml$^{-1}$ puromycin (Sigma-Aldrich), 0.1 mM hypoxantin and 16 µM thymidine (Gibco, Life Technologies). Shake flasks were maintained at 37° C. in a shaking incubator at 125 rpm (Minitron, Infors) with 6 or 10% $CO_2$. Cells were passaged every 2-3 days and seeded at a concentration ranging from 2-5×10$^5$ cells ml$^{-1}$.

Growth Controls in Cloning Medium

For batch growth controls, cells were seeded at a concentration of 2.5×10$^5$ cells ml$^{-1}$ and cultured in 20 ml of cloning media consisting of RPMI medium (Gibco, Life Technologies) supplemented with 17% CD OptiCHO (Gibco, Life Technologies), 3.75% CHO CD EfficientFeed A (Gibco, Life Technologies), 3.75% CHO CD EfficientFeed B (Gibco, Life Technologies), 1 mM L-glutamine (EmbryoMax, Millipore), 10 µg ml$^{-1}$ insulin EMD Millipore, 5 µg ml$^{-1}$ transferrin (CellPrime rTransferrin AF, Millipore), 2 g l$^{-1}$ albumin (Cell Prime rAlbumin AF-G, Millipore) and 15 ml$^1$ puromycin (Sigma-Aldrich). Samples were taken daily and the viable cell concentration was measured by an automated cell counter (Cedex, Illumina). To measure growth rates from single cells, a U-shaped non tissue culture-treated 96 well-plate (BD Falcon) was rinsed with cloning medium. Cells were diluted to a concentration of 5 cells ml$^{-1}$ and 200 µl was deposited in each well, equivalent to 1 cell per well. Cells were centrifuged for 5 min at 400 g and left in the incubator for 1-2 h. Wells were manually scored to identify the starting number of cells in each well. The number of cells in wells initially containing a single cell was counted manually every day.

Microfluidic Cell Culture

Microfluidic cell culture arrays containing 1,600 chambers of 4.1 nl (160 µm×160 µm×160 µm) were fabricated as described in Appendix B. Two days prior to loading the cells, the iso-osmotic bath was filled with cloning medium supplemented with penicillin (100 U ml$^{-1}$) and streptomycin (100 ml$^{-1}$). The device was connected, primed with cloning medium and maintained in an environmental chamber (Chamlide, LiveCell Instruments) at 37° C. and with 5% humidified $CO_2$. Two petri dishes filled with water were added in the environmental chamber to maintain the humidity. Cells were centrifuged for 5 min at 167 g and resuspended at a concentration of 2×10$^6$ cells ml$^{-1}$ in fresh cloning medium. Cells were then loaded in the microfluidic cell culture array by an approximately 1 µl min$^{-1}$ flow using an integrated micro-pump. Once the array was filled, cells were allowed to settle by gravity to the bottom of the chambers for ~3 min. If needed, this process was repeated until a desired number of single cells was obtained. After the bead immunocapture assay, the cells were cultured in a batch mode with the isolation valve kept open. Microvalves and image acquisition were controlled by custom scripts available upon request (LabVIEW, National Instruments).

Bead Immunocapture Assay

Cloning medium supplemented with 100 U ml$^{-1}$ penicillin and 100 µg ml$^{-1}$ streptomycin was used throughout the bead immunocapture assay. Polystyrene protein-A coated beads with an average diameter of 4.9 µm (ProActive® Microspheres, Bangs Laboratories) were washed at least 4 times with cloning medium by successive rounds of centrifugation at 7431 g. The beads were resuspended at a concentration of 0.1 mg beads ml$^{-1}$ and immediately loaded in the device at a flow rate of 2 µl min$^{-1}$ from a polytetrafluoroethylene tubing maintained in an upright position. Once the array was filled, the flow was stopped and the beads were allowed to settle by gravity to the bottom of the chambers, resulting in an average of 100-150 beads per chambers. Excess beads in the channels were flushed with cloning medium for 5 min at a flow rate of 2 µl min$^{-1}$. The isolation valves were then closed to sequester each chamber and the beads were incubated with cells for 2 h at 37° C. The array was then flushed with cloning medium for 15 min at a flow rate of 2 µl min$^{-1}$. A solution of 20 µg ml$^{-1}$ labeled antibody (Dylight 594-conjugated AffiniPure F(ab')$_2$ fragment of rabbit anti-human IgG (H+L) (Jackson Immunoresearch) diluted in cloning medium was first desalted by centrifugation (Amicon Ultra 0.5-ml 100K, Millipore) and then pumped into the device for 15 min at 2 µl min$^{-1}$. The fluorescent antibody was incubated for 15 min, and then washed with cloning medium for 30 min at 2 µl min$^{-1}$ before imaging.

Automated Image Acquisition

Custom scripts (LabVIEW, National Instruments), were developed to allow automated image acquisition of the array divided into 400 frames containing 4 chambers each. The location of every frame was determined by selecting the four array corners, and then extrapolating the coordinates of each frame. An alignment script (Lecault, V. et al. Nature Methods 8(7), 581-586 (2011)) was used to correct for the minor distortions in the devices that can be introduced during fabrication so as to position the chambers correctly within each frame. After loading the beads, the focus on each frame was automatically determined by taking a stack of images and identifying the focal point providing the maximum pixel standard deviation within the chambers. Following the bead immunocapture assay, a bright field image and a red fluorescent image (10 ms exposure) were taken for every frame. Frames were subsequently imaged in bright field every 30 min during cell culture.

Image Analysis Algorithms

A graphical user interface (GUI), was developed in Matlab (MathWorks) to quantify the CHO cell protein production by measuring the fluorescence intensity emitted from the beads. Since each frame contained 4 chambers, the well boundaries were first identified by blurring the bright field image and subtracting it from the original. This process enhanced areas of high spatial frequency such as the well edges. The wells were then filled and any object smaller than 1250 pixels were eliminated using a size filter. Artifacts caused by the presence of beads were corrected by dilation and the well edges were adjusted by erosion before creating a mask image of the wells. A bead mask was also created from the bright field image. The beads appeared to be much darker than the background, which allowed their segmentation using a brightness threshold. All pixels with intensity below the threshold were set to one, indicating the pixel was part of a bead, while those above the threshold were set to zero. Often, the center of the beads appeared as bright spots in the mask image due to diffraction, causing the beads to look like rings. These rings were closed and filled by a dilation step followed by erosion. Finally, any lone pixels, i.e. a single pixel with a value of one surrounded by pixels with values of zeros, were removed from the mask. A series of 6 fluorescent images containing empty wells were taken for flat-field correction. The pixel intensity at each location was averaged for the set of images and used to correct for background fluorescence. Next, the bead and well masks were combined and applied to the fluorescent image by multiplying each pixel in the mask image with the corresponding pixel in the fluorescent image. The total fluorescence intensity was calculated by summing the values of all the pixels in the resulting image. The GUI enabled the user to correct for segmentation errors when needed. The GUI also allowed the user to make a cell mask by tracing the contours of each cell. This mask was then applied to the fluorescent image to measure the intensity of each cell. The total intensity of the both the beads and each cell, along with the same values normalized by the corresponding mask area, were saved for analysis. The mean intensity of each well was calculated as the total intensity divided by the total bead area. For the selection of antibodies, stained beads were deposited on glass slides under a coverslip and imaged. The same algorithm was used to generate the bead mask from bright field images and to measure the fluorescence of the beads (no chamber mask was applicable).

Clone Recovery and Expansion

Micropipettes with a tip diameter ranging from 50-100 µm were made from glass capillaries. Prior to cell recovery, the cover layer of the chip was cut inside the area of the bath and removed. Selected clones were recovered with the micropipette using an oil microinjector (IM-9B, Narishige) and deposited in a U-shaped non tissue-culture-treated 96-well plate containing 200 µl of cloning medium supplemented with 100 U ml$^{-1}$ of penicillin and 100 mg ml$^{-1}$ of streptomycin in each well to prevent contamination from the recovery process. Clones were centrifuged for 5 min at 400 g and incubated for 9 days. Viable clones were then transferred to a 24-well plate containing 1 ml of growth medium. After 5 days of culture, the plate was centrifuged for 5 min at 400 g and the supernatant was recovered for titer analysis. The clones were then transferred to 6 ml of culture medium in 6-well plates. Once confluent, the selected clones were expanded in a 20 ml shake flask culture and banked as described above.

Batch Shake Flask Cultures

The selected clones were thawed rapidly and resuspended in 20 ml of growth medium in shake flasks. The cells were cultured and passaged until the viability reached more than 95%. The day before starting shake flask studies, the cells were seeded at a concentration of 5×10$^5$ cells ml$^{-1}$. The next day, the cells were seeded at 5×10$^5$ cells ml$^{-1}$ in 20 ml of growth medium in duplicate flasks. Cell concentration was measured with an automated cell counter (Cedex, Illumina) on days 5 and 7 for clones generated by limiting dilution and days 3, 5 and 7 for clones generated from the microfluidic platform. As well, a 1 ml-sample was taken from each flask, centrifuged at 7,341 g and the mAb concentration in the supernatant titer was measured as described below. The integral viable cell density (IVC) was calculated as follow:

$$IVC_{i+1} = 0.5 \times (C_{i-1} + C_i) \times (t_{i+1} - t_i) + IVC_i \tag{4.1}$$

where C is viable cell concentration (cell ml$^{-1}$) and t is the time in culture (days). The titer was plotted against the IVC and the slope up to day 5 was used to calculate the cell specific productivity (SPR).

Measurement of mAb Titers

Secreted mAb titers were measured by bio-layer interferometry using the Octet RED96 Analysis System (Forte Bio, Pall Life Sciences) with Protein A Biosensors (Forte Bio, Pall Life Sciences). A standard curve a from purified mAb standard of known concentration was generated with each run, ranging from 0-50 µg ml$^{-1}$ for low concentration samples and 0-500 µg ml$^{-1}$ for high concentration samples. Supernatants exceeding the dynamic range were diluted appropriately and reanalyzed.

Statistical Analysis

The error bars were calculated using the standard deviation of the mean. A two-tailed unpaired t-test with unequal variance calculated the cloning efficiency P values. The coefficients of determination ($R^2$) were based on least-square linear regressions. The coefficient of variation (CV) was calculated as the standard deviation over the mean. The theoretical Poisson distribution was calculated as follow:

$$P(x) = \frac{e^{-\mu} \mu_c^x}{x!} \tag{4.2}$$

where P(x)=probability of having a chambers containing x cells
x=number of cells per chamber
$\mu_c$=average number of cells per chamber
The antibody binding curve to the bead was calculated using the following Langmuir equation:

$$I = I_{max}\left(\frac{K \cdot c_{Ab}}{1 + K \cdot c_{Ab}}\right) \tag{4.3}$$

The constants $I_{max}$ and K were determined by a Langmuir regression using the following equation:

$$\frac{c_{Ab}}{I} = \frac{c_{Ab}}{I_{max}} + \frac{1}{K \cdot I_{max}} \tag{4.4}$$

where I=Bead fluorescence intensity
$I_{max}$=Maximum bead fluorescence intensity
K=Equilibrium constant (ml µg$^{-1}$)
$c_{Ab}$=IgG1 antibody concentration (µg ml$^{-1}$)

EXAMPLES

Example 1.1 Design of a Microfluidic Device for Suspension Cell Culture

Referring to FIG. 1, a schematic drawing of a microfluidic device according to one embodiment is shown generally at 10, with micrographs as insets. The microfluidice device 10 comprises an array of 1,600 chambers 12, each having a volume of 4.1 nL with integrated microvalves to allow precise control and exchange of media. The chambers 12 are connected by flow channels 14. Hydration lines 16 are located on each side of the array to minimize edge effects. Control lines consist of an isolation valve 18 and control lines (for example, a peristaltic pump) 20 to control cell loading and perfusion rates. Fluid can be introduced to the microfluidic device 10 through an array inlet 22 in order to access the flow channels 14 and chambers 12. Fluid may leave the device through an array outlet 24. Arrows point at single cells. The left scale bar represents 1 mm and the right scale bar represents 100 μm. Alternative embodiments could contain 1 to 50,000 chambers with volumes ranging from 1 nL to 20 μL. Alternatively, if one large chamber was connected by flow channels on top the volume may be about 5 mL. Chamber geometries exploit the properties of laminar flow to allow for immobilization of non-adherent cells without significant mechanical stress during and between medium exchanges. Various embodiments of the device also allow facile and efficient recovery of the pooled or individual contents of the chambers.

Figure 2:
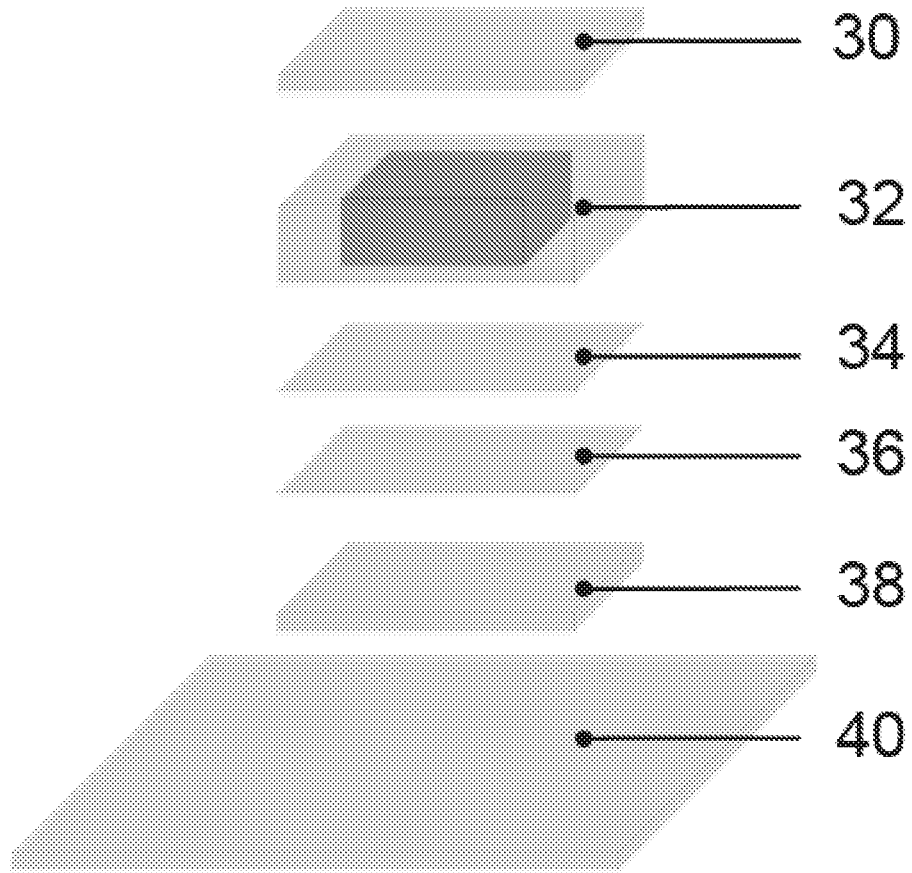
FIG. 2 is an exploded oblique view of a portion of the microfluidic device depicted in FIG. 1, showing the various layers associated with an individual microfluidic device.

In order to exploit microfabrication methods that allow dense integration of microvalves (Unger, M. A. et al. Science 288, 113-116 (2000); Duffy, D. C. et al. Analytical Chemistry 70, 4974-4984 (1998); Thorsen, T. et al. Science 298, 580-584, doi:10.1126/science.1076996 (2002)), PDMS was chosen as a preferred material. Other biocompatible polymers such as poly(methyl methacrylate) (PMMA), poly (L-lactic-coglycolic acid) (PLGA) or poly(glycerol sebacate) (PGS) PDMS could also be used for fabricating similar devices. In addition it will be appreciated by one skilled in the art that other materials such as alternative elastomers, polymers, semiconductors, or glass could be used. FIG. 2 is a schematic diagram of the layers that are assembled during the fabrication of microfluidic device. The previously mentioned problems of microfluidic devices made from PDMS were address by incorporating an integrated iso-osmotic bath 32 into the design of microfluidic device. This was achieved by fabricating the nanovolume chambers in the chamber layer (cell culture array) 38 and control structures in the control layer 36 under a 150 μm thick PDMS membrane 34 that separates them from an "iso-osmotic bath" 32 consisting of a macroscopic chamber filled with medium (~750 μL in volume) and enclosed by a gas-permeable PDMS cover layer 30 to keep the bath sterile. The cell culture layer, control layer and membrane were bound to each other by multilayer soft lithography while the membrane, iso-osmotic reservoir 32 and cover layer 30 were assembled through PDMS stamping. The PDMS chips were then bound to a glass slide 40. The integrated iso-osmotic bath 32 reservoir was filled with medium to prevent evaporation and maintain constant osmolarity inside the chambers. The iso-osmotic bath can be filled with medium and pressurized by gravity to avoid formation of air bubbles. The bath can, in some examples, be scaled proportionally to fit the area of the cell culture array, and the membrane can range from less than 1 μm to 5 mm thick depending on the application and the choice of material. The relatively high volume ratio of the osmotic bath to the culture volume (~100 times) and the lower surface to volume ratio of the osmotic bath as well as the near-saturation humidity provided by the microscope incubator, together allow a preferred osmotic strength to be maintained in each microculture for many days. Continuous exchange through the membrane also keeps PDMS-permeable medium components in equilibrium and dilutes any potentially toxic organic molecules into the large volume of the osmotic bath (Regehr, K. J. et al. Lab on a Chip 9, 2132-2139, doi:10.1039/b903043c (2009)). In an embodiment a static bath may be used. However, smaller bath volumes could also be used if the bath content was exchanged frequently. This could for instance be done using channels overlaying the chambers that are refreshed with new medium. In an embodiment illustrated in FIG. 5, the bath content can be replaced by removing a bath plug 13 and introducing fresh medium from a pump, such as syringe 19, which may connect to the array via bath inlet 17. In this embodiment, the array inlet 22 and array outlet 24 are pressurized by air and control lines 20 are connected to solenoid actuators and rest on a glass plate 40.

Example 1.2 Cell Immobilization

Various embodiments allow for perfusion of cells without disturbing cell position. This capability may be exploited for experiments requiring dynamic medium exchange or immunolabeling of the cells during or at the end of an experiment. This is particularly useful for suspension cells.

Figure 3:
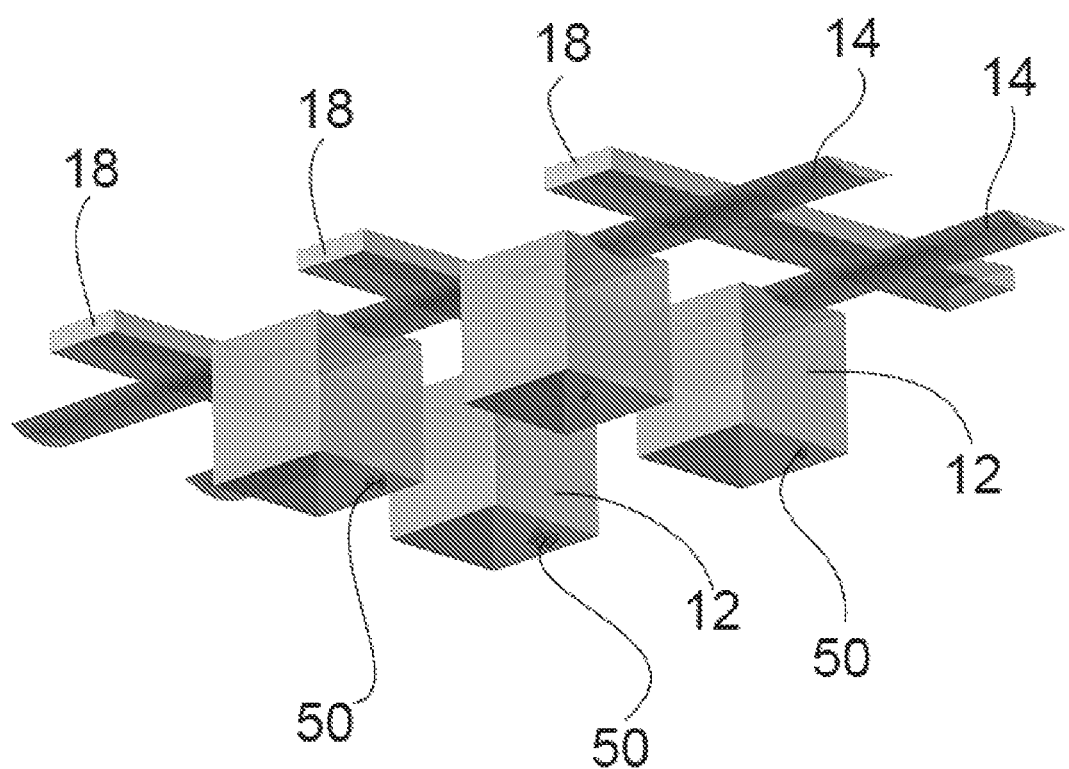
FIG. 3 is an oblique view from below of 4 microfluidic chambers depicted in FIG. 1 with associated fluid channels and control layers.

Referring to FIG. 3, one embodiment shows a microfluidic device is a non-perturbing microfluidic cell capture and retention mechanism that uses gravity to trap cells 50 in chambers with an inverted geometry with flow channels 14 running over the top and control lines 18. In the disclosed embodiment, the chambers 12 have cubic dimensions of 160 μm×160 μm×160 μm. However, larger (up to 1 mm×1 mm×1 mm) or smaller (down to 10 μm×10 μm×10 μm) could be used depending on the cell type and the intended application of the device. The chambers according to this embodiment have an aspect ratio of 1:1. However, chambers having an aspect ratio as low as 0.5 may be utilized to minimize shear forces on the cells (for example, when non-adherent cells are used).

The chamber dimensions and flow rates may be designed to ensure that a permissible maximum force (for example, shear force) is exerted on cells during medium exchange and this may be adjusted as appropriate depending on the cell types being used. If cells are completely non-adhering the chambers may be designed such that the forces do not produce any significant motion. The degree of motion considered significant will be dictated by the application for which the device is being used. For example, in an imaging application or manual cell lineage analysis it may be required that the cells move less than one diameter between image capture events which may be anywhere from seconds to several hours to days. The microfluidic cell culture arrays may exploit laminar flow to deliver the cells to the chambers and then to ensure that the cells are not disturbed by subsequent perfusion. During medium refreshment or cell loading the volume expansion from the flow channels (≤13 μm×100 μm) to the chambers (160 μm×160 μm) creates a large reduction in velocity that drops off quickly to very low levels at the bottom of the culture chambers (e.g. FIGS. 3 and 4). In alternative embodiments where the depth of the chamber (i.e. length of the shortest distance between the retaining position and first region) was 80 μm (y) and the length of the first region was 160 μm (x), it was observed that the velocity of the perfusion fluid at the retaining position was such that the cells at the retaining position were being moved by the flow of perfusion fluid. The flow channel could be positioned at different heights within the chamber, as long as the bottom of the chamber is far enough from the channel so that the velocity at the bottom of the well is low enough to maintain cells immobilized by gravity. In the tested embodiment, the suspended cells were first loaded into the array using the microfabricated peristaltic pump 20 (FIG. 1) at an overall flow rate of 1 μL/min. This corresponds to a maximum velocity of ~1 mm/sec and shear stresses of <0.3 Pa (not shown), which is well below levels that elicit physiological responses (Ma, N. N. et al. Biotechnology and Bioengineering 80, 428-437, doi:10.1002/bit.10387 (2002)). Syringe pumps, manual, gravity or pneumatic pressurization could be used as alternatives to the integrated micropump to control the flow rates. Both pulsatile and continuous flows may be used to ensure minimal cell motion during medium exchange. During loading, cells essentially follow the streamlines at the top of the chambers, and thus pass through the array without having the time to settle in the chambers. Once the array is filled, the flow is stopped, and this then allows the cells to settle into the bottom of the chambers where they are sequestered from the flow streamlines. When necessary, cells may be concentrated on the chip by repeating this loading process in a step-wise fashion. Typical loading efficiencies of 10-30% of chambers may be achieved for clonal analyses (i.e., approximately 160-480 single cells per device). A person of skill would be able to direct the desired number of cells to a chamber by adjusting cell concentrations, flow rates, flow times, etc. Cell trapping cups could be integrated in the flow channels to increase the seeding efficiency in other embodiments. Additionally, other trapping mechanisms, including dielectric forces, magnetic forces, and optical forces could be used as appropriate. Alternatively, valve structures could be designed to deterministically place cells in chambers.

In the preferred embodiment, medium exchange through the array at a flow rate of 2 µL/min, results in a maximum shear stress <$10^{-4}$ Pa at a distance of one cell diameter from the chamber bottom (not shown). Direct observation of cells in arrays being perfused at this rate to exchange media or for immunolabeling showed that the positions of the cells remained undisturbed (FIG. 9A), thereby validating the use of these strategies while monitoring the growth of individual clones. This capability is demonstrated in FIG. 9B where frequent imaging (<5 min) was used to track the progeny of three single HSCs and build cell lineage trees over 60 hours while replacing the cell culture media every 6 hours (see FIG. 9C). The frequency of image acquisition can be adjusted based on the number of wells being observed and the time required to capture images of all the chambers.

In an embodiment described herein, the small chamber length-scale allows for efficient exchange of nutrients, growth factors and metabolites by a combination of convection and diffusion. For small molecules (D~$10^{-9}$ m$^2$/sec) or proteins (D~$10^{10}$ m$^2$/sec), this diffusion time is approximated by $\tau \sim x^2/D$ where x is one half the chamber height, giving exchange times of 10 sec or 100 sec, respectively. This is significantly shorter than our medium perfusion protocols that have refresh times of 10 minutes.

Recovery of Cells Post-Culture

Cell recovery is often required to enable functional assays to be performed on the progeny of the input cells, or to select cells of interest for larger scale culture. A method to recover defined clonal populations is therefore a critical requirement for many applications of microfluidic cultures.

Figure 4:
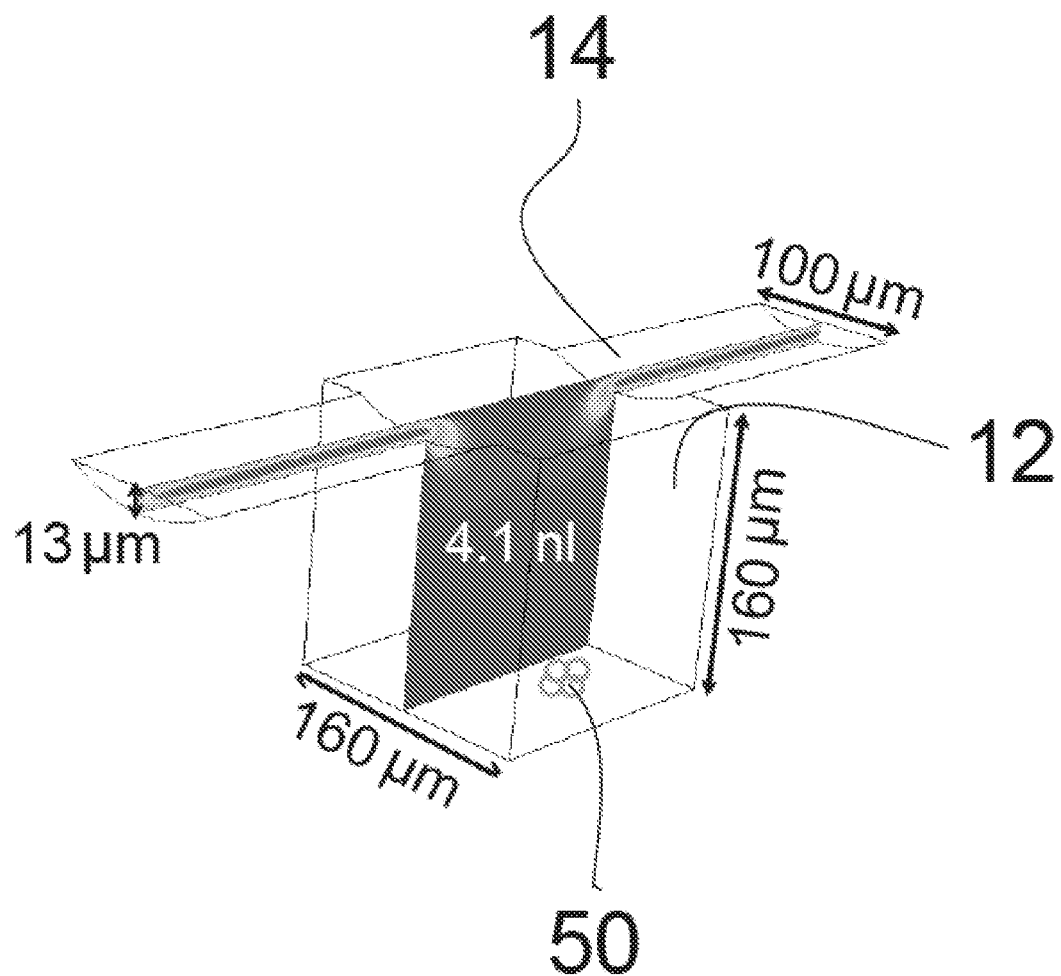
FIG. 4 is a cross-sectional view of a chamber and a channel of the microfluidic device depicted in FIG. 1, showing the dimensions and volume of the chamber, and a depiction of fluid speed in the control layer and chamber while the chamber is being perfused.

FIG. 4 shows a numerical simulation of the flow profile through a culture chamber of an embodiment. With a flow rate of 0.0625 µl/min through the flow channel, the velocity in mm s$^{-1}$ for the flow channel 14 is 2.4 mm s$^{-1}$ at the center of the flow channel, with a gradual decrease at the edges of the flow channel to about 1.0-1.2 mm s$^{-1}$. The sudden expansion when the fluid moves from the flow channel to the chamber creates a velocity drop, and the velocity in the cell retaining region is reduced to less than 50 µm/s. The velocity in mm s$^{-1}$ for the culture chamber 12 ranges from about 1.6 to about 0.4 mm s$^{-1}$ immediately adjacent the inlet and outlet (see bright flares) of the flow channel and the remainder of the culture chamber 12 ranges from about 0.4 to about 0.0 mm s$^{-1}$. The culture chamber 12 dimensions (160 µm×160 µm), flow channel 14 dimensions (100 µm×13 µm) and culture chamber 12 volume (4.1 nl) are also shown. The modeling predicts minimal flow rates at the bottom ⅚ of the chamber. In accordance with embodiments, the gravitational forces on the cells is greater than hydrodynamic forces and cells remain in the cell retaining region while the perfusion fluid exits the chamber through the flow channel outlet. Similarly, modeling of fluid velocity during cell loading (modeled for a total flow rate of 1 µL/min) suggests that a maximum velocity in the flow channels 14 does not exceed $1.2 \times 10^{-3}$ m/s and that the maximum velocity in the majority of the chamber 12 is at or near 0 m/s (not shown) during cell loading. When the flow is stopped, cells settle down in the chamber 12 by gravity to the cell retaining region. Additionally, modeling of the sheer stress (Pa) on the channel walls 14 suggests during cell loading, the flow rate of 0.03 µl/min through the flow channel results in a maximum shear stress exerted on the cells is 0.3 Pa next to the channel wall (not shown). Similarly, modeling of sheer stress on cells within a chamber 12 during media exchange (i.e. perfusion) at a flow rate of 0.0625 µl/min through the flow channel suggests that the maximum shear exerted on the cells while at the bottom of the chamber (i.e. cell retaining region) during medium exchange (based on a total flow rate of 2 µl min$^{-1}$) does not exceed $3.1 \times 10^{-4}$ Pa and would be about 0.0004 Pa in the middle of the cell retaining region.

Embodiments of the chamber design and microfluidic apparatus described also allow for facile recovery of cells from the entire array by simply inverting the device, causing the cells to settle into the higher-flow rate regions of the chambers (as shown in FIG. 4) and then recovering the pooled population by flushing back through the input port. This recovery method is simple and efficient, allowing for the harvesting of approximately 90% of cells with losses mainly attributable to the nonspecific adherence of cells on the surface of chambers. However, when selective recovery of the contents of specific individual wells is desired, the layer of PDMS covering the osmotic bath can first be removed and a sterile micropipette then used to pierce the membrane over any selected chamber followed by aspiration of its contents (not shown). This method was found to be remarkably reliable and easy, allowing more than 90% of the cells in each well harvested to be recovered as determined by direct cell counts before and after (FIGS. 9A and 9B). It can be performed either manually of automatically if greater throughput is needed. Furthermore, aspiration through a capillary (controlled with micron precision) or optical forces could be used to recover select cells. Alternatively, cells could be labeled individually using optical means while in the device, recovered together by flowing out of the device, and then subsequently identified using the marker. One such marker may be a fluorophore that changes spectral properties when illuminated by a light source such as a focused laser or other light source capable of selectively labeling cells.

Example 1.3 Culture of Hematopoietic Cells

Culture of Single Hematopoietic Cells in Microfluidic Cell Culture Arrays.

Figure 10:
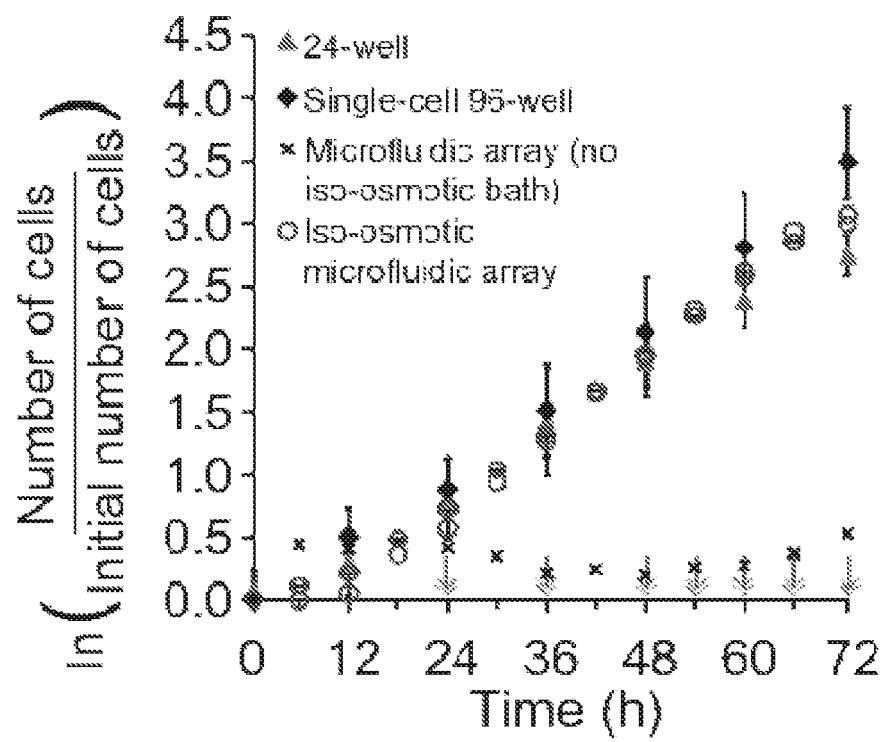
FIG. 10 is a graph comparing the of average growth rates of ND13 cells in 24-well dish culture, single cell 96-well culture, a microfluidic device as described herein with and without an iso-osmotic reservoir (arrows show growth medium exchange).

We tested the applicability of this microfluidic device to the study primitive hematopoietic cells. We first examined the growth of a preleukemic murine cells created by geneti cally engineering primitive adult mouse bone marrow cells to express a NUP98-HOXD13 (ND13) fusion gene[9,10]. Matched cultures of these "ND13" cells were set up in 24-well plates seeded at 150,000 cells/mL, 96-well plates seeded with single cells, and microfluidic cell culture arrays with or without the integrated iso-osmotic bath. In the presence of the iso-osmotic bath, the population doubling time averaged over all chambers loaded with single cells faithfully reproduced the bulk growth rate seen in the culture plates, indicating comparable conditions had been achieved. In addition, the average rates of expansion of the clones generated in the microfluidic chambers were equivalent to the average growth rates obtained in the 200 µl 96-well cultures (FIG. 10). However, in devices that lacked the iso-osmotic bath, cell division and survival was severely compromised (e.g. FIG. 10), in spite of humidity control in the microscope incubator and the initiation of medium exchanges 24 hours after starting the experiment, indicating that permeation effects occur within hours, which can in turn affect cell growth. In cases where other materials are used that have reduced transport properties the osmotic bath may not be required. Alternatively, the use of perfusion with sufficient frequency may be used to reduce the need for the osmotic bath.

Figure 11:
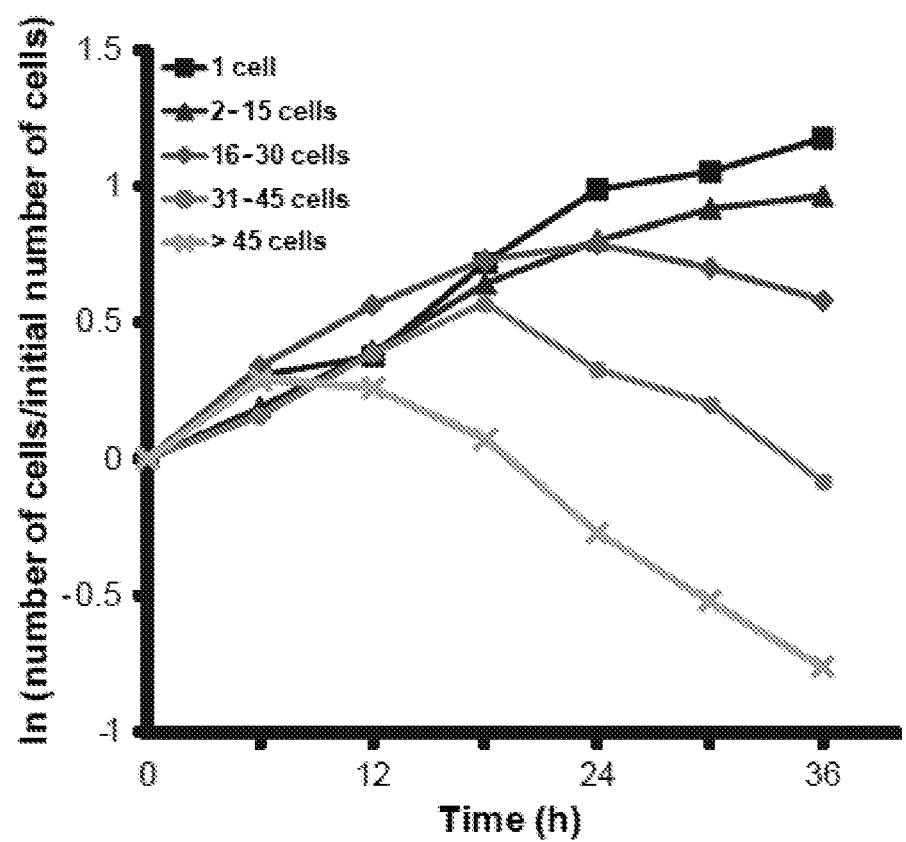
FIG. 11 is a graph of cell concentration (1 cell, 2-15 cells, 16-30 cells, 31-45 cells, and >45 cells) over time for various seeding densities grown in a microfluidic device according to an embodiment, but with no medium exchange and no iso-osmotic bath. This Figure shows a strong inverse correlation with the initial number of cells in each chamber.

A single cell in a 4.1 nL isolated chamber is at an effective concentration ~$2.5 \times 10^5$ cells/mL. At confluence, a chamber contains ~150 cells; i.e., a concentration of ~$4 \times 10^7$ cells/mL. This concentration greatly exceeds the limits of conventional batch cultures. Thus, it is not surprising that cultures exhibited a strongly inverse correlation between the number of cells inoculated into each isolated chamber and the duration of cell growth, in the absence of the iso-osmotic bath batch mode (FIG. 11). This underscores the importance of medium exchange to sustain the continued optimal growth of these cells in nanolitre-volume chambers, and the need to progressively increase the frequency of medium exchange as the number of cells in each culture increases. For the single ND13 cell cultures, we found that medium exchanges at 24, 36, 48, 54, 60, 66 and 72 hours were sufficient to avoid nutrient limitations and the build-up of growth-inhibiting metabolites, although this feeding pattern can be adjusted based on cell types, seeding density and required nutrient concentrations.

Example 1.4 Assessment of Growth Heterogeneity by Defined Cell Populations

Figure 12A:
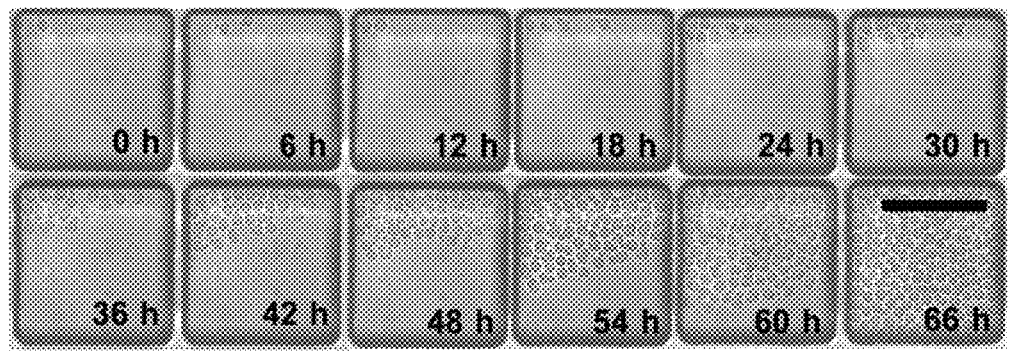
FIG. 12A are time-lapse images of clonal expansion in a chamber of a microfluidic device according to an embodiment (at 0 hr and at 6 hr intervals thereafter until 66 hrs.).
Figure 12B:
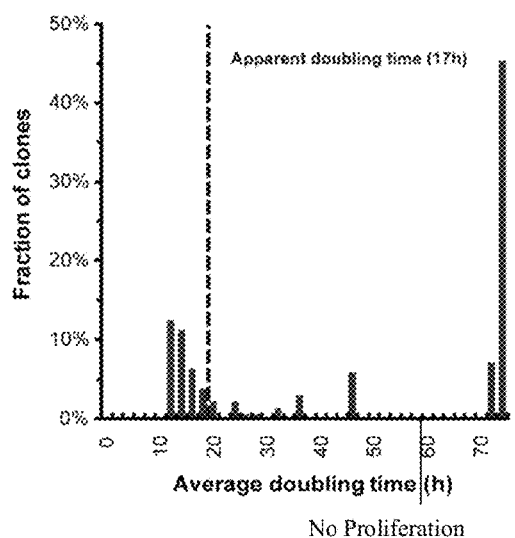
FIG. 12B is a histogram depicting distribution of average doubling times of clonal ND13 cultures up to 72 hrs. in a microfluidic device according to an embodiment, showing that the cells growth rates are highly heterogeneous, whereby only a small fraction of fast growing cells contributed to the overall growth rate, while 52% of the cells did not give rise to colonies (i.e. cells marked 'no proliferation' (52%) did not divide during this period or died).
Figure 12C:
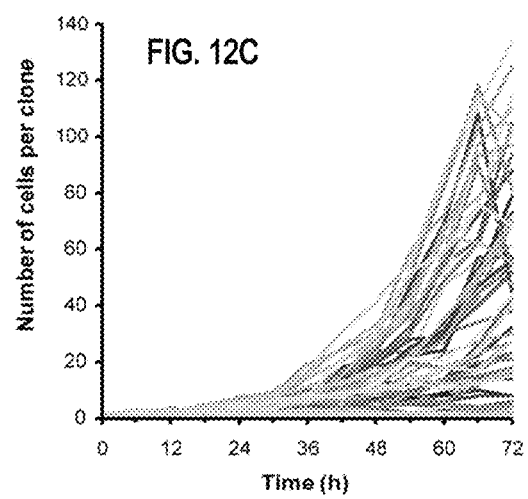
FIG. 12C is a graph depicting the proliferation profile of individual clones over time (as counted by automated image analysis for individual ND13 cells) in a microfluidic device according to an embodiment, also showing highly variable growth rates.
Figure 21:
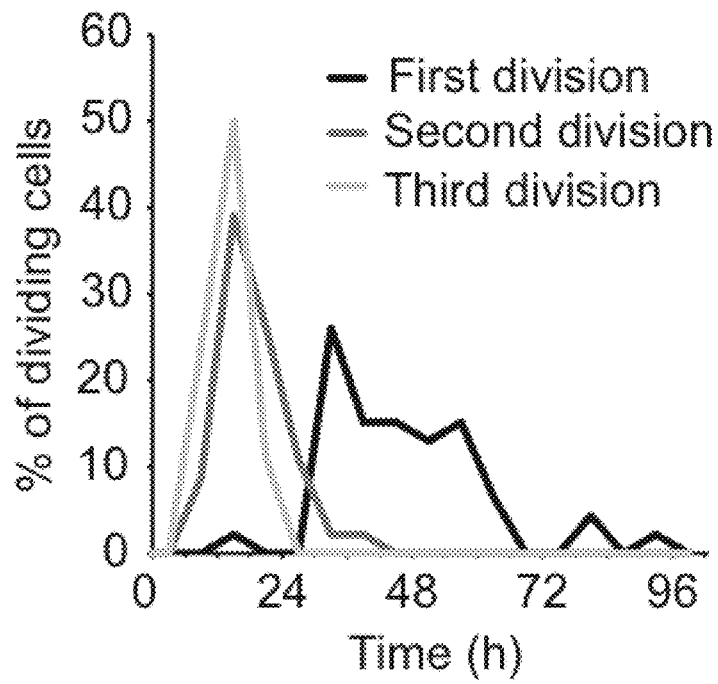
FIG. 21 shows a percentage of dividing cells over time for mouse HSCs cultured in the microfluidic array under high SF concentration (300 ng ml-1), where single cells were imaged every 4 min, and the times for the first, second and third divisions were identified by manual inspections of the videos for 46 cells.

Time-lapse imaging and automated image analysis was used to generate individual growth curves for 243 single ND13 cells over a period of 72 hours (a sample is shown in FIG. 12A). After that time, the fastest growing clones became multilayered and too large for further tracking by image analysis. Although the average doubling time for all cells was 16.8 hours, we observed substantial heterogeneity in the growth characteristics of individual clones. 52% of the input cells either did not divide or produced progeny that died before the end of the experiment. This widespread death was offset by the rapid proliferation of other cells that divided as frequently as every 12 hours, but with large variability between clones (FIGS. 12B and 12C). Such variable clone size distribution was also observed for ND13 cells generating clones in the 96 well plate cultures (not shown). Furthermore, similar distributions of doubling times were found for both ND13 cells grown in microfluidic arrays and multiwell macro plate controls (not shown). A similar experiment was conducted using normal primary HSCs. Microfluidic culture of freshly isolated CD45+EPCR+ CD48−CD150+ (E-SLAM) adult mouse bone marrow cells, which are approximately 50% pure HSCs (Schroeder, T. Cell Stem Cell 1, 479-481 (2007)), over 5 days showed that the kinetics of three successive divisions were comparable to those obtained in macroscale cultures (Dykstra, B. et al. Proc. Natl. Acad. Sci. USA 103, 8185-8190 (2006); Kent, D. G. et al. Blood 112, 560-567 (2008)) (see FIG. 21).

Figure 18:
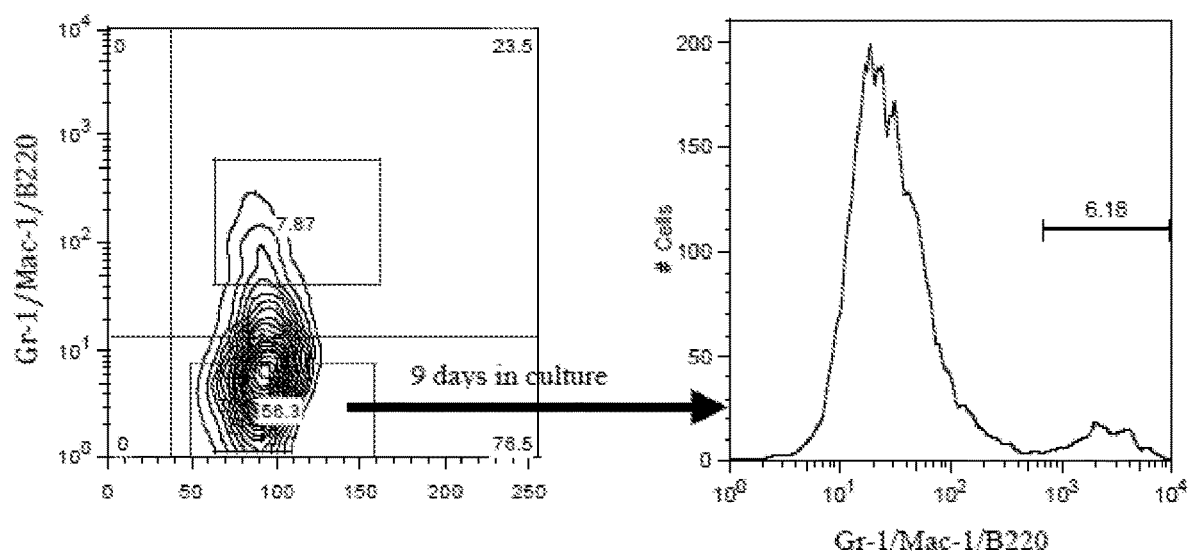
FIG. 18 shows a mature myeloid population derived from lineage negative ND13 cells, where the ND13 cells were stained for Gr-1, Mac-1 and B220 and sorted by flow cytometry and the lin⁻ fraction was cultured for 9 days and gave rise to a new lint population.

To further investigate this heterogeneity, we stained ND13 cells for the lineage (lin) markers (Gr-1, Mac-1, and B-220) and compared the clonal growth kinetics of single differentiated (lin$^+$) and primitive (lin$^-$) cells. We opted for lineage staining to characterize cells in this particular experiment but antibody staining, enzymatic assays, dyes, RT-qPCR, sequencing, functional assays, or bead capture could also be used to characterize the cells. After staining, cells were introduced into the device and imaged every 5 minutes for 72 hours. We used the perfusion capabilities to perform a second lineage staining on clones at the end of the experiment without disturbing colony locations. This experiment showed that most of the lin$^+$ cells did not produce colonies (FIG. 13A), which replicated the failure of lin$^+$ cells to form colonies in 96-well cultures. In contrast, the single lin$^-$ cells produced clones efficiently but of different sizes and phenotypes (FIG. 13B). Some of the lin$^-$ cells gave rise to exclusively lint or lin$^-$ clones. In other cases, the clones were of mixed phenotypes (FIG. 13C). This suggests that ND13 cells maintain a lin$^-$ clonogenic progenitor population that can produce both more of themselves (i.e., lin$^-$ cells) as well as more mature non-clonogenic lint cells. Further support for this model was obtained by isolating lin$^-$ cells by FACS, expanding them in macroscale cultures, and then demonstrating after 12 days that a new lint population had again been produced (FIG. 18).

In a different experiment, unseparated ND13 cells were cultured in the microfluidic device for 72 hours and then approximately 720 cells from 5 chambers (corresponding to 11 starting cell equivalents) recovered (FIG. 13D) and plated into triplicate colony-forming cell assays in methylcellulose-containing medium. Parallel methylcellulose assays were set up with the progeny of 11 starting cell equivalents generated in standard control cultures. The number of colonies obtained from each source was again similar, further demonstrating the equivalence of the microfluidic device in supporting ND13 progenitor expansion (FIG. 13D).

Example 1.5 Expansion of HSCs

Figure 14A:
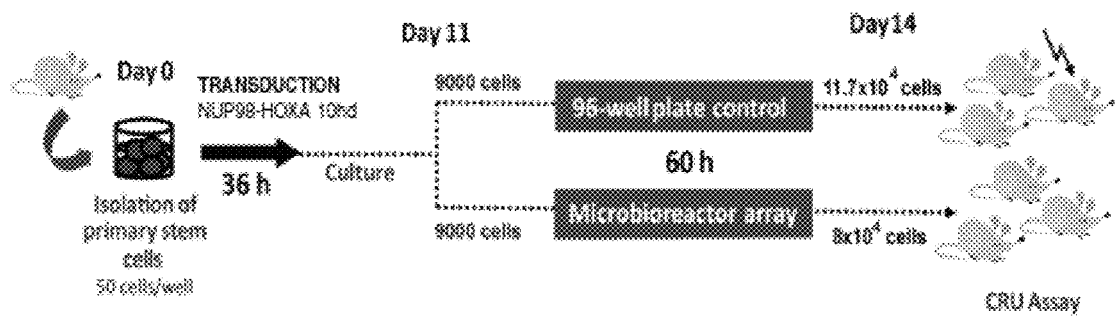
FIG. 14A is a schematic diagram of a study to compare primary hematopoietic stem cells (HSC) activity in NUP98-HOXA10hd (NA10dh)-transduced hematopoietic populations cultured in a microfluidic device according to an embodiment as compared to hematopoietic populations cultured in a macroscale 96-well plate as compared by competitive repopulating cell (CRU) assay.
Figure 14B:
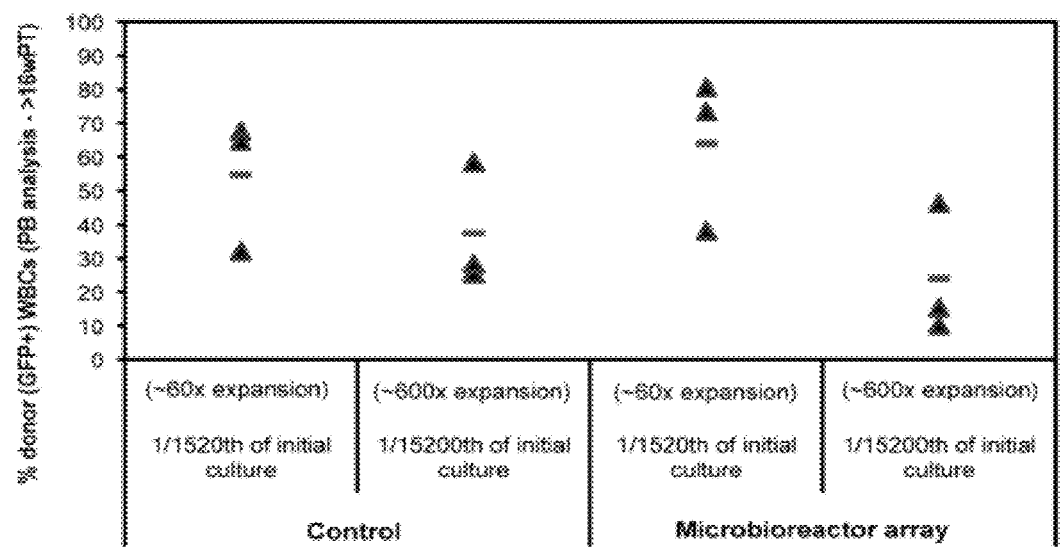
FIG. 14B shows a comparison of macroscale 96-well plate cultured cells (control) with microarray cultured cells, whereby NUP98-HOXA10hd cells maintained functional HSC activity after being cultured in the microfluidic array according to an embodiment and were able to reconstitute the blood-forming system of lethally irradiated mice.

To test the suitability of these microfluidic cell culture arrays to support HSC self-renewal divisions, we examined the growth of mouse bone marrow cells transduced with a NUP98-HOXA10homeodomain (NA10hd) fusion gene, which potently stimulates their ability to expand in vitro without any signs of leukemic transformation (Ohta, H. et al. Experimental Hematology 35, 817-830, doi:10.1016/j.exphem.2007.02.012 (2007); and Pineault, N. et al. Molecular and Cellular Biology 24, 1907-1917 (2004)). To obtain these cells, we first isolated a highly purified population of primary HSCs (with a CD45$^+$CD48$^-$EPCR$^+$CD150$^+$ phenotype), and then transduced these cells with a NA10hd-encoding retroviral vector. The transduced cells were then expanded for 11 days in a macroscale culture. At the end of this period, replicate aliquots were then transferred either to the microfluidic array or a control macroscale vessel and cultured for an additional 60 hours. The cells from each of these latter cultures were then recovered and decreasing fractions of the same starting equivalent number injected into groups of 6 mice each. The total number of cells obtained from the chip and the control macrocultures were similar (FIG. 14A). All mice showed similar reconstitution levels by the transplanted cells for >16 weeks post-transplant, indicative of an overall stem cell expansion of more than 600-fold compared to the stem cell content of the purified cells initially transduced (FIG. 14B). The mice repopulated with cells from the microfluidic array also showed reconstitution of both their myeloid and lymphoid compartments (FIG. 15A). Notably, the cultured NA10 HSC population contained a greater proportion of fast growing cells compared to the ND13 cells (FIG. 12B), consistent with the lack of highly mature cells in the NA10 population.

Example 1.6 HSC Response to Temporally Varied SF Stimulation

Figure 16:
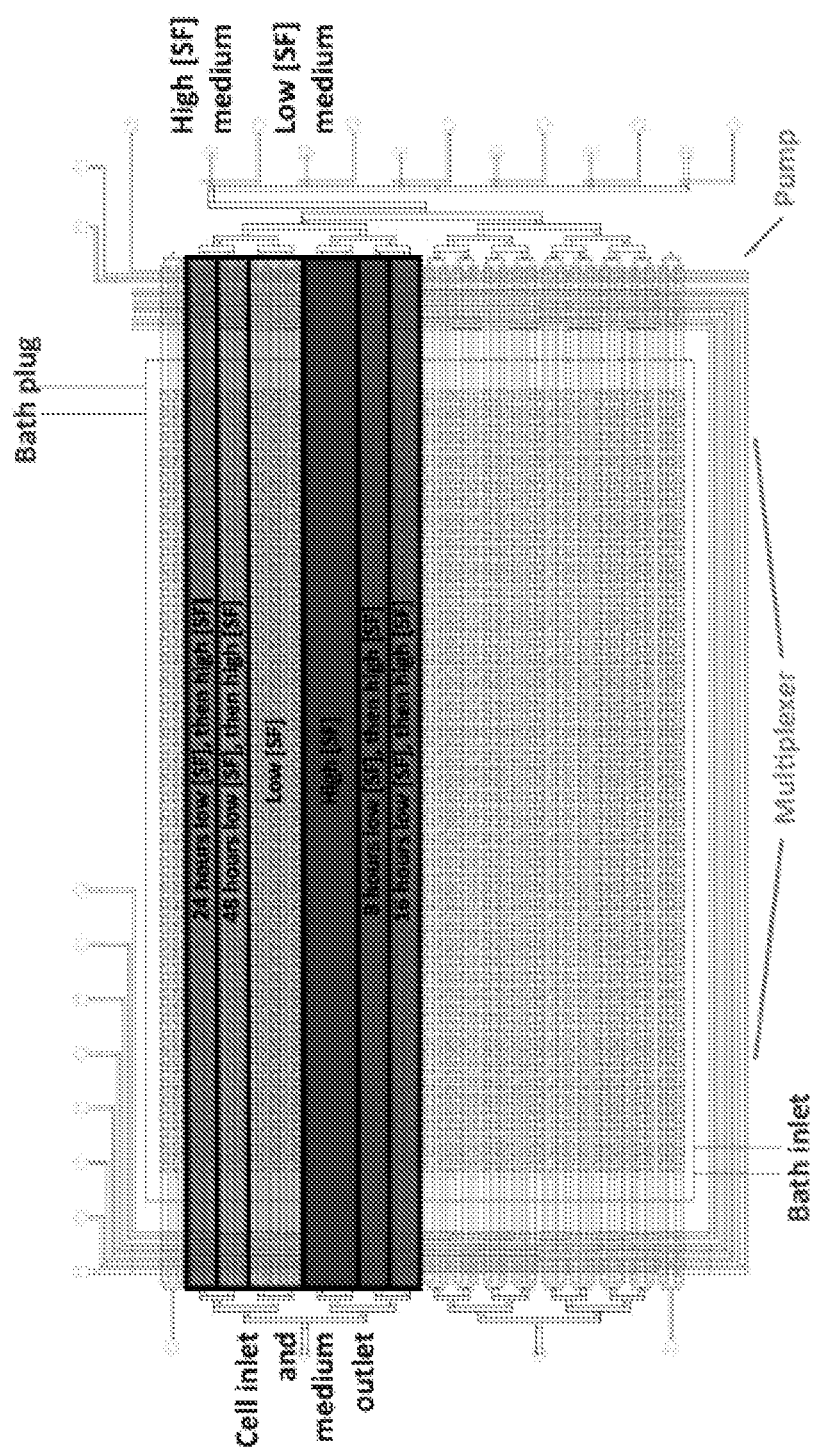
FIG. 16 shows a microfluidic cell culture array for temporal stimulation and parallelization of experiments, wherein the microfluidic cell culture array contains 6,144 chambers and can support up to 8 different conditions simultaneously, but only the top half of the array was used to study murine HSCs due to the relatively small cell numbers and 6 different conditions were distributed across the array as shown.

Previous work has shown that in vitro exposure of HSCs to low concentrations of steel factor (SF) (1 ng ml$^{-1}$) leads to rapid loss of HSC function, delayed proliferation and increased death compared to culture in higher concentrations (300 ng ml$^{-1}$) (Kent 2008 supra). However, the reversibility of the effect of low SF concentrations on HSC survival and proliferation is not known. To address this question microfluidic system as described herein were used to test how long quiescent adult HSCs could be exposed to a low SF concentration before rescue by exposure to a high concentration was no longer possible. An enlarged microfluidic device consisting of 6,144 individual chambers and additional inlets and flow control valves to enable parallel studies with many temporally varied conditions was used (FIG. 16). Six different conditions in which primary mouse HSCs (E-SLAM isolates of adult mouse bone marrow) were exposed to 20 ng ml$^{-1}$ of interleukin-11 (IL-11) plus either 1 ng ml$^{-1}$ SF for the first 8, 16, 24 or 48 h followed by 300 ng ml$^{-1}$ SF for the remainder of the experiment, or constant SF concentrations of 1 ng ml$^{-1}$ or 300 ng ml$^{-1}$ for the entire experiment (not shown). The experiment was repeated twice yielding 5 days of imaging data for a total of 769 single E-SLAM cells cultured in the device. By day 5, the fastest growing clones reached confluence, and we could no longer quantitatively monitor their size. Growth rates of all clones were compared to the results for the constant high SF concentration. As a control, the same cells were grown in conventional macrocultures in 20 ng ml$^{-1}$ IL-11 plus either 1 ng ml$^{-1}$ or 300 ng ml$^{-1}$ SF and these yielded the same growth kinetics as in the microfluidic device. Compared to the high [SF] condition, a Cox proportional hazard analysis of the cell survival over time, defined as the fraction of starting cells that remained viable or gave rise to clones, showed no significant difference (P>0.1) in survival when the cells were rescued from 1 ng ml$^{-1}$ SF exposure within the first 16 h of culture (Table 1).

TABLE 1

| Cox proportional hazard analysis of mouse HSC survival | | | |
|---|---|---|---|
| Condition | n | Relative risk (95% CI) | P value |
| High [SF] (300 ng ml-1) | 294 | 1.00 | — |
| 8 h in low [SF] | 107 | 0.82 (0.64-1.06) | 0.13 |
| 16 h in low [SF] | 76 | 1.03 (0.78-1.36) | 0.84 |
| 24 h in low [SF] | 24 | 1.27 (0.81-1.99) | 0.29 |
| 48 h in low [SF] | 79 | 1.78 (1.37-2.31) | <0.0001 |
| Low [SF] (1 ng ml-1) | 189 | 1.53 (1.25-1.86) | <0.0001 |

CI, confidence interval.
—, not applicable.
Relative risks and P values were calculated based on the high [SF] condition.

Figure 6:
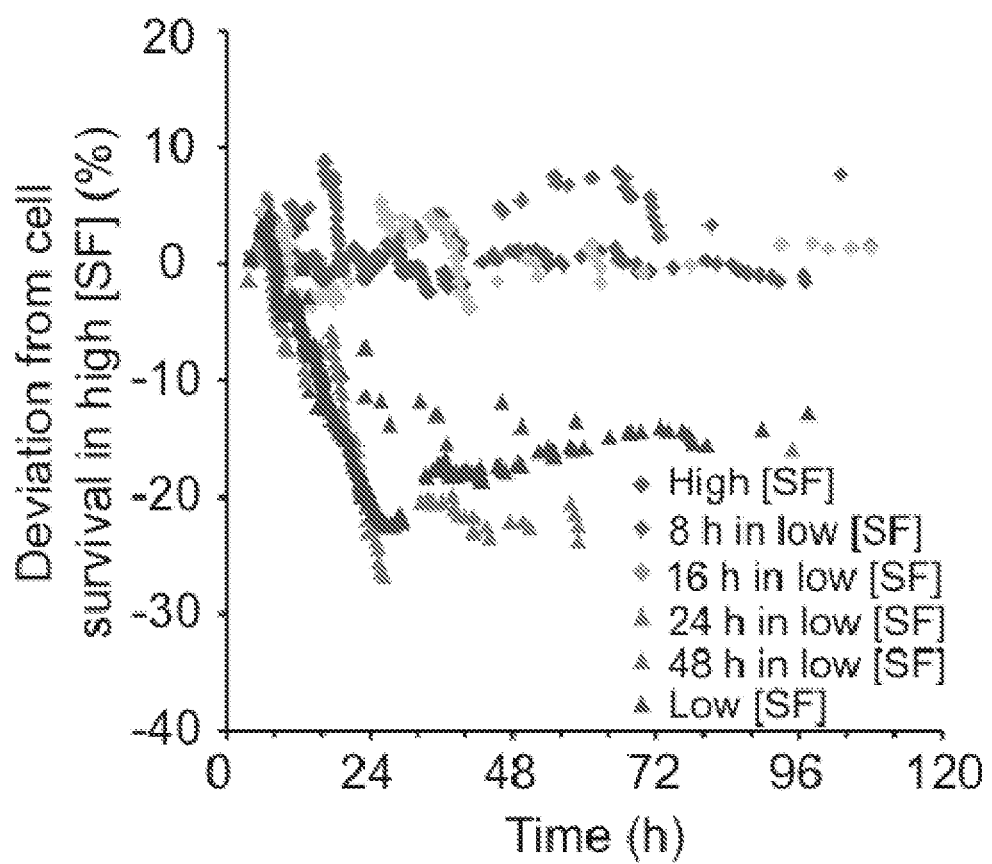
FIG. 6 shows differences in cell survival during microfluidic culture in the indicated conditions compared to the high [SF] condition, wherein the cells were imaged every 12 min, and survival curves were normalized to a third-order polynomial fit for the high [SF] conditions.
Figure 7:
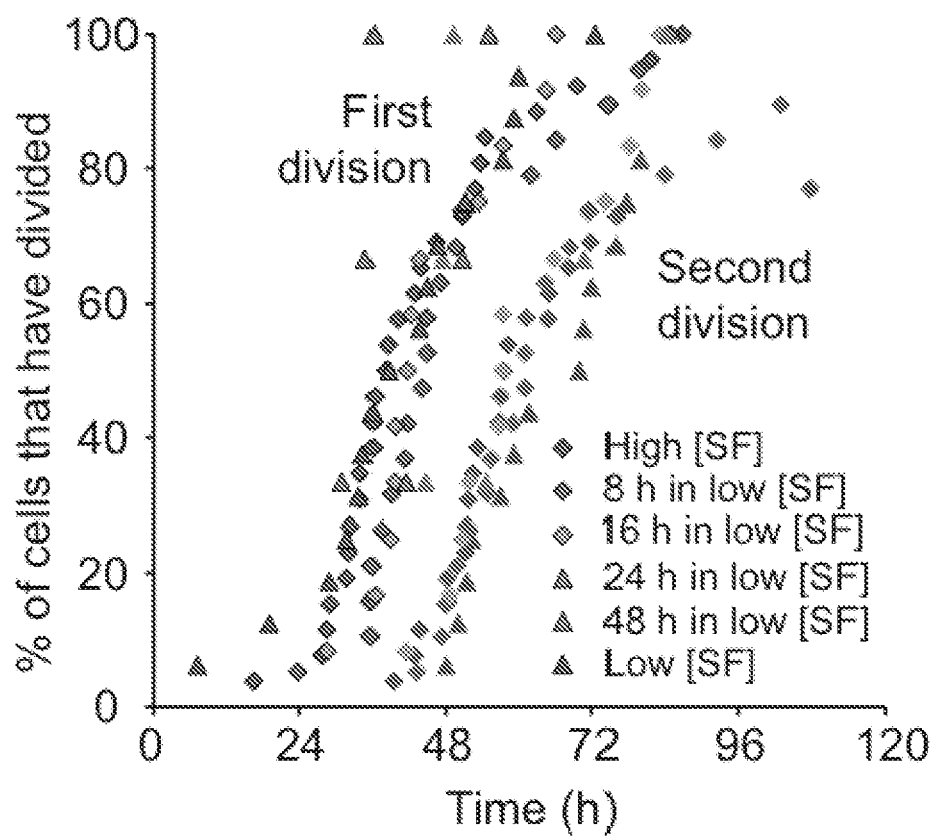
FIG. 7 shows cumulative division kinetics of primary HSCs that are cycling (excluding dead and quiescent cells) in the indicated in vitro conditions for the first and second divisions.
Figure 8:
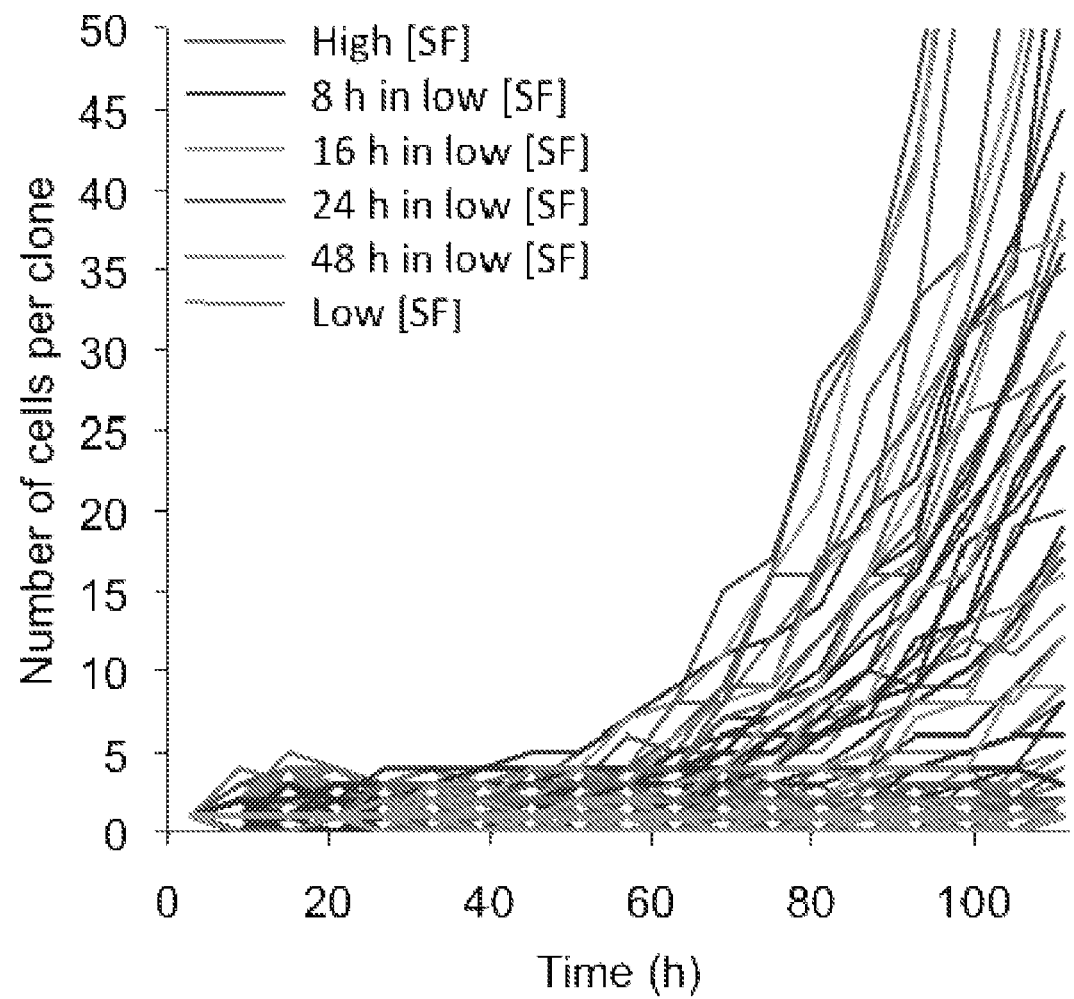
FIG. 8 shows individual growth curves of primary murine HSCs under different Steel factor (SF) exposure conditions, where the growth curves were generated using the enhanced bifocal image analysis algorithm and the analysis was started after 21 hours to allow small quiescent cells to reach a suitable size for detection by image analysis.

Prolonged initial exposure to 1 ng ml$^{-1}$ SF led to a rapid decrease in viability between 16 and 24 h, and after that time, the cells could not be rescued by exposure to 300 ng ml$^{-1}$ SF (FIG. 6). Most dividing cells completed a first mitosis between 24 and 60 h of culture for all conditions, and the SF concentration did not affect the cell division kinetics (FIG. 7 and FIG. 8). Analysis of the second division showed comparable kinetics, with more than 80% of the clones remaining viable after a first division regardless of the SF concentration to which they had been initially exposed. Thus, although a high SF concentration influenced the viability of HSCs as they exited quiescence, it did not directly impact the subsequent division kinetics of cells that complete a first division.

Microfluidic technology brings the potential of chemical control of the culture medium in combination with single cell imaging to create new opportunities for the high throughput analysis of clonogenic cell responses to varying extracellular cues. The embodiments described herein introduce several design features which enable experiments with heterogeneous populations of suspension cells, even those that have stringent medium requirements. Some particular embodiments may include the incorporation of an enclosed and sterile iso-osmotic reservoir to control unwanted permeation and dehydration effects separated by a membrane from high aspect ratio wells to contain and immobilize non-adherent test cells during perfusion, and the use of a reverse perfusion strategy or selective aspiration to recover all cells or selected clones.

Using aspects and embodiments described herein, it is demonstrated herein that successful culture of cytokine-dependent hematopoietic cells is possible with expansion and enhanced HSC function. Maintaining equilibrium with the macroscopic volume of the osmotic bath allows for high-throughput microfluidic single cell cultures in volumes that are 4 orders of magnitude smaller than conventional macroscale cultures. A single cell isolated in a 4 nL chamber is at an effective density of 2.5×10$^5$/mL, thus making possible the investigation of autocrine signaling by isolated cells, with the potential of increasing plating efficiency for cell types that might otherwise require conditioned medium or a high cell density. Co-culture of different cell types at limiting dilution could further be used to investigate the effect of cell-cell influences through secreted factors. It is also worth noting that with sufficient medium exchange, we were able to maintain cell proliferation to densities that resulted in the creation of multiple layers of cells. This ability to maintain high-density cultures offers new opportunities for studying the effects of cell concentration on cell behavior.

Various embodiments also provide flexibility to monitor the clonal growth (or other responses) of single non-adherent cells over time in the presence of dynamic changes in medium conditions by combined time-lapse imaging with programmed medium exchanges that do not disturb the spatial position of each cell or colony. It has been shown, for instance, that exposure of HSC in vitro to sub-optimal steel factor concentrations can induce their differentiation within 16 hours even prior to their entry into the cell cycle (Kent, D. G. et al. Blood 112, 560-567, doi:10.1182/blood-2007-10-117820 (2008)). Thus, it is relevant to anticipate that other schedules of growth factor delivery can further modulate HSC fate decisions. The fully programmable system for both perfusion and image acquisition allows automated and dynamic temporal operation over the entire duration of the culture experiment, thereby providing a mean to analyze the evolution of clonal cultures in time rather than measuring only end-point outcomes. In addition, the ability to replace the culture medium is a key feature to avoid nutrient limitations that occur in longer-term experiments in which even a small amount of proliferation causes a significant increase in the local cell concentration. Imaging the cellular contents of 1,600 chambers requires less than 5 minutes allowing the changes to be monitored at high temporal resolution. When coupled with emerging image processing tools for identifying new morphological phenotypes (Cohen, A. R. et al. Nat Meth 7, 213-218 (2010)) and for tracking different cell divisions identified by specific markers or fluorescent reporters (Eilken, H. M. et al. Nature 457, 896-900 (2009); and Satyanarayana, S. et al. Journal of Microelectromechanical Systems 14, 392-399 (2005)), the combined advantages of high throughput and medium control will now allow previously impossible large-scale studies of fate-choices by rare cell types.

The growth kinetics analysis performed on the ND13 population yielded findings that can only be revealed from clonal analyses. The scale of the perfusion microfluidic cell culture array described here was purposefully optimized for the study of small numbers of hematopoietic cells, but can be readily modified to give designs with other features; e.g. more or larger chambers. Situations where only a small fraction of the cells are responsible for the long-term maintenance of the overall population are not exclusive to the hematopoietic system. The technology is highly suitable for adaptation to other cell types/organisms and other applications such as drug-response screens, culture optimization, clone selection, recombinant protein production and cell characterization. Various aspects and embodiments described herein are also ideally suited to controlled experiments investigating the interaction of two or more cell types. The extended use of microfluidic systems coupled with live-cell microscopy thus offers great promise for many applications of scientific investigation in biology and medicine.

Example 2 Clonal Cell Growth and Selection

Example 2.1 Microfluidic Secretion Assay and Clonal Expansion

Figure 22:
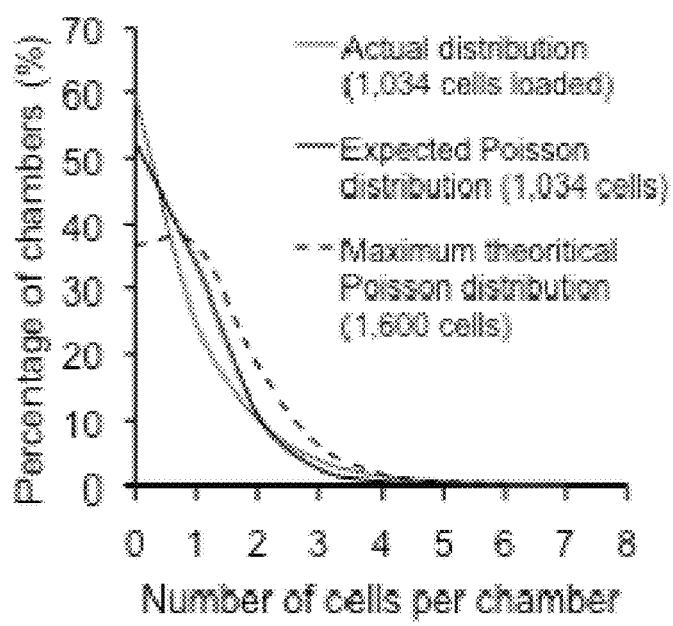
FIG. 22 shows typical seeding density of around 25% of the 1,600 chambers contained single cells at a loading concentration of $2 \times 10^6$ cells ml$^{-1}$ (total: 1,034 cells), close to the expected Poisson distribution and the theoretical maximum of a Poisson distribution for an average of 1 cell per well (total: 1,600 cells).
Figures 23A, 23B, 23C, 23D, 23E, 23F, 23G:
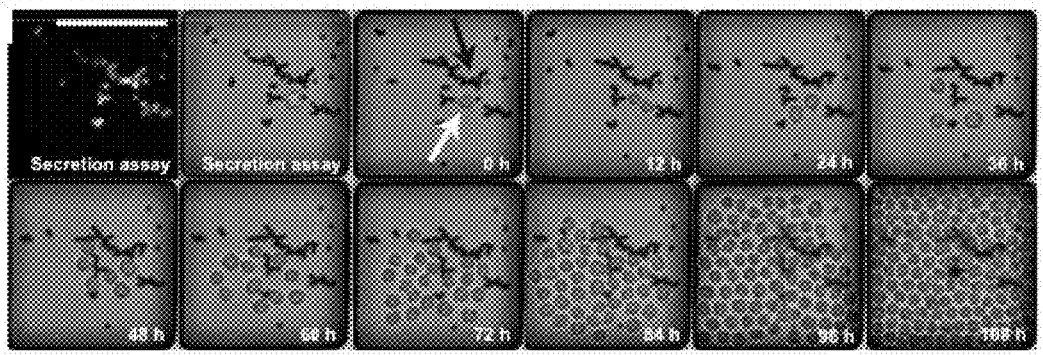
Figure 24:
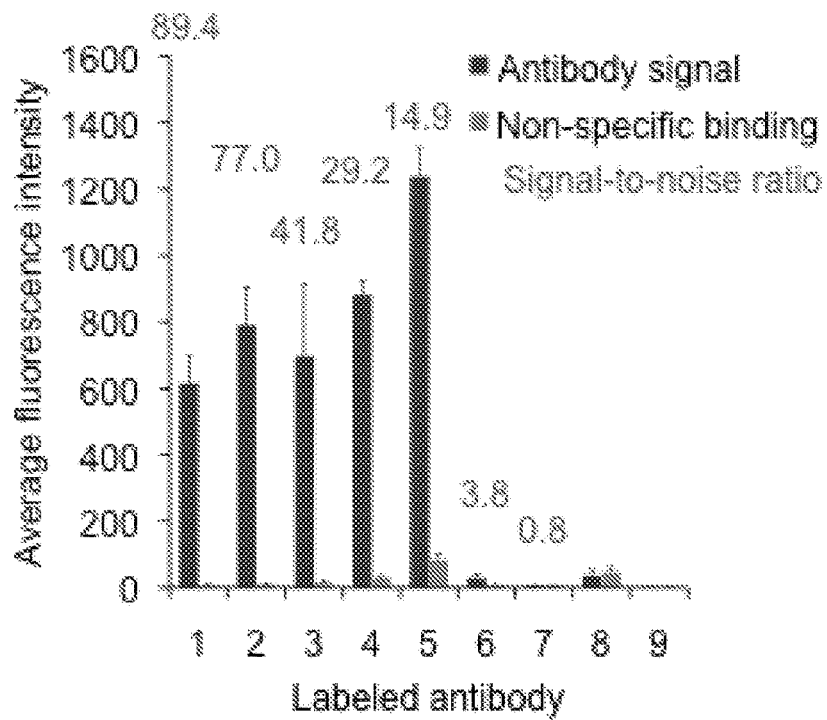
FIG. 24 shows antibody selection for the bead immunocapture assay, wherein fluorescence intensity was compared for beads exposed to cloning medium only (non-specific binding) and supernatant from a 3-day batch culture of CHO cells (antibody signal). The following labeled antibodies were tested: (1) Dylight 594-conjugated F(ab')2 fragment of rabbit anti-human IgG (H+L), (2) Dylight 594-conjugated F(ab')$_2$ fragment of goat anti-human IgG (H+L), (3) Dylight 594-conjugated F(ab')$_2$ fragment of donkey anti-human IgG (H+L), (4) Dylight 594-conjugated F(ab')$_2$ fragment of goat anti-human IgG, F(ab')$_2$ fragment-specific, (5) Alexa 594-conjugated goat anti-human IgG (H+L), (6) Biotin-conjugated F(ab')$_2$ fragment of chicken (H+L) labeled with Dylight 594-nutravidinand and (7) FITC-conjugated F(ab')$_2$ fragment of chicken (H+L). Lines 8 and 9 show bead autofluorescence in the red and green channels respectively. The Dylight 594-conjugated F(ab')$_2$ fragment of rabbit anti-human IgG (H+L) had the highest signal-to-noise ratio and was chosen for the assay.
Figures 25A, 25B, 25C, 25D, 25E, 25F, 25G, 25H:
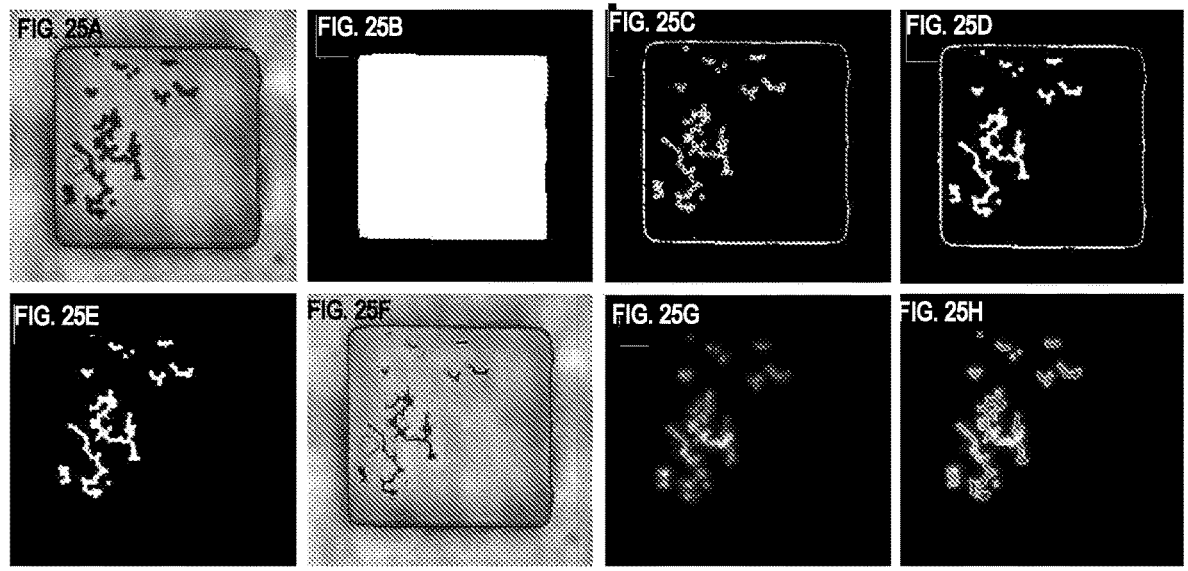
FIGS. 25A-25H show automated bead segmentation and measurement of mean bead intensity

In clonal cultures the accumulation of secreted antibody sufficient for detection normally requires many days of culture (e.g. 2 weeks), considerably extending the duration of initial cell specific productivity screens. This analysis is confounded by varied clonal growth rates and influenced by evaporation from small volume cultures. To address these challenges we developed a system to analyze within a few hours the productivity of single cells by taking advantage of the far more rapid product accumulation in nanoliter-volume chambers. Our microfluidic platform also was fabricated using the advantages of multilayer soft lithography as described herein. Each of the 1,600 chambers in the array was 4.1 nl in volume. The microfluidic device included micropumps downstream of the array to control loading rates and isolation valves to sequester all of the chambers when needed. In a first step, we loaded into the array a pool of transfected CHO cells producing varied levels of a recombinant monoclonal human IgG1 antibody. Different seeding concentrations were tested and we found that samples at $2 \times 10^6$ cells ml$^{-1}$ yielded a high proportion of chambers filled with single cells (typically 300-400 out of 1,600), close to the theoretical maximum of a Poisson distribution for this stochastic loading (FIG. 22). The high aspect ratio of the chambers sequestered suspension cells by gravity on the bottom of the chambers (FIG. 23A). Cells were then washed thoroughly to remove antibodies in the medium. Cloning medium containing polystyrene beads coated with protein A (diameter: 4.9 µm) was then introduced into the device and these beads allowed to settle (FIG. 23B). A medium wash was performed to clear beads that had not settled in the chambers (e.g. in the channels between chambers), and the isolation valve was then closed for 2 h (FIG. 23C). Following the incubation period, the array was washed with medium (FIG. 23D) and a solution of labeled detection antibody was loaded into the device. The chambers were isolated for an additional 15 min (FIG. 23E). We tested multiple antibodies and observed that F(ab')$_2$ fragments generally showed lower non-specific binding, consistent with their lack of constant region with affinity for Protein A (FIG. 24). The Dylight 594-conjugated F(ab')$_2$ fragment of rabbit anti-human IgG (H+L) gave the highest signal to noise ratio and was selected for the assay. The array was washed extensively to remove any unbound fluorescent antibody (FIG. 23F). A custom algorithm was then used to automatically focus on the beads and sets of bright field and fluorescent images were acquired from the entire array. After the assay, the isolation valve was left open and the cells were cultured in batch mode for 4 days (FIG. 23G). High producer clones with good proliferative capacity were then recovered from the device for further expansion.

Example 2.2 Assessment of Productivity from Single Cells

Figure 26:
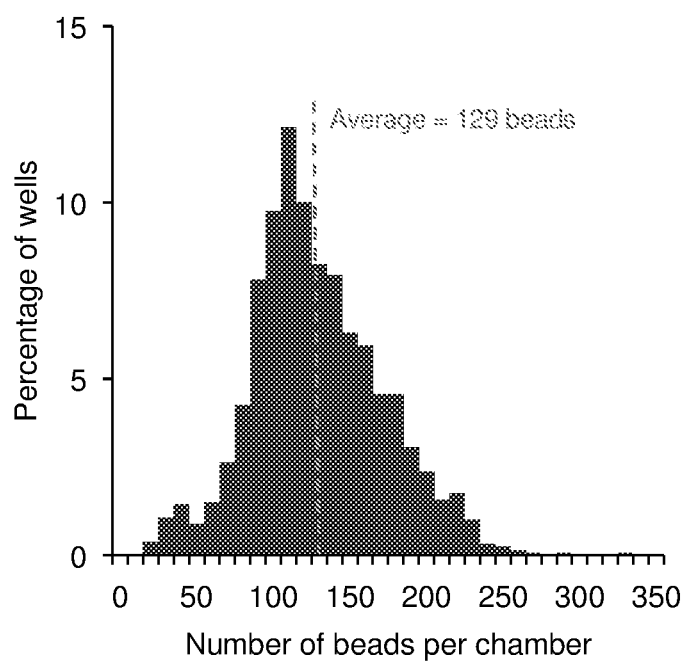
FIG. 26 shows a typical bead distribution in the microfluidic cell culture array, where on average, 129 beads per chamber were loaded using a solution containing 2 mg beads $ml^{-1}$.
Figure 27:
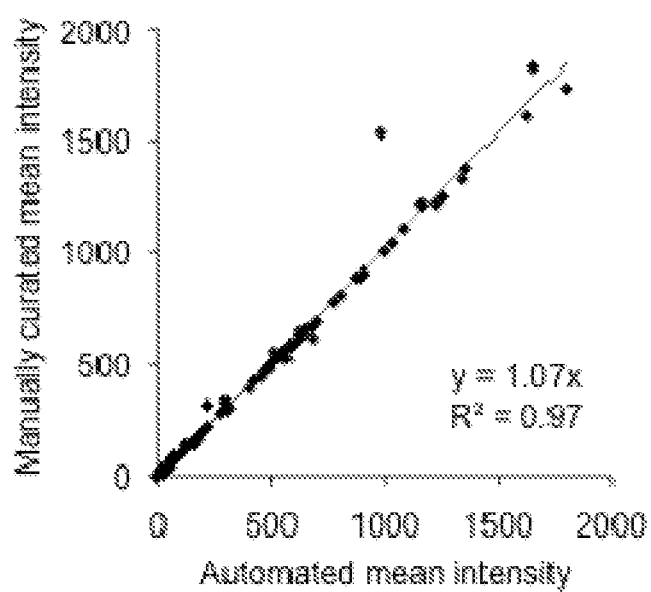
FIG. 27 shows the accuracy of the bead intensity measurement algorithm with images manually curated to correct for segmentation errors and compared to the automated measurement. The automated image analysis algorithm accurately measured bead mean fluorescence intensity.
Figure 28:
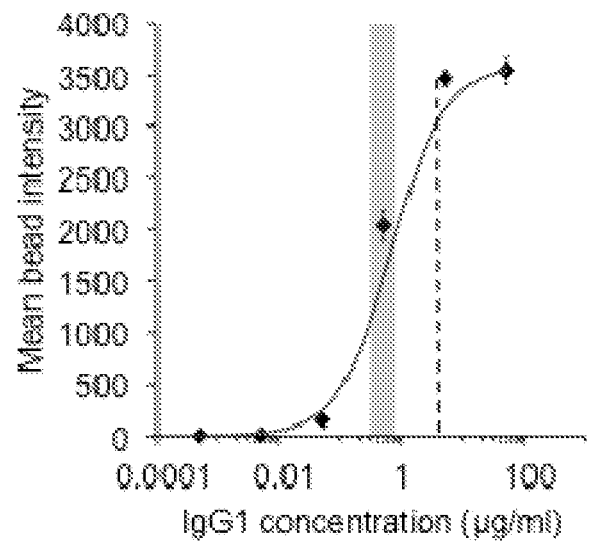
FIG. 28 shows a mean bead intensity as a function of the antibody concentration, wherein the antibody solutions were mixed to constant amounts of beads in tubes (0.5 mg $ml^{-1}$), incubated for 2 h, washed, and incubated for 15 min with the labeled antibody. After multiple washes, the beads were mounted on glass slides and bright field and fluorescent picture sets were taken to measure the mean bead intensity associated with antibody to bead ratios. The red line represents the data fit to a Langmuir equation ($I_{max}$=3592; K=1.50 ml $\mu g^{-1}$). Typical mean intensities for chambers containing the top 5% producer cells (shaded area) fell below saturation levels. Saturation occurred at around 4 µg $ml^{-1}$, corresponding to or 8 µg antibody (mg bead)$^{-1}$ (dashed line), consistent with the manufacturer specifications.

Custom scripts were developed to automatically segment the beads on bright field images and measure the fluorescence intensity in bead-covered areas (FIG. 25A-FIG. 25H). The mean bead intensity was calculated by dividing the total bead intensity in a chamber by the total projected area of the beads. Since beads often merged during segmentation, we estimated the numbers of beads by dividing total bead area by the theoretical projected area of one bead. Using a concentration of 2 mg beads ml$^{-1}$ typically resulted in on average 100-150 beads per chamber. An example of the bead distribution is provided in FIG. 26. We have developed a custom software to assess the accuracy of our image analysis algorithm and to manually correct bead segmentation errors. Aside from a few outliers, our bead immunocapture algorithm identified the top producer cells from a population (FIG. 27), thereby demonstrating the possible rapid automation of the assay. To distinguish the highest producers from the rest of the population, we needed to ensure that the beads were below saturation. We generated a curve of the mean bead intensity by making serial dilutions from a known concentration sample of the secreted IgG1 antibody. The bead saturation occurred at 8 µg of antibody (mg beads)$^{-1}$ (FIG. 28), consistent with the manufacturer specifications. Typical mean intensity values obtained in the bead immunocapture assay for the top 5% producers cells fell below the saturation level of the beads.

Figure 29:
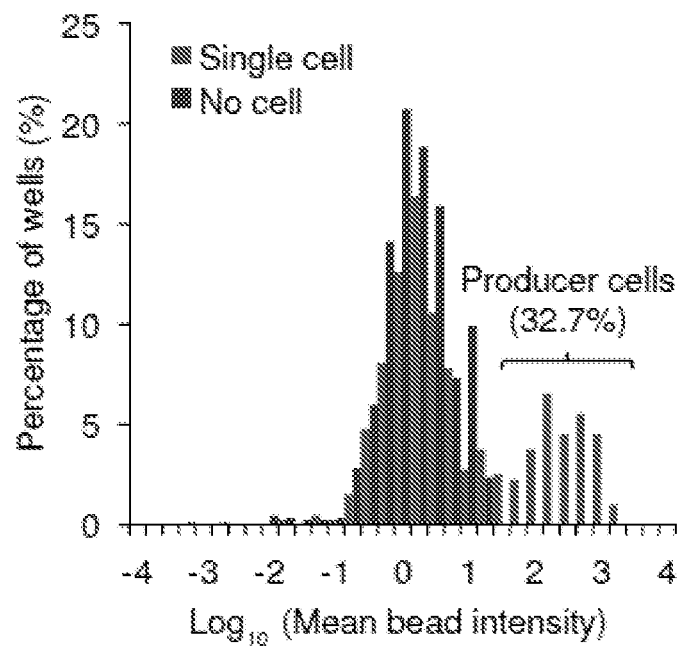
FIG. 29 shows a quantification of antibody secretion The mean bead intensity distinguishes high producer cells from non-producer cells by several orders of magnitude. Analysis of wells that did not contain cells (n=848 chambers) compared to chambers that contained single cells (n=397 chambers) showed minimal cross-contamination between chambers. Empty wells had a distribution of mean bead intensities (µ=2.96; CV=3.58) comparable to the distribution of non-producer cells (µ=2.70; CV=3.17). 32.7% of single cells had levels of mAb above the intensity of empty wells.

We first tested whether the bead immunocapture assay had sufficient sensitivity to distinguish producer cells from a pool of CHO cells transfected to secrete a human IgG1 monoclonal antibody. Since the stochastic loading introduced few cells into the array, we were able to compare the mean bead intensities of chambers containing single cells to the intensities of cell-free chambers. Highest producers had mean bead intensities that were 2 orders of magnitude larger than non-producing cells and the detectable producer cell population (32.7% of the cells) was easily distinguished from the low or non-producing population whose chamber intensity distribution matched that of the cell-free chambers (FIG. 29).

Example 2.3 Enhanced Cloning Efficiency

To test whether the microfluidic array could sustain maximal growth rates in clonal cultures, we compared the average growth rates of single cells in the microfluidic array to the average growth kinetics of single cells in multiwell plates (culture volume: 200 µl) and shake flask cultures seeded at $2.5 \times 10^5$ cells ml$^{-1}$. The cells had reduced growth rates when seeded as single cells in multiwell plates compared to shake flask cultures. In contrast, clonal cultures in the microfluidic device had growth rates comparable to the shake flask cultures (FIG. 30A). A single cell in a 4-nl microfluidic chamber is at an effective concentration of ~$2.5 \times 10^5$ cells ml$^{-1}$, and thus quickly provides a conditioned medium environment as these concentrations do in shake flask cultures. We then asked whether the microfluidic array could increase the cloning efficiency due to this higher seeding concentration. We used the percentage of clones with more than 8 cells to calculate the cloning efficiency. Clones in multiwell plates on average doubled every 23.2 h, and therefore clones with normal growth are expected to have gone through at least 3 divisions after 3 days. Single cells cultured in the microfluidic array had a significantly higher cloning efficiency than single cells cultured in multiwell plates (P value=0.06), most likely due to medium conditioning effects amplified by the 4 nl volumes (FIG. 30B). This enhanced cloning efficiency could allow the recovery of high-producer clones that would not survive limiting dilution in multiwell plates.

Example 2.4 Correlation of Surface-Bound mAb with Secretion

Membrane-bound antibody staining has been used as a tool to enrich for high producer cells[13,32]. However, there has been contradicting reports as to whether membrane-bound antibody staining is a reliable indicator of the amount of secreted proteins[13,19,33]. Our technology can conveniently measure membrane-bound and single-cell specific productivity simultaneously. We observed many instances where secreting cells did not stain for antibodies on their surface (e.g. FIG. 31A) and, inversely, where non-secreting cells exhibited surface antibodies (e.g. FIG. 31B). We did not see a strong correlation ($R^2=0.22$) between the specific cell productivity and cell intensity (FIG. 31C). While the population with high levels of surface-bound antibody appears to contain a greater fraction of high producer cells, our results show that this technique often excludes cells with high productivity and includes cells with low productivity.

Example 2.5 Recovery and Expansion of High-Producer Clones

Figure 32:
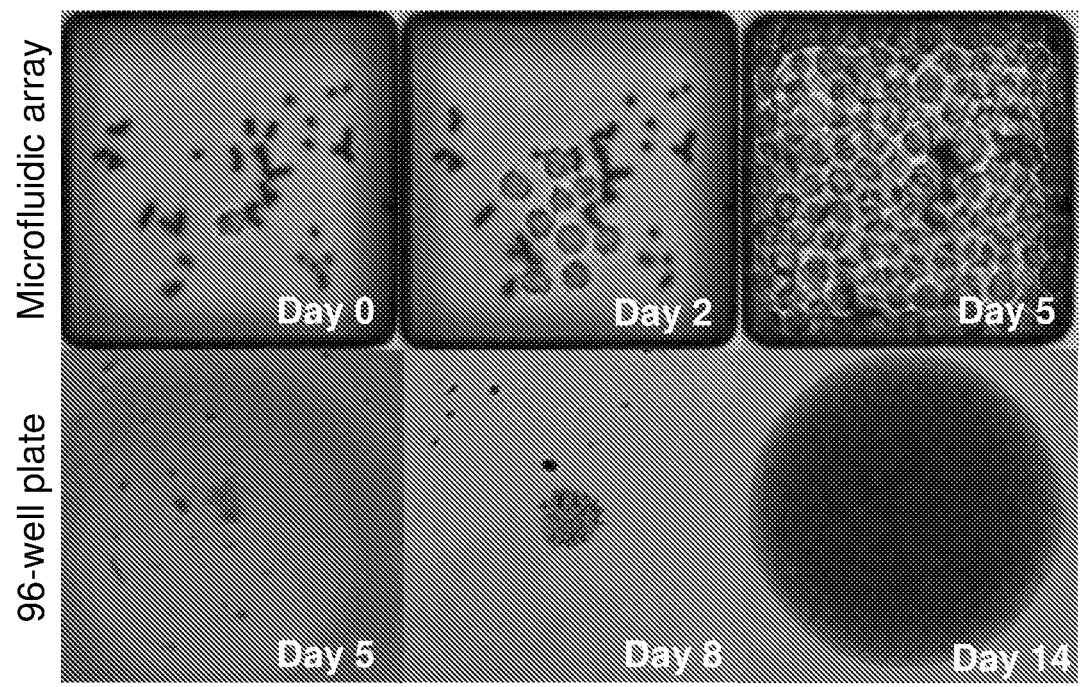
FIG. 32 shows a recovery of selected clones, with an example of a CHO cell cultured in the microfluidic array for 5 days and recovered in a 96-well plate for further expansion.
Figure 33A:
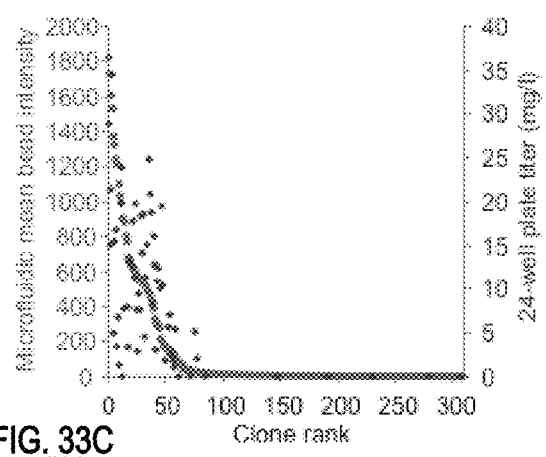
FIGS. 33A-33D show a selection of high-producer clones
Figure 33B:
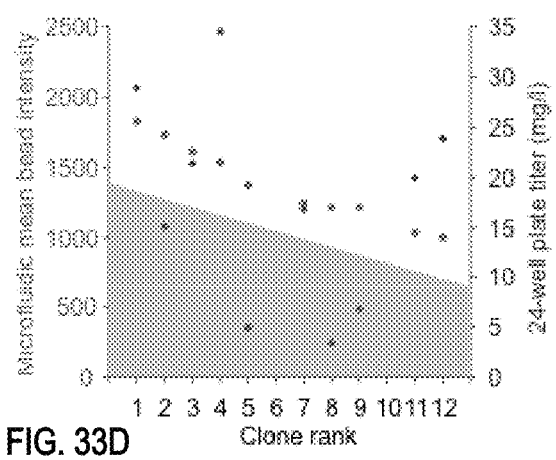
Figure 33C:
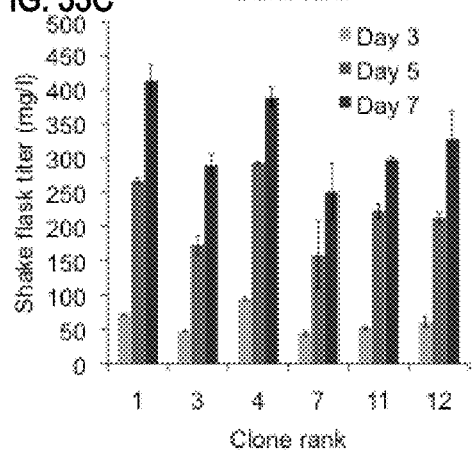
Figure 33D:
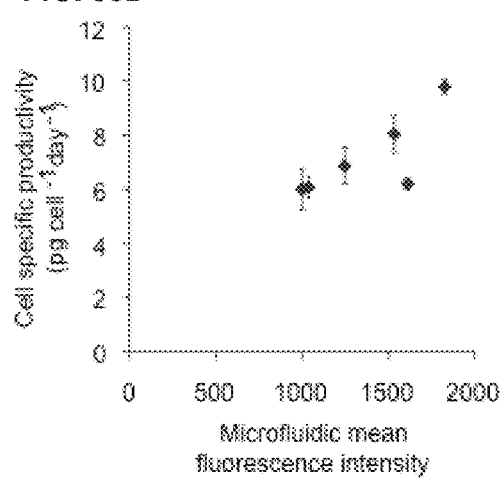

Clones from the same pool of CHO cells were isolated and then analyzed for their antibody productivity in the microfluidic array, cultured for 5 days and then transferred into 96-well plates. Out of the 308 clones, 60 were recovered including the 10% top producers as well as medium, low and non-producer clones. Of the 60 clones, 95% continued to proliferate in the 96-well plates (e.g. FIG. 32). They were cultured for 9 additional days, then transferred into 1 ml of medium in 24-well plates and after 5 days of culture, the supernatant was recovered for titer analysis. As shown in FIG. 33A, all single cells without productivity in the microfluidic screening were also negative after recovery, suggesting that there was no cross-contamination during the recovery process. Also, the microfluidic and multiwell measurements followed similar trends. We further scaled up to batch shake flask cultures 10 of the top 12 clones identified by the single-cell microfluidic assay. Four of those clones had already decreased their productivity at the 24-well plate stage (FIG. 33B) and likewise did not perform well in the shake flasks (FIG. 34A and FIG. 34B). The six high-ranked clones that had maintained their productivity at the 24-well plate stage (2% of the initial population) gave titers between 200-500 mg ml$^{-1}$ (FIG. 33C) with maximum specific productivities ranging from 6-10 pg cell$^{-1}$ day$^{-1}$ (FIG. 33D). The highest single-cell productivity identified with the microfluidic assay also gave the highest cell specific productivity in shake flask cultures, demonstrating the ability of the microfluidic single-cell secretion assay to identify and generate highly productive cell lines. The recovery, analysis and expansion of 10 high-ranked clones from the device led to 6 clones with SPR above 6 pg cell$^{-1}$ day$^{-1}$. Our method greatly reduces the burden of screening and sampling large numbers of multiwell plates to find the highest producers.

Example 2.6 Analysis of Clonal Heterogeneity

We then used our single cell microfluidic assay to determine the cell secretion profile of our top-ranked clone. As expected, the distribution was much tighter compared to the cell secretion pool and 97.3% of cells showed secretion levels above background (FIG. 35A). The range of bead intensity spanned over 3 orders of magnitude, suggesting relatively high diversity within the population. The standard deviation corresponded to 68.4% of the mean, a value comparable to what has been previously reported for intra-clonal heterogeneity based on intracellular fluorescent reporters (Pilbrough, W. et al. Plos One 4(12), 11 (2009)). Since this clonal population was much more homogeneous than the cell pool, we analyzed the intensity of wells containing more than one cell. There was a linear correlation between the mean bead intensity and the number of cell up for up to 3 cells ($R^2=0.99$), after which beads started to approach saturation (FIG. 35B). This data confirms the quantitative nature of the assay when performed on single cells.

The microfluidic platform described herein provides many advantages for the selection of high producer clones. Single-cell analysis, wherein one cell is retained in a chamber, allows hundreds of cells to be screened in a few hours, thereby eliminating the need to expand large numbers of clones in multiwell plates. This results in considerable economies in culture medium, culture vessels, time and labor. The prototype used in this study contained 1,600 chambers, enabling the analysis of 300-400 single cells per experiment based on the typical seeding density shown in FIG. 22. The design is easily scalable, whereby the number of chambers could be increased by several folds for populations where more clones need to be analyzed. Screening of a larger number of cells could help find clones with higher productivities without increasing the number of clones to be scaled up. This microfluidic approach differs from other single-cell secretion assays by allowing the analysis and culture of cells directly in medium without the need for a semi-solid matrix to contain the colonies and their secreted product. As described herein, the system may also be optimized for testing of hematopoietic stem cells to obtain robust growth rates and cellular functions comparable to large-scale cultures. The sensitivity of CHO cells to media conditioning revealed the ability of miniaturization to provide a more adequate culture environment for small numbers of cells. Nanovolume chambers allowed cells to be assayed and cultured at seeding concentrations comparable to shake flask cultures. The higher cloning efficiency obtained from sequestering cells in small volumes can select additional clones that only thrive at high cell concentration. Extending the culture for 4-5 days allows a clone to expand to numbers much more likely to survive when they are transferred to a multi-well plate, in turn increasing the number of high producer clones recovered. Since cells were analyzed within 2 hours of being retrieved from a shake flask culture, they are more likely to be in a similar state to suspension cultures than if they were assayed after multiple days of static culture (e.g. 96-well plate). Together these features bring the right environment to obtain good prediction of the cell specific productivity in batch shake flasks cultures from single-cell measurements. It could be possible to further exploit the flexibility of the system by retrieving cells from a fed-batch culture for analysis and assaying them in conditioned media, leading to an even closer match to the conditions typically used for large-scale mAb production.

Our platform provides similar flexibility and throughput as single-cell secretion assays based on microengraving methods (Love, J. C. et al. Nature Biotechnology 24(6), 703-707 (2006)), but the integration of the bead immunocapture in an enclosed device has the advantages of allowing for in situ clonal expansion at non-diluted concentrations. It could be possible to capture the secreted antibody directly onto Protein A/G-coated PDMS chambers instead of using bead immunocapture. However, the hydrophobic nature of PDMS provides a low-binding surface, which can be a desirable feature to maintain cells that have been adapted for suspension culture. As well, the use of beads in proximity of the cells concentrates the signal and possibly leads to better sensitivity. With microengraving, fibronectin coating and attachment periods of up to 6-12 h are needed to ensure that single cells are not lost when the glass slide is removed, and then cells are trypsinized for recovery (Park, S. et al. Journal of Biotechnology 156(3), 197-202 (2011)). The high-aspect ratio chambers described herein gently capture the clones by gravity, enabling suspension-adapted cell lines to remain on a non-adhesive surface and to be easily recovered. As the entire process uses integrated microfluidics, it could easily be fully automated.

The easy coupling of microfluidic devices with time-lapse imaging allows clonal tracking over time, including the initial verification of clonality. That colonies arise from single cells can be confirmed by visual observation. Alternatively, the process could be automated with high accuracy using a live/dead stain of the cells. The ease of automation of programmable microfluidic systems make this platform well suited for industrial applications. For the production of therapeutic mAbs, the detection antibody could be replaced by a labeled recombinant Protein A and hence provide a process devoid of animal components.

Predicting the performance of an entire clone from a single cell within 6 hours (for example, between 5 minutes to 6 hrs—for the CHO cells described in Example 2 the determination was made within 2 hrs) could be influenced by significant temporal variations in mAb secretion. Reports have shown that variations in secretion levels throughout cell cycle are mainly attributed to changes in cell size (Pilbrough, W. et al. Plos One 4(12), 11 (2009); and Lloyd, D. R. et al. Cytotechnology 34(1-2), 59-70 (2000)), but since those were made on population measurement it is not clear whether the productivity of a single cell changes as it grows. Single-cell protein secretion in yeast has been measured by microengraving and no relation was found between productivity and cell cycle stage (Love, K. R. et al. Biotechnology and Bioengineering 106(2), 319-325 (2010)). Single-molecule analysis of mRNA transcripts have shown bursts of transcription by CHO and other cell types (Raj, A. et al. Plos Biology 4(10), 1707-1719 (2006); and Raj, A. et al. Nature Methods 5(10), 877-879 (2008)), leading to large fluctuations in transcript expression. However, simultaneous measurements of transcript and protein levels have showed that transcriptional fluctuations are not entirely propagated to secretion levels (Pilbrough, W. et al. Plos One 4(12), 11 (2009)) with the secretion machinery being the limiting factor at high transcriptional levels (Fann, C. H. et al. Biotechnology and Bioengineering 63(4), 464-472 (1999); Schroder, M. & Friedl, P Biotechnology and Bioengineering 53(6), 547-559 (1997)). This suggests that even though secretion rates can be influenced by stochastic variations (Love, K. R. et al. Biotechnology and Bioengineering 106 (2), 319-325 (2010)), screening results based on single-cell secretion are less prone to be confounded by temporal variations than would be measurements obtained from transcriptional analysis at the single-cell level (e.g. GFP containing expression vectors). The platform described herein can measure both surface and secreted mAb levels simultaneously. The assay could further be combined with fluorescent reporters genes and proteins to gain a better understanding of the factors regulating the mAb or other cell product production at the transcription, translation and secretion levels.

The generation of stable clones is an important aspect of cell line selection. Generally, the assessment of stability is performed over multiple passages. A decline in productivity will propagate to a detectable fraction of the population much faster if the initial assay is done on a single cell rather than a bigger colony. Indeed, a fraction of the highly ranked clones exhibited lower productivities in multiwell plates than in the microfluidic assay. These clones can readily be identified and eliminated at the 24-well plate stage to avoid investing resources and efforts on the scale up of either poor producers or unstable clones. Single-cell analysis is a powerful tool to assess the heterogeneity in cell populations. Performing the same assay on clones could be used to identify minor fractions of clonal population that have reduced mAb production rates before a decrease in titers could be detected. Analysis of intracellular mAb using FACS is used by some as a tool to identify unstable clones (Dorai, H. et al. Biotechnology and Bioengineering 109(4), 1016-1030 (2011)). Our platform could enable secretion analysis on single cells from clonal population to obtain an early assessment of clone homogeneity and detect signs of instability.

There is an increasing need in the industry to accelerate the development of mAbs and other cell products. The throughput, sensitivity, flexibility and ease of automation of microfluidic single-cell analysis systems bring new tools to reach this goal. Cell line selection is only one example from a plethora of immunological applications that could benefit from the combination of clonal cell culture and high-throughput secretion screens. These include hybridoma generation, isolation of rare activated T cells, selection of new antibodies from primary cells or directed evolution in mammalian cells. With the ability to obtain robust and, as shown in this work, more efficient culture conditions in small volumes, microfluidic devices have potential to becoming vessels of choice to search for rare cells in heterogeneous populations.

What is claimed is:

1. A method for culturing single antibody secreting cells, comprising:
   introducing a population of antibody secreting cells via a single introduction port into a microfluidic device comprising a plurality of microfluidic chambers, wherein each microfluidic chamber of the plurality comprises an inlet and a cell trap, the single introduction port is in fluid communication with a flow channel that is in fluid communication with the inlets of the plurality of microfluidic chambers,
   transporting cells of the population via the introduction port and flow channel into different microfluidic chambers of the plurality,
   wherein single cells of the population are retained individually in different microfluidic chambers of the plurality via the cell trap,
   providing a cell culture medium to the plurality of microfluidic chambers via the flow channel and the inlets of the microfluidic chambers, and
   exchanging the cell culture medium in the microfluidic chambers via the flow channel and the inlets of the microfluidic chambers, to create a plurality of individual clonal cell populations of antibody secreting cells, wherein the individual clonal cell populations are retained in the same microfluidic chamber as their respective parental cell, thereby culturing the single antibody secreting cells.

2. The method of claim 1, further comprising selecting one or more of the individual clonal cell populations from the plurality based on a characteristic to provide one or more selected individual clonal cell populations.

3. The method of claim 1, further comprising measuring antibody secreted by the individual clonal cell populations.

4. The method of claim 2, further comprising measuring antibody secreted by the individual clonal cell populations.

5. The method of claim 1, wherein exchanging the cell culture medium is via diffusion or convection.

6. The method of claim 1, wherein exchanging the cell culture medium is via diffusion.

7. The method of claim 1, wherein the exchanging the cell culture medium is continuous.

8. The method of claim 1, wherein the cell trap is a mechanical trap, a hydrodynamic trap, a hydrodynamic balancing trap, a dielectrophoretic trap, a magnetic trap, an acoustic trap, or an optical trap.

9. The method of claim 1, wherein the cell trap is a dielectrophoretic trap.

10. The method of claim 2, wherein the cell trap is a dielectrophoretic trap.

11. The method of claim 3, wherein the cell trap is a dielectrophoretic trap.

12. The method of claim 4, wherein the cell trap is a dielectrophoretic trap.

13. The method of claim 1, wherein the single cells of the population are retained individually in the different microfluidic chambers at a concentration of greater than or equal to 50,000 cells per mL.

14. The method of claim 1, wherein the single cells of the population are retained individually in the different microfluidic chambers at a concentration of greater than or equal to 250,000 cells per mL.

15. The method of claim 1, wherein the population of cells is derived from an adherent cell line.

16. The method of claim 1, wherein the population of cells grow while suspended in cell culture medium.

17. The method of claim 1, further comprising measuring the average cell growth rate in the different microfluidic chambers.

18. The method of claim 2, further comprising measuring the average cell growth rate in the different microfluidic chambers.

19. The method of claim 9, further comprising measuring the average cell growth rate in the different microfluidic chambers.

20. The method of claim 4, wherein measuring comprises flowing a fluid comprising an immunostaining agent, an enzymatic reagent, a dye, or a functionalized bead into the individual chambers.

21. The method of claim 2, wherein the cell characteristic is selected from quantity of secreted antibody, quality of secreted antibody, proliferation, morphology, gene expression, fluorescent reporter, surface proteins, genealogical pedigree, viability, apoptosis, autophagy, metabolism, clone homogeneity, or clone heterogeneity.

22. The method of claim 4, wherein measuring comprises fluorescent imaging.

23. The method of claim 2, further comprising recovering the selected individual clonal cell population, or a subset thereof.

24. The method of claim 10, further comprising recovering the selected individual clonal cell population, or a subset thereof.

25. The method of claim 1, further comprising monitoring the growth of the cells in the different microfluidic chambers.

26. The method of claim 2, further comprising monitoring the growth of the cells in the different microfluidic chambers.

27. The method of claim 10, further comprising monitoring the growth of the cells in the different microfluidic chambers.

28. The method of claim 25, wherein monitoring comprises time lapse imaging of the different microfluidic chambers.

29. The method of claim 26, wherein monitoring comprises time lapse imaging of the different microfluidic chambers.

30. The method of claim 27, wherein monitoring comprises time lapse imaging of the different microfluidic chambers.

* * * * *